(12) United States Patent
Wands et al.

(10) Patent No.: US 7,867,705 B2
(45) Date of Patent: Jan. 11, 2011

(54) FRIZZLED PROTEINS AND DETECTION AND TREATMENT OF CANCER

(75) Inventors: Jack R. Wands, Providence, RI (US); Philippe Merle, Lyons (FR); Suzanne M. De La Monte, East Greenwich, RI (US)

(73) Assignee: Rhode Island Hospital, a Lifespan-Partner, Providence, RI (US)

( * ) Notice: Subject to any disclaimer, the term of this patent is extended or adjusted under 35 U.S.C. 154(b) by 475 days.

(21) Appl. No.: 11/575,627

(22) PCT Filed: Jan. 5, 2005

(86) PCT No.: PCT/US2005/001514

§ 371 (c)(1),
(2), (4) Date: Dec. 4, 2007

(87) PCT Pub. No.: WO2006/036179

PCT Pub. Date: Apr. 6, 2006

(65) Prior Publication Data

US 2008/0194457 A1    Aug. 14, 2008

Related U.S. Application Data

(60) Provisional application No. 60/611,919, filed on Sep. 21, 2004.

(51) Int. Cl.
*C12Q 1/68* (2006.01)
*G01N 33/53* (2006.01)

(52) U.S. Cl. .......................... 435/6; 435/7.23; 436/501; 436/518

(58) Field of Classification Search ........................ None
See application file for complete search history.

(56) References Cited

U.S. PATENT DOCUMENTS

| 6,043,053 | A | 3/2000 | Barnes et al. |
| 6,924,141 | B2 | 8/2005 | Morgan et al. |
| 2003/0165500 | A1 | 9/2003 | Rhee et al. |

FOREIGN PATENT DOCUMENTS

WO    2004/032838    4/2004

OTHER PUBLICATIONS

Katoh, "Regulation of *WNT3* and *WNT3A* mRNAs in human cancer cell lines NT2, MCF-7, and MKN45", *International Journal of Oncology*, vol. 20:373-377 (2002).

Kim et al., "Functional interaction between Wnt3 and Frizzled-7 leads to activation of the Wnt/β-catenin signaling pathway in hepatocellular carcinoma cells," Journal of Hepatology, 48:780-791 (2008).

Aberle et al., "Cadherin-Catenin Complex: Protein Interactions and Their Implications for Cadherin Function," *Journal of Cellular Biochemistry*, vol. 61:514-523 (1996).

Anna et al., "Expression of Potential β-catenin targets, cyclin D1, c-Jun, c-Myc, E-cadherin, and EGFR in chemically induced hepatocellular neoplasms from B6C3F1 mice," *Toxicology and Applied Pharmacology*, vol. 190:135-145 (2003).

Anthony, "Hepatocellular carcinoma: an overview," *Histopathology*, vol. 39:109-118 (2001).

Aoki et al., "Oncogenic transformation by β-Catenin: deletion analysis and characterization of selected target genes," *Oncogene*, vol. 21:6983-6991 (2002).

Ban et al., "GSK-3β phosphorylation and alteration of β-catenin in hepatocellular carcinoma," *Cancer Letters*, vol. 199:201-208 (2003).

Bhanot et al., "A new member of the *frizzled* family from *Drosophila* functions as a Wingless receptor," *Nature*, vol. 382:225-230 (1996).

Bièche et al., "Quantitation of *MYC* Gene Expression in Sporadic Breast Tumors with a Real-Time Reverse Transcription-PCR Assay," *Cancer Research*, vol. 59:2759-2765 (1999).

Bradley et al., "The proto-oncogene *int*-1 encodes a secreted protein associated with the extracellular matrix," *The EMBO Journal*, vol. 9:1569-1575 (1990).

Cagatay et al., "p53 Mutation as a source of aberrant β-catenin accumulation in cancer cells," *Oncogene*, vol. 21:7971-7980 (2002).

Calvisi et al., "Activation of β-Catenin during Hepatocarcinogenesis in Transgenic Mouse Models: Relationship to Phenotype and Tumor Grade," *Cancer Research*, vol. 61:2085-2091 (2001).

Calvisi et al., "Disruption of β-Catenin Pathway or Genomic Instability Define Two Distinct Categories of Liver Cancer in Transgenic Mice," *Gastroenterology*, vol. 126:1374-1386 (2004).

Candidus et al., "No Evidence for Mutations in the α- and β-Catenin Genes in Human Gastric and Breast Carcinomas," *Cancer Research*, vol. 56:49-52 (1996).

Cariani et al., "Differential Expression in Insulin-like Growth Factor II mRNA in Human Primary Liver Cancers, Benign Liver Tumors, and Liver Cirrhosis," *Cancer Research*, vol. 48:6844-6849 (1988).

Carloni et al., "The Integrin α6β1, Is Necessary for the Matrix-Dependent Activation of FAK and MAP Kinase and the Migration of Human Hepatocarcinoma Cells," *Hepatology*, vol. 34:42-49 (2001).

Carruba et al., "Truncated Form of β-Catenin and Reduced Expression of Wild-Type Catenins Feature HepG2 Human Liver Cancer Cells," *Annals New York Academy of Sciences*, vol. 886:212-216 (1999).

Caselmann et al., "Hepatitis C virus infection as a major risk factor for hepatocellular carcinoma," *Journal of Hepatology*, vol. 24:61-66 (1996).

Cha et al., "Hepatitis B Virus X Protein Is Essential for the Activation of Wnt/β-Catenin Signaling in Hepatoma Cells," *Hepatology*, vol. 39:1683-1693 (2004).

(Continued)

*Primary Examiner*—Misook Yu
(74) *Attorney, Agent, or Firm*—Fish & Richardson P.C.

(57) ABSTRACT

The present specification provides, inter alia, methods of using Wnt and FZD proteins, genes, FZD and Wnt-specific antibodies and probes in diagnosis and treatment of cancer and for screening test compounds for an ability to treat cancer. Also disclosed are compounds useful for treating cancer such as liver cancer.

12 Claims, 19 Drawing Sheets

OTHER PUBLICATIONS

Chan et al., "Evidence that Armadillo Transduces Wingless by Mediating Nuclear Export or Cytosolic Activation of Pangolin," *Cell*, vol. 111:265-280 (2002).

Cheon et al., "β-Catenin stabilization dysregulates mesenchymal cell proliferation, motility, and invasiveness and causes aggressive fibromatosis and hyperplastic cutaneous wounds," *PNAS*, vol. 99:6973-6978 (2002).

Chung, "The Genetic Basis of Colorectal Cancer: Insights into Critical Pathways of Tumorigenesis," *Gastroenterology*, vol. 119:854-865 (2000).

Clevers, "Axin and hepatocellular carcinomas," *Nature Genetics*, vol. 24:206-208 (2000).

Davila et al., "Hepatitis C Infection and the Increasing Incidence of Hepatocellular Carcinoma: A Population-Based Study," *Gastroenterology*, vol. 127:1372-1380 (2004).

de La Coste et al., "Somatic mutations of the β-Catenin gene are frequent in mouse and human hepatocellular carcinoma," *Proc. Natl. Acad. Sci. USA*, vol. 95:8847-8851 (1998).

de la Monte et al., "ATP Luminescence-Based Motility-Invasion Assay," *Biotechniques*, vol. 33:98-106 (2002).

De Souza et al., "*M6P/IGF2R* gene is mutated in human hepatocellular carcinomas with loss of heterozygosity," *Nature Genetics*, vol. 11:447-449 (1995).

Devereux et al., "Mutation of β-catenin is an early event in chemically induced mouse hepatocellular carcinogenesis," *Oncogene*, vol. 18: 4726-4733 (1999).

Devereux et al., "*CTNNB1* Mutations and β-Catenin Protein Accumulation in Human Hepatocellular Carcinomas Associated With High Exposure to Aflatoxin B1," *Molecular Carcinogenesis*, vol. 31:68-73 (2001).

Dhoot et al., "Regulation of Wnt Signaling and Embryo Patterning by an Extracellular Sulfatase," *Science*, vol. 293:1663-1666 (2001).

Du et al., "Identification of Distinct Classes and Functional Domains of Wnts through Expression of Wild-Type and Chimeric Proteins in *Xenopus* Embryos," *Molecular and Cell Biology*, vol. 15:2625-2634 (1995).

Dubois et al., "Time-course development of differentiated hepatocarcinoma and lung metastasis in transgenic mice," *Journal of Hepatology*, vol. 13:227-239 (1991).

El-Serag et al., "Rising Incidence of Hepatocellular Carcinoma in the United States," *The New England Journal of Medicine*, vol. 340:745-750 (1999).

Etiemble et al., "Liver-specific expression and high oncogenic efficiency of c-*myc* transgene activated by woodchuck hepatitis virus insertion," *Oncogene*, vol. 9:727-737 (1994).

Fausto et al., "Mouse Liver Tumorigenesis: Models, Mechanisms, and Relevance to Human Disease," *Seminars in Liver Disease*, vol. 19:243-252 (1999).

Feitelson et al., "Genetic mechanisms of hepatocarcinogenesis", *Oncogene*, vol. 21:2593-2604 (2002).

Frith et al., "Tumors of the liver," *Pathology of Tumors in Laboratory Animals.*, V. Turusov and U. Mohn, editors, IARC. Lyon, France, vol. 2:223-270 (1994).

Giles et al., "Caught up in a Wnt storm: Wnt signaling in cancer," *Biochimica et Biophysica Acta*, vol. 1653:1-24 (2003).

Gregorieff et al., "Expression Pattern of Wnt Signaling Components in the Adult Intestine," *Gastroenterology*, vol. 129:626-638 (2005).

Hanahan et al., "The Hallmarks of Cancer," *Cell*, vol. 100:57-70 (2000).

He et al., "Identification of c-*MYC* as a Target of the APC Pathway," *Science*, vol. 281:1509-1512 (1998).

Herrmann et al., "Oncogenic Role and Specificity of Frizzled Receptor Expression in Animal Models of Hepatocellular Carcinoma," *Hepatology*, vol. 38:180A (2003).

Holcombe et al., "Expression of Wnt ligands and Frizzled receptors in colonic mucosa and in colon carcinoma," *J. Clin. Pathol. Mol. Pathol.*, vol. 55:220-226 (2002).

Hommura et al., "Increased Expression of β-Catenin Predicts Better Prognosis in Nonsmall Cell Lung Carcinomas," *Cancer*, vol. 94:752-758 (2002).

Hsu et al., "β-Catenin Mutations Are Associated with a Subset of Low-Stage Hepatocellular Carcinoma Negative for Hepatitis B Virus and with Favorable Prognosis," *American Journal of Pathology*, vol. 157:763-770 (2000).

Hsu et al., "Mutational hotspot in the p53 gene in human hepatocellular carcinomas," *Nature*, vol. 350.:427-428 (1991).

Huang et al., "β-Catenin Mutations Are Frequent in Human Hepatocellular Carcinomas Associated with Hepatitis C virus Infection," *American Journal of Pathology*, vol. 155:1795-1801 (1999).

Idilman et al., "Pathogenesis of hepatitis B and C-induced hepatocellular carcinoma," *Journal of Viral Hepatitis*, vol. 5:285-299 (1998).

Iozzo et al., "Aberrant Expression of the Growth Factor *Wnt-5A* in Human Malignancy," *Cancer Research*, vol. 55:3495-3499 (1995).

Inagawa et al., "Expression and Prognostic Roles of β-Catenin in Hepatocellular Carcinoma: Correlation with Tumor Progression and Postoperative Survival," *Clinical Cancer Research*, vol. 8:450-456 (2002).

Jönsson et al., "Involvement of adenomatous polyposis coli (APC)/β-catenin signalling in human breast cancer," *European Journal of Cancer*, vol. 36:242-248 (2000).

Jones et al., "Secreted Frizzled-related proteins: searching for relationships and patterns," *BioEssays*, vol. 24:811-820 (2002).

Katoh, "Molecular cloning and characterization of human *WNT3*," *International Journal of Oncology*, vol. 19:977-982 (2001).

Kinzler et al., "Lessons from Hereditary Colorectal Cancer," *Cell*, vol. 87:159-170 (1996).

Kirikoshi et al., "Molecular cloning and characterization of human *WNT11*," *International Journal of Molecular Medicine*, vol. 8:651-656 (2001).

Kirikoshi et al., "Up-regulation of *Frizzled*-7 (*FZD7*) in human gastric cancer," *Int. J. Oncol.*, vol. 19:111-115 (2001).

Kolligs et al., "Neoplastic Transformation of RK3E by Mutant β-Catenin Requires Deregulation of Tcf/Lef Transcription but Not Activation of c-*myc* Expression," *Molecular and Cellular Biology*, vol. 19:5696-5706 (1999).

Korinek et al., "Constitutive Transcriptional Activation by a β-Catenin-Tcf Complex in APC$^{-/-}$Colon Carcinoma," *Science*, vol. 275:1784-1787 (1997).

Kühl et al., "The Wnt/Ca$^{2+}$ pathway: a new vertebrate Wnt signaling pathway takes shape," *Trends in Genet.*, vol. 16:279-283 (2000).

Laurent-Puig et al., "Genetic Alterations Associated With Hepatocellular Carcinomas Define Distinct Pathways of Hepatocarcinogenesis," *Gastroenterology*, vol. 120:1763-1773 (2001).

Legoix et al., "Beta-catenin mutations in hepatocellular carcinoma correlate with a low rate of loss of heterozygosity," *Oncogene*, vol. 18:4044-4046 (1999).

Lejeune et al., "*Wnt5a* Cloning, Expression, and Up-Regulation in Human Primary Breast Cancers," *Clinical Cancer Research*, vol. 1:215-222 (1995).

Liang et al., "Wnt5a Inhibits B cell proliferation and functions as a tumor suppressor in hematopoietic tissue," *Cancer Cell*, vol. 4:349-360 (2003).

Lin et al., "β-Catenin, a novel prognostic marker for breast cancer: Its role in cyclin D1 expression and cancer progression," *PNAS*, vol. 97:4262-4266 (2000).

Lin et al., "Dally cooperates with *Drosophila* Frizzled 2 to transduce Wingless signalling", *Nature*, vol. 400:281-284 (1999).

Lisovsky et al., "Frizzled Receptors Activate a Novel JNK-Dependent Pathway that May Lead to Apoptosis," *Current Biology*, vol. 12:53-58 (2002).

Liu et al., "Phosphorylation of β-Catenin and Epidermal Growth Factor Receptor by Intestinal Trefoil Factor," *Laboratory Investigation*, vol. 77:557-563 (1997).

Maloney et al., "Differential translocation of protein kinase C isozymes by phorbol esters, EGF, and ANG II in rat liver WB cells," *Am. J. Physiol.*, vol. 274:C974-C982 (1998).

Maye et al., "Multiple Mechanisms for Wnt11-mediated Repression of the Canonical Wnt Signaling Pathway," *The Journal of Biological Chemistry*, vol. 279:24659-24665 (2004).

Merle et al., "Oncogenic role of the frizzled-7/β-Catenin pathway in hepatocellular carcinoma," *Journal of Hepatology*, vol. 43:854-862 (2005).

Merle et al., "Functional Consequences of Frizzled-7 Receptor Overexpression in Human Hepatocellular Carcinoma," *Gastroenterology*, vol. 127:1110-1122 (2004).

Merle et al., "The Role of Frizzled 7 Expression in the Pathogenesis of Human Hepatocellular Carcinoma," *Journal of Hepatology*, vol. 38(4):589A (2003).

Merle et al., Long-term high-dose interferon-α therapy delays *Hepadnavirus*-related hepatocarcinogenesis in X/*myc* transgenic mice, *Oncogene*, vol. 22:2762-2771 (2003).

Merle et al., "Preliminary results of interferon-α therapy on woodchuck hepatitis virus-induced hepatocarcinogenesis: possible benefit in female transgenic mice," *The Journal of Hepatology*, vol. 34:562-569 (2001).

Mohr et al., "Ethanol Inhibits Hepatocyte Proliferation in Insulin Receptor Substrate 1 Transgenic Mice," *Gastroenterology*, vol. 115:1558-1565 (1998).

Monga et al., "Hepatocyte Growth Factor Induces Wnt-independent Nuclear Translocation of β-Catenin after Met- β-Catenin Dissociation in Hepatocytes," *Cancer Research*, vol. 62:2064-2071 (2002).

Moore et al., "p53 Mutations Are Not Selected for in Simian Virus 40 T-Antigen-Induced Tumors from Transgenic Mice," *Journal of Virology*, vol. 66:641-649 (1992).

Morin, "β-Catenin signaling and cancer," *BioEssays*, vol. 21:1021-1030 (1999).

Morin et al., "Activation of β-Catenin-Tcf Signaling in Colon Cancer by Mutations in β-Catenin or APC," *Science*, vol. 275:1787-1790 (1997).

Müller et al., "Phosphorylation and Free Pool of β-Catenin Are Regulated by Tyrosine Kinases and Tyrosine Phosphatases during Epithelial Cell Migration," *The Journal of Biological Chemistry*, vol. 274:10173-10183 (1999).

Murray et al., "Mortality by Cause for Eight Regions of the World: Global Burden of Disease Study," *Lancet* 349:1269-1276 (1997).

Nagai et al., "Comprehensive allelotyping of human hepatocellular carcinoma," *Oncogene*, vol. 14:2927-2933 (1997).

Nhieu et al., "Nuclear Accumulation of Mutated β-Catenin in Hepatocellular Caracinoma Is Associated with Increased Cell Proliferation," *American Journal of Pathology*, vol. 155:703-710 (1999).

Orford et al., "Exogenous Expression of β-Catenin Regulates Contact Inhibition, Anchorage-independent Growth, Anoikis, and Radiation-induced Cell Cycle Arrest," *The Journal of Cell Biology*, vol. 146:855-867 (1999).

Park et al., "Nuclear localization of β-Catenin is an important prognostic factor in hepatoblastoma," *Journal of Pathology*, vol. 193:483-490 (2001).

Polakis et al., "The Adenomatous Polyposis Coli (APC) Tumor Suppressor," *Biochim. Biophys. Acta.*, vol. 1332:F-127-147 (1997).

Reichsman et al., "Glycosaminoglycans Can Modulate Extracellular Localization of the *wingless* Protein and Promote Signal Transduction," *The Journal of Cell Biology*, vol. 135:819-827 (1996).

Renard et al., "Hepatocellular carcinoma in WHV/N-*myc*2 transgenic mice: oncogenic mutations of β-catenin and synergistic effect of p53 null alleles," *Oncogene*, vol. 19:2678-2686 (2000).

Rimm et al., "Frequent Nuclear/Cytoplasmic Localization of β-Catenin without Exon 3 Mutations in Malignant Melanoma," *American Journal of Pathology*, vol. 154:325-329 (1999).

Roelink et al., "Molecular Cloning and Chromosomal Localization to 17q21 of the Human WNT3 Gene," *Genomics*, vol. 17:790-792 (1993).

Roth et al., "Secreted Frizzled-related proteins inhibit motility and promote growth of human malignant glioma cells," *Oncogene*, vol. 37:4210-4220 (2000).

Satoh et al., "*AXIN1* mutations in hepatocellular carcinomas, and growth suppression in cancer cells by virus-mediated transfer of *AXIN1*," *Nature Genetics*, vol. 24:245-250 (2000).

Satyamoorthy et al., "Insulin-like Growth Factor-1 Induces Survival and Growth of Biologically Early Melanoma Cells through Both the Mitogen-activated Protein Kinase and β-Catenin Pathways," *Cancer Research*, vol. 61:7318-7324 (2001).

Shimizu et al., "Transformation by Wnt Family Proteins Correlates with Regulation of β-Catenin," *Cell Growth & Differentiation*, vol. 8:1349-1358 (1997).

Smolich et al., "*Wnt* Family Proteins Are Secreted and Associated with the Cell Surface," *Molecular Biology of the Cell*, vol. 4:1267-1275 (1993).

Tanaka et al., "A novel frizzled gene dentified in human esophageal carcinoma mediates APC/β-catenin signals," *Proc. Natl. Acad. Sci. USA*, vol. 95:10164-10169 (1998).

Terradillos et al., "The hepatitis B virus X gene potentiates c-*myc*-induced liver oncogenesis in transgenic mice," *Oncogene*, vol. 14:395-404 (1997).

Torbenson et al., "Hepatic Adenomas: Analysis of Sex Steroid Receptor Status and the Wnt Signaling Pathway," *Mod. Pathol.*, vol. 15(3):189-196 (2002).

Ueda et al., "Mutations of the β- and γ-catenin genes are uncommon in human lung, breast, kidney, cervical and ovarian carcinomas," *British Journal of Cancer*, vol. 85:64-68 (2001).

Umeda et al., "β-Catenin Mutations Are Absent in Hepatocellular Carcinomas of SV40 T-antigen Transgenic Mice," *Int. J. Oncol.*, vol. 16:1133-1136 (2000).

Van Noort et al., "Wnt Signaling Controls the Phosphorylation Status of β-Catenin," *The Journal of Biological Chemistry*, vol. 277:17901-17905 (2002).

Veeman et al., "Zebrafish Prickle, a Modulator of Noncanonical Wnt/Fz Signaling, Regulates Gastrulation Movements," *Current Biology*, vol. 13:680-685 (2003).

Weeraratna et al., "Wnt5a signaling directly affects cell motility and invasion of metastatic melanoma," *Cancer Cell*, vol. 1:279-288 (2002).

Willert et al., "Wnt proteins are lipid-modified and can act as stem cell growth factors," *Nature*, vol. 423:448-452 (2003).

Wong et al., "β-Catenin Mutation and Overexpression in Hepatocellular Carcinoma: Clinicopathologic and Prognostic Significance," *Cancer*, vol. 92:136-145 (2001).

Yeh et al., "Elevation of Transforming Growth Factor α and Its Relationship to the Epidermal Growth Factor and α-Fetoprotein Levels in Patients with Hepatocellular Carcinoma," *Cancer Research*, vol. 47:896-901 (1987).

Zhang et al., "The Expression of C-MYC-and C-N-Ras in Human Cirrhotic Livers, Hepatocellular Carcinomas and Liver Tissue Surrounding the Tumors," *Oncogene*, vol. 5:909-914 (1990).

Zhang et al., "Deletions of Chromosome 13q, Mutations in *Retinoblastoma 1*, and Retinoblastoma Protein State in Human Hepatocellular Carinoma," *Cancer Research*, vol. 54:4177-4182 (1994).

Zhu et al., "Analysis of Wnt Gene Expression in Prostate Cancer: Mutual Inhibition by WNT11 and the Androgen Receptor," *Cancer Research*, vol. 64:7918-7926 (2004).

Zimonjic et al., "Novel Recurrent Genetic Imbalances in Human Hepatocellular Carcinoma Cell Lines Identified by Comparative Genomic Hybridization," *Hepatology*, vol. 29:1208-1214 (1999).

International Search Report and Written Opinion, mailed Jan. 18, 2007, for corresponding International application No. PCT/US05/01514.

NCBI Protein database Accession No. BAA34668, Feb. 6, 1999.
NCBI Protein database Accession No. NP_003384, Aug. 23, 2004.
NCBI Protein database Accession No. NP_003498, Aug. 23, 2004.
NCBI Protein database Accession No. NP_004617, Aug. 23, 2004.
NCBI Protein database Accession No. NP_032083, Aug. 25, 2004.
NCBI Protein database Accession No. NP_033545, Aug. 25, 2004.
NCBI Protein database Accession No. NP_033547, Aug. 25, 2004.
NCBI Protein database Accession No. NP_035850, Aug. 25, 2004.
NCBI Protein database Accession No. NP_110380, Aug. 23, 2004.
NCBI Protein database Accession No. Q61091, Mar. 15, 2004.
NCBI Protein database Accession No. Q9H461, Sep. 15, 2003.
International Search Report and Written Opinion issued on Jul. 14, 2008 for related International Application No. PCT/US05/00267.

A
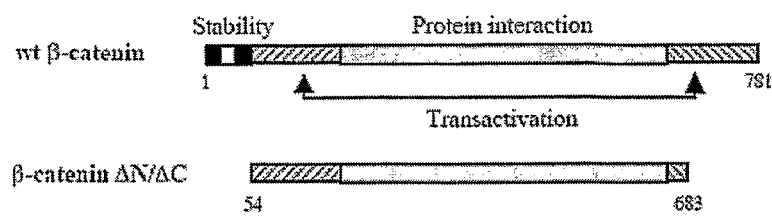
B
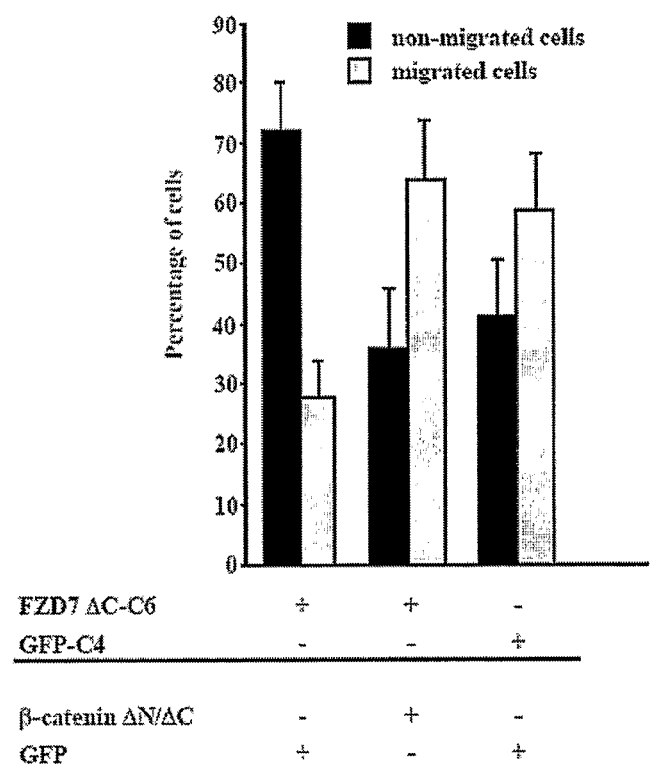
FIG. 6

Human Frizzled 7

Accession: O75084
Protein name: Frizzled 7 [Precursor]
DEFINITION: frizzled 7; Frizzled, drosophila, homolog of, 7; frizzled(Drosophila) homolog 7 [Homo sapiens].
ACCESSION   NP_003498

ORIGIN (574 aa)
MRDPGAAVPL SSLGFCALVL ALLGALSAGA GAQPYHGEKG ISVPDHGFCQ PISIPLCTDI
AYNQTILPNL LGHTNQEDAG LEVHQFYPLV KVQCSPELRF FLCSMYAPVC TVLDQAIPPC
RSLCERARQG CEALMNKFGF QWPERLRCEN FPVHGAGEIC VGQNTSDGSG GPGGGPTAYP
TAPYLPDLPF TALPPGASDG KGRPAFPFSC PRQLKVPPYL GYRFLGERDC GAPCEPGRAN
GLMYFKEEER RFARLWVGVW SVLCCASTLF TVLTYLVDMR RFSYPERPII FLSGCYFMVA
VAHVAGFFLE DRAVCVERFS DDGYRTVAQG TKKEGCTILF MVLYFFGMAS SIWWVILSLT
WFLAAGMKWG HEAIEANSQY FHLAAWAVPA VKTITILAMG QVDGDLLNGV CYVGFSSVDA
LRGFVLAPLF VYFFIGTSFL LAGFVSFFRI RTIMKHDGTK TEKLEKLMVR IGVFSVLYTV
PATIVLACYF YEQAFREHWE RTWLLQTCKS YAVPCPPGHF PPMSPDFTVF MIKCLMTMIV
GITTGFWIWS GKTLQSWRRF YHRLSHSSKG ETAV  (SEQ ID NO:1)

Human Frizzled 7 Putative ligand binding site

\* Cystein-rich domain (CRD)
CQPISIPLCTDIAYNQTILPNLLGHTNQEDAGLEVHQFYPLVKVQCSPELRFFLCSMYAPVCRSLCERARQ
GCEALMNKFGFQWPERLRCENFP (49-152) (SEQ ID NO:2)

Mouse Frizzled 7

Accession: Q61090
Protein name: Frizzled 7 [Precursor]
DEFINITION: frizzled 7 [Mus musculus].
ACCESSION   NP_032083

ORIGIN (572 aa)
MRGPGTAASH SPLGLCALVL ALLGALPTDT RAQPYHGEKG ISVPDHGFCQ PISIPLCTDI
AYNQTILPNL LGHTNQEDAG LEVHQFYPLV KVQCSPELRF FLCSMYAPVC TVLDQAIPPC
RSLCERARQG CEALMNKFGF QWPERLRCEN FPVHGAGEIC VGQNTSDGSG GAGGSPTAYP
TAPYLPDPPF TAMSPSDGRG RLSFPFSCPR QLKVPPYLGY RFLGERDCGA PCEPGRANGL
MYFKEEERRF ARLWVGVWSV LSCASTLFTV LTYLVDMRRF SYPERPIIFL SGCYFMVAVA
HVAGFLLEDR AVCVERFSDD GYRTVAQGTK KEGCTILFMV LYFFGMASSI WWVILSLTWF
LAAGMKWGHE AIEANSQYFH LAAWAVPAVK TITILAMGQV DGDLLSGVCY VGLSSVDALR
GFVLAPLFVY LFIGTSFLLA GFVSLFRIRT IMKHDGTKTE KLEKLMVRIG VFSVLYTVPA
TIVLACYFYE QAFREHWERT WLLQTCKSYA VPCPPRHFSP MSPDFTVFMI KYLMTMIVGI
TTGFWIWSGK TLQSWRRFYH RLSHSSKGET AV(SEQ ID NO:3)

FIG. 8A

Human Frizzled 8

Accession: Q9H461
Protein name: Frizzled 8 [Precursor]

Origin (694 aa)
```
MEWGYLLEVT SLLAALALLQ RSSGAAAASA KELACQEITV PLCKGIGYNY TYMPNQFNHD
TQDEAGLEVH QFWPLVEIQC SPDLKFFLCS MYTPICLEDY KKPLPPCRSV CERAKAGCAP
LMRQYGFAWP DRMRCDRLPE QGNPDTLCMD YNRTDLTTAA PSPPRRLPPP PPGEQPPSGS
GHGRPPGARP PHRGGGRGGG GGDAAAPPAR GGGGGGKARP PGGGAAPCEP GCQCRAPMVS
VSSERHPLYN RVKTGQIANC ALPCHNPFFS QDERAFTVFW IGLWSVLCFV STFATVSTFL
IDMERFKYPE RPIIFLSACY LFVSVGYLVR LVAGHEKVAC SGGAPGAGGA GGAGGAAAGA
GAAGAGAGGP GGRGEYEELG AVEQHVRYET TGPALCTVVF LLVYFFGMAS SIWWVILSLT
WFLAAGMKWG NEAIAGYSQY FHLAAWLVPS VKSIAVLALS SVDGDPVAGI CYVGNQSLDN
LRGFVLAPLV IYLFIGTMFL LAGFVSLFRI RSVIKQQDGP TKTHKLEKLM IRLGLFTVLY
TVPAAVVVAC LFYEQHNRPR WEATHNCPCL RDLQPDQARR PDYAVFMLKY FMCLVVGITS
GVWVWSGKTL ESWRSLCTRC CWASKGAAVG GGAGATAAGG GGGPGGGGGG GPGGGGGPGG
GGGSLYSDVS TGLTWRSGTA SSVSYPKQMP LSQV(SEQ ID NO:4)
```

Human FZD8 Putative ligand binding site
* Cystein-rich domain (CRD)

CQEI<u>TVPLCKGIGYNYTYMPNQFNHDTQDEAGLEVHQFWPLVEIQCSPDLKFFLCSMYTPICLED
YKKPLPPCRSVCERAKAGCAPLMRQYGFAWP</u>DRMRCDRLP (35-139) ((SEQ ID NO:5)

Mouse Frizzled 8

Accession: Q61091
Protein name: Frizzled 8 [Precursor]

Origin (685 aa)
```
MEWGYLLEVT SLLAALAVLQ RSSGAAAASA KELACQEITV PLCKGIGYNY TYMPNQFNHD
TQDEAGLEVH QFWPLVEIQC SPDLKFFLCS MYTPICLEDY KKPLPPCRSV CERAKAGCAP
LMRQYGFAWP DRMRCDRLPE QGNPDTLCMD YNRTDLTTAA PSPPRRLPPP PPPGEQPPSG
SGHSRPPGAR PPHRGGSSRG SGDAAAAPPS RGGKARPPGG GAAPCEPGCQ CRAPMVSVSS
ERHPLYNRVK TGQIANCALP CHNPFFSQDE RAFTVFWIGL WSVLCFVSTF ATVSTFLIDM
ERFKYPERPI IFLSACYLFV SVGYLVRLVA GHEKVACSGG APGAGGRGGA GGAAAGAGA
AGRGASSPGA RGEYEELGAV EQHVRYETTG PALCTVVFLL VYFFGMASSI WWVILSLTWF
LAAGMKWGNE AIAGYSQYFH LAAWLVPSVK SIAVLALSSV DGDPVAGICY VGNQSLDNLR
GFVLAPLVIY LFIGTMFLLA GFVSLFRIRS VIKQQGGPTK THKLEKLMIR LGLFTVLYTV
PAAVVVACLF YEQHNRPRWE ATHNCPCLRD LQPDQARRPD YAVFMLKYFM CLVVGITSGV
WVWSGKTLES WRALCTRCCW ASKGAAVGAG AGGSGPGGSG PGPGGGGHG GGGGSLYSDV
STGLTWRSGT ASSVSYPKQM PLSQV (SEQ ID NO:6)
```

FIG. 8B

Human Wnt3

Accession P56703
Protein name: Wnt-3 proto-oncogene protein [Precursor]
ACCESSION   NP_110380
Definition: wingless-type MMTV integration site family, member 3; WNT-3 proto-oncogene protein precursor [Homo sapiens]

ORIGIN (355 aa)
MEPHLLGLLL GLLLGGTRVL AGYPIWWSLA LGQQYTSLGS QPLLCGSIPG LVPKQLRFCR
NYIEIMPSVA EGVKLGIQEC QHQFRGRRWN CTTIDDSLAI FGPVLDKATR ESAFVHAIAS
AGVAFAVTRS CAEGTSTICG CDSHHKGPPG EGWKWGGCSE DADFGVLVSR EFADARENRP
DARSAMNKHN NEAGRTTILD HMHLKCKCHG LSGSCEVKTC WWAQPDFRAI GDFLKDKYDS
ASEMVVEKHR ESRGWVETLR AKYSLFKPPT ERDLVYYENS PNFCEPNPET GSFGTRDRTC
NVTSHGIDGC DLLCCGRGHN TRTEKRKEKC HCIFHWCCYV SCQECIRIYD VHTCK(SEQ ID NO:7)

Putative binding motifs

Human Wnt3

* Secreted growth factor protein (motif or domain)
1) RESAFVHAIASAGVA (110-124) (SEQ ID NO:8)
2) RSCAEGTSTICGCD (129-142) (SEQ ID NO:9)
3) WKWGGCSEDADFG (153-165) (SEQ ID NO:10)
4) CKCHGLSGSCEVKTCW (206-221) (SEQ ID NO:11)
5) DLVYYENSPNFC (273-284) (SEQ ID NO:12)

Mouse Wnt3

Accession: P17553
Protein name: Wnt-3 proto-oncogene protein [Precursor]
DEFINITION: wingless-related MMTV integration site 3 [Mus musculus].
ACCESSION   NP_033547

ORIGIN (355 aa)
MEPHLLGLLL GLLLSGTRVL AGYPIWWSLA LGQQYTSLAS QPLLCGSIPG LVPKQLRFCR
NYIEIMPSVA EGVKLGIQEC QHQFRGRRWN CTTIDDSLAI FGPVLDKATR ESAFVHAIAS
AGVAFAVTRS CAEGTSTICG CDSHHKGPPG EGWKWGGCSE DADFGVLVSR EFADARENRP
DARSAMNKHN NEAGRTTILD HMHLKCKCHG LSGSCEVKTC WWAQPDFRAI GDFLKDKYDS
ASEMVVEKHR ESRGWVETLR AKYALFKPPT ERDLVYYENS PNFCEPNPET GSFGTRDRTC
NVTSHGIDGC DLLCCGRGHN TRTEKRKEKC HCVFHWCCYV SCQECIRIYD VHTCK(SEQ ID NO:13)

FIG. 8C

Human Wnt8B

Accession: Q93098
Protein name: Wnt-8b protein [Precursor]
DEFINITION: wingless-type MMTV integration site family, member 8B precursor [Homo sapiens].
ACCESSION: NP_003384

ORIGIN (351 aa)
MFLSKPSVYI CLFTCVLQLS HSWSVNNFLM TGPKAYLIYS SSVAAGAQSG IEECKYQFAW
DRWNCPERAL QLSSHGGLRS ANRETAFVHA ISSAGVMYTL TRNCSLGDFD NCGCDDSRNG
QLGGQGWLWG GCSDNVGFGE AISKQFVDAL ETGQDARAAM NLHNNEAGRK AVKGTMKRTC
KCHGVSGSCT TQTCWLQLPE FREVGAHLKE KYHAALKVDL LQGAGNSAAA RGAIADTFRS
ISTRELVHLE DSPDYCLENK TLGLLGTEGR ECLRRGRALG RWELRSCRRL CGDCGLAVEE
RRAETVSSCN CKFHWCCAVR CEQCRRRVTK YFCSRAERPR GGAAHKPGRK P (SEQ ID NO:14)

Putative binding motifs

Human Wnt8b

* Secreted growth factor protein (motif or domain)
1) RETAFVHAISSAGVM (83-97) (SEQ ID NO:15)
2) RNCSLGDFDNCGCD (102-115) (SEQ ID NO:16)
3) WLWGGCSDNVGFG (127-139) (SEQ ID NO:17)
4) CKCHGVSGSCTTQTCW (180-195) (SEQ ID NO:18)
5) ELVHLEDSPDYC (245-256) (SEQ ID NO:19)

Mouse Wnt8B

Accession: Q9WUD6
Protein name: Wnt-8b protein [Precursor]
DEFINITION: wingless related MMTV integration site 8b [Mus musculus].
ACCESSION NP_035850

ORIGIN (350 aa)
MFLMKPVCVL LVTCVLHRSH AWSVNNFLMT GPKAYLVYSS SVAAGAQSGI EECKYQFAWD
RWNCPERALQ LSSHGGLRSA NRETAFVHAI SSAGVMYTLT RNCSLGDFDN CGCDDSRNGQ
LGGQGWLWGG CSDNVGFGEA ISKQFVDALE TGQDARAAMN LHNNEAGRKA VKGTMKRTCK
CHGVSGSCTT QTCWLQLPEF REVGAHLKEK YHAALKVDLL QGAGNSAAGR GAIADTFRSI
STRELVHLED SPDYCLENKT LGLLGTEGRE CLRRGRALGR WERRSCRRLC GDCGLAVEER
RAETVSSCNC KFHWCCAVRC EQCRRRVTKY FCSRAERPPR GAAHKPGKNS (SEQ ID NO:20)

FIG. 8D

Human Wnt 11

Accession: O96014
Protein name: Wnt-11 protein [Precursor]
DEFINITION: wingless-type MMTV integration site family, member 11 precursor [Homo sapiens]
ACCESSION    NP_004617

ORIGIN (354 aa)
MRARPQVCEA LLFALALQTG VCYGIKWLAL SKTPSALALN QTQHCKQLEG LVSAQVQLCR
SNLELMHTVV HAAREVMKAC RRAFADMRWN CSSIELAPNY LLDLERGTRE SAFVYALSAA
AISHAIARAC TSGDLPGCSC GPVPGEPPGP GNRWGGCADN LSYGLLMGAK FSDAPMKVKK
TGSQANKLMR LHNSEVGRQA LRASLEMKCK CHGVSGSCSI RTCWKGLQEL QDVAADLKTR
YLSATKVVHR PMGTRKHLVP KDLDIRPVKD SELVYLQSSP DFCMKNEKVG SHGTQDRQCN
KTSNGSDSCD LMCCGRGYNP YTDRVVERCH CKYHWCCYVT CRRCERTVER YVCK (SEQ ID NO:21)

Putative binding motifs

Human Wnt11

* Secreted growth factor protein (motif or domain)
    1) RESAFVYALSAAAIS (109-123) (SEQ ID NO:22)
    2) RACTSGDLPGCSCG (128-141) (SEQ ID NO:23)
    3) NRWGGCADNLSYG (152-164) (SEQ ID NO:24)
    4) CKCHGVSGSCSIRTCW (209-224) (SEQ ID NO:25)
    5) ELVYLQSSPDFC (272-283) (SEQ ID NO:26)

Mouse Wnt 11

Accession: P48615
Protein name: Wnt-11 protein [Precursor]
DEFINITION: wingless-related MMTV integration site 11 [Mus musculus].
ACCESSION    NP_033545

ORIGIN (354 aa)
MRARPQVCEA LLFALALHTG VCYGIKWLAL SKTPAALALN QTQHCKQLEG LVSAQVQLCR
SNLELMRTIV HAARGAMKAC RRAFADMRWN CSSIELAPNY LLDLERGTRE SAFVYALSAA
TISHTIARAC TSGDLPGCSC GPVPGEPPGP GNRWGGCADN LSYGLLMGAK FSDAPMKVKK
TGSQANKLMR LHNSEVGRQA LRASLETKCK CHGVSGSCSI RTCWKGLQEL QDVAADLKTR
YLSATKVVHR PMGTRKHLVP KDLDIRPVKD SELVYLQSSP DFCMKNEKVG SHGTQDRQCN
KTSNGSDSCD LMCCGRGYNP YTDRVVERCH CKYHWCCYVT CRRCERTVER YVCK (SEQ ID NO:27)

FIG. 8E

SEQUENCE LISTING

```
<160> NUMBER OF SEQ ID NOS: 59

<210> SEQ ID NO 1
<211> LENGTH: 574
<212> TYPE: PRT
<213> ORGANISM: Homo sapiens

<400> SEQUENCE: 1

Met Arg Asp Pro Gly Ala Ala Val Pro Leu Ser Ser Leu Gly Phe Cys
1               5                   10                  15

Ala Leu Val Leu Ala Leu Leu Gly Ala Leu Ser Ala Gly Ala Gly Ala
            20                  25                  30

Gln Pro Tyr His Gly Glu Lys Gly Ile Ser Val Pro Asp His Gly Phe
```

-continued

```
                35                  40                  45
Cys Gln Pro Ile Ser Ile Pro Leu Cys Thr Asp Ile Ala Tyr Asn Gln
 50                  55                  60

Thr Ile Leu Pro Asn Leu Leu Gly His Thr Asn Gln Glu Asp Ala Gly
 65                  70                  75                  80

Leu Glu Val His Gln Phe Tyr Pro Leu Val Lys Val Gln Cys Ser Pro
                 85                  90                  95

Glu Leu Arg Phe Phe Leu Cys Ser Met Tyr Ala Pro Val Cys Thr Val
                100                 105                 110

Leu Asp Gln Ala Ile Pro Pro Cys Arg Ser Leu Cys Glu Arg Ala Arg
                115                 120                 125

Gln Gly Cys Glu Ala Leu Met Asn Lys Phe Gly Phe Gln Trp Pro Glu
130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Pro Gly Gly Gly Pro
                165                 170                 175

Thr Ala Tyr Pro Thr Ala Pro Tyr Leu Pro Asp Leu Pro Phe Thr Ala
                180                 185                 190

Leu Pro Pro Gly Ala Ser Asp Gly Lys Gly Arg Pro Ala Phe Pro Phe
                195                 200                 205

Ser Cys Pro Arg Gln Leu Lys Val Pro Pro Tyr Leu Gly Tyr Arg Phe
210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu Trp
                245                 250                 255

Val Gly Val Trp Ser Val Leu Cys Cys Ala Ser Thr Leu Phe Thr Val
                260                 265                 270

Leu Thr Tyr Leu Val Asp Met Arg Arg Phe Ser Tyr Pro Glu Arg Pro
                275                 280                 285

Ile Ile Phe Leu Ser Gly Cys Tyr Phe Met Val Ala Val Ala His Val
290                 295                 300

Ala Gly Phe Phe Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
                325                 330                 335

Thr Ile Leu Phe Met Val Leu Tyr Phe Phe Gly Met Ala Ser Ser Ile
                340                 345                 350

Trp Trp Val Ile Leu Ser Leu Thr Trp Phe Leu Ala Ala Gly Met Lys
                355                 360                 365

Trp Gly His Glu Ala Ile Glu Ala Asn Ser Gln Tyr Phe His Leu Ala
                370                 375                 380

Ala Trp Ala Val Pro Ala Val Lys Thr Ile Thr Ile Leu Ala Met Gly
385                 390                 395                 400

Gln Val Asp Gly Asp Leu Leu Asn Gly Val Cys Tyr Val Gly Phe Ser
                405                 410                 415

Ser Val Asp Ala Leu Arg Gly Phe Val Leu Ala Pro Leu Phe Val Tyr
                420                 425                 430

Phe Phe Ile Gly Thr Ser Phe Leu Leu Ala Gly Phe Val Ser Phe Phe
                435                 440                 445

Arg Ile Arg Thr Ile Met Lys His Asp Gly Thr Lys Thr Glu Lys Leu
450                 455                 460
```

```
Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
                485                 490                 495

Glu His Trp Glu Arg Thr Trp Leu Leu Gln Thr Cys Lys Ser Tyr Ala
            500                 505                 510

Val Pro Cys Pro Gly His Phe Pro Pro Met Ser Pro Asp Phe Thr
        515                 520                 525

Val Phe Met Ile Lys Cys Leu Met Thr Met Ile Val Gly Ile Thr Thr
    530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
                565                 570

<210> SEQ ID NO 2
<211> LENGTH: 94
<212> TYPE: PRT
<213> ORGANISM: Homo sapiens

<400> SEQUENCE: 2

Cys Gln Pro Ile Ser Ile Pro Leu Cys Thr Asp Ile Ala Tyr Asn Gln
1               5                   10                  15

Thr Ile Leu Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Arg Ser
    50                  55                  60

Leu Cys Glu Arg Ala Arg Gln Gly Cys Glu Ala Leu Met Asn Lys Phe
65                  70                  75                  80

Gly Phe Gln Trp Pro Glu Arg Leu Arg Cys Glu Asn Phe Pro
                85                  90

<210> SEQ ID NO 3
<211> LENGTH: 572
<212> TYPE: PRT
<213> ORGANISM: Mus musculus

<400> SEQUENCE: 3

Met Arg Gly Pro Gly Thr Ala Ala Ser His Ser Pro Leu Gly Leu Cys
1               5                   10                  15

Ala Leu Val Leu Ala Leu Leu Gly Ala Leu Pro Thr Asp Thr Arg Ala
            20                  25                  30

Gln Pro Tyr His Gly Glu Lys Gly Ile Ser Val Pro Asp His Gly Phe
        35                  40                  45

Cys Gln Pro Ile Ser Ile Pro Leu Cys Thr Asp Ile Ala Tyr Asn Gln
    50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125
```

```
Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Ala Gly Gly Ser Pro
            165                 170                 175

Thr Ala Tyr Pro Thr Ala Pro Tyr Leu Pro Asp Pro Pro Phe Thr Ala
            180                 185                 190

Met Ser Pro Ser Asp Gly Arg Gly Arg Leu Ser Phe Pro Ser Cys
        195                 200                 205

Pro Arg Gln Leu Lys Val Pro Pro Tyr Leu Gly Tyr Arg Phe Leu Gly
    210                 215                 220

Glu Arg Asp Cys Gly Ala Pro Cys Glu Pro Gly Arg Ala Asn Gly Leu
225                 230                 235                 240

Met Tyr Phe Lys Glu Glu Glu Arg Arg Phe Ala Arg Leu Trp Val Gly
                245                 250                 255

Val Trp Ser Val Leu Ser Cys Ala Ser Thr Leu Phe Thr Val Leu Thr
        260                 265                 270

Tyr Leu Val Asp Met Arg Arg Phe Ser Tyr Pro Glu Arg Pro Ile Ile
    275                 280                 285

Phe Leu Ser Gly Cys Tyr Phe Met Val Ala Val Ala His Val Ala Gly
    290                 295                 300

Phe Leu Leu Glu Asp Arg Ala Val Cys Val Glu Arg Phe Ser Asp Asp
305                 310                 315                 320

Gly Tyr Arg Thr Val Ala Gln Gly Thr Lys Lys Glu Gly Cys Thr Ile
            325                 330                 335

Leu Phe Met Val Leu Tyr Phe Phe Gly Met Ala Ser Ser Ile Trp Trp
        340                 345                 350

Val Ile Leu Ser Leu Thr Trp Phe Leu Ala Ala Gly Met Lys Trp Gly
        355                 360                 365

His Glu Ala Ile Glu Ala Asn Ser Gln Tyr Phe His Leu Ala Ala Trp
    370                 375                 380

Ala Val Pro Ala Val Lys Thr Ile Thr Ile Leu Ala Met Gly Gln Val
385                 390                 395                 400

Asp Gly Asp Leu Leu Ser Gly Val Cys Tyr Val Gly Leu Ser Ser Val
                405                 410                 415

Asp Ala Leu Arg Gly Phe Val Leu Ala Pro Leu Phe Val Tyr Leu Phe
            420                 425                 430

Ile Gly Thr Ser Phe Leu Leu Ala Gly Phe Val Ser Leu Phe Arg Ile
        435                 440                 445

Arg Thr Ile Met Lys His Asp Gly Thr Lys Thr Glu Lys Leu Glu Lys
    450                 455                 460

Leu Met Val Arg Ile Gly Val Phe Ser Val Leu Tyr Thr Val Pro Ala
465                 470                 475                 480

Thr Ile Val Leu Ala Cys Tyr Phe Tyr Glu Gln Ala Phe Arg Glu His
            485                 490                 495

Trp Glu Arg Thr Trp Leu Leu Gln Thr Cys Lys Ser Tyr Ala Val Pro
            500                 505                 510

Cys Pro Pro Arg His Phe Ser Pro Met Ser Pro Asp Phe Thr Val Phe
        515                 520                 525

Met Ile Lys Tyr Leu Met Thr Met Ile Val Gly Ile Thr Thr Gly Phe
    530                 535                 540
```

-continued

Trp Ile Trp Ser Gly Lys Thr Leu Gln Ser Trp Arg Arg Phe Tyr His
545                 550                 555                 560

Arg Leu Ser His Ser Ser Lys Gly Glu Thr Ala Val
                565                 570

<210> SEQ ID NO 4
<211> LENGTH: 694
<212> TYPE: PRT
<213> ORGANISM: Homo sapiens

<400> SEQUENCE: 4

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
50              55                  60

Ala Gly Leu Glu Val His Gln Phe Trp Pro Leu Val Glu Ile Gln Cys
65              70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
        195                 200                 205

Ala Arg Gly Gly Gly Gly Gly Lys Ala Arg Pro Pro Gly Gly Gly
        210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr Val Phe Trp Ile Gly Leu Trp Ser Val Leu Cys
            275                 280                 285

Phe Val Ser Thr Phe Ala Thr Val Ser Thr Phe Leu Ile Asp Met Glu
        290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Gly Ala Gly Gly
            340                 345                 350

Ala Gly Gly Ala Ala Ala Gly Ala Gly Ala Gly Ala Gly
         355                 360                 365

Gly Pro Gly Gly Arg Gly Glu Tyr Glu Glu Leu Gly Ala Val Glu Gln
370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ile Trp Trp Val Ile
             405                 410                 415

Leu Ser Leu Thr Trp Phe Leu Ala Ala Gly Met Lys Trp Gly Asn Glu
             420                 425                 430

Ala Ile Ala Gly Tyr Ser Gln Tyr Phe His Leu Ala Ala Trp Leu Val
             435                 440                 445

Pro Ser Val Lys Ser Ile Ala Val Leu Ala Leu Ser Ser Val Asp Gly
             450                 455                 460

Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
             485                 490                 495

Thr Met Phe Leu Leu Ala Gly Phe Val Ser Leu Phe Arg Ile Arg Ser
             500                 505                 510

Val Ile Lys Gln Gln Asp Gly Pro Thr Lys Thr His Lys Leu Glu Lys
             515                 520                 525

Leu Met Ile Arg Leu Gly Leu Phe Thr Val Leu Tyr Thr Val Pro Ala
             530                 535                 540

Ala Val Val Val Ala Cys Leu Phe Tyr Glu Gln His Asn Arg Pro Arg
545                 550                 555                 560

Trp Glu Ala Thr His Asn Cys Pro Cys Leu Arg Asp Leu Gln Pro Asp
             565                 570                 575

Gln Ala Arg Arg Pro Asp Tyr Ala Val Phe Met Leu Lys Tyr Phe Met
             580                 585                 590

Cys Leu Val Val Gly Ile Thr Ser Gly Val Trp Val Trp Ser Gly Lys
             595                 600                 605

Thr Leu Glu Ser Trp Arg Ser Leu Cys Thr Arg Cys Cys Trp Ala Ser
610                 615                 620

Lys Gly Ala Ala Val Gly Gly Ala Gly Ala Thr Ala Ala Gly Gly
625                 630                 635                 640

Gly Gly Gly Pro Gly Gly Gly Gly Gly Pro Gly Gly Gly
             645                 650                 655

Gly Pro Gly Gly Gly Gly Ser Leu Tyr Ser Asp Val Ser Thr Gly
             660                 665                 670

Leu Thr Trp Arg Ser Gly Thr Ala Ser Ser Val Ser Tyr Pro Lys Gln
             675                 680                 685

Met Pro Leu Ser Gln Val
    690

<210> SEQ ID NO 5
<211> LENGTH: 105
<212> TYPE: PRT
<213> ORGANISM: Homo sapiens

<400> SEQUENCE: 5

Cys Gln Glu Ile Thr Val Pro Leu Cys Lys Gly Ile Gly Tyr Asn Tyr
1               5                   10                  15

Thr Tyr Met Pro Asn Gln Phe Asn His Asp Thr Gln Asp Glu Ala Gly

-continued

```
                    20                  25                  30
Leu Glu Val His Gln Phe Trp Pro Leu Val Glu Ile Gln Cys Ser Pro
                35                  40                  45

Asp Leu Lys Phe Phe Leu Cys Ser Met Tyr Thr Pro Ile Cys Leu Glu
 50                  55                  60

Asp Tyr Lys Lys Pro Leu Pro Pro Cys Arg Ser Val Cys Glu Arg Ala
 65                  70                  75                  80

Lys Ala Gly Cys Ala Pro Leu Met Arg Gln Tyr Gly Phe Ala Trp Pro
                 85                  90                  95

Asp Arg Met Arg Cys Asp Arg Leu Pro
                100                 105

<210> SEQ ID NO 6
<211> LENGTH: 685
<212> TYPE: PRT
<213> ORGANISM: Mus musculus

<400> SEQUENCE: 6

Met Glu Trp Gly Tyr Leu Leu Glu Val Thr Ser Leu Leu Ala Ala Leu
 1               5                  10                  15

Ala Val Leu Gln Arg Ser Ser Gly Ala Ala Ala Ser Ala Lys Glu
                 20                  25                  30

Leu Ala Cys Gln Glu Ile Thr Val Pro Leu Cys Lys Gly Ile Gly Tyr
                 35                  40                  45

Asn Tyr Thr Tyr Met Pro Asn Gln Phe Asn His Asp Thr Gln Asp Glu
 50                  55                  60

Ala Gly Leu Glu Val His Gln Phe Trp Pro Leu Val Glu Ile Gln Cys
 65                  70                  75                  80

Ser Pro Asp Leu Lys Phe Phe Leu Cys Ser Met Tyr Thr Pro Ile Cys
                 85                  90                  95

Leu Glu Asp Tyr Lys Lys Pro Leu Pro Pro Cys Arg Ser Val Cys Glu
                100                 105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Pro Gly Glu Gln
                165                 170                 175

Pro Pro Ser Gly Ser Gly His Ser Arg Pro Pro Gly Ala Arg Pro Pro
            180                 185                 190

His Arg Gly Gly Ser Ser Arg Gly Ser Gly Asp Ala Ala Ala Ala Pro
            195                 200                 205

Pro Ser Arg Gly Gly Lys Ala Arg Pro Gly Gly Gly Ala Ala Pro
            210                 215                 220

Cys Glu Pro Gly Cys Gln Cys Arg Ala Pro Met Val Ser Val Ser Ser
225                 230                 235                 240

Glu Arg His Pro Leu Tyr Asn Arg Val Lys Thr Gly Gln Ile Ala Asn
                245                 250                 255

Cys Ala Leu Pro Cys His Asn Pro Phe Phe Ser Gln Asp Glu Arg Ala
            260                 265                 270

Phe Thr Val Phe Trp Ile Gly Leu Trp Ser Val Leu Cys Phe Val Ser
            275                 280                 285
```

```
Thr Phe Ala Thr Val Ser Thr Phe Leu Ile Asp Met Glu Arg Phe Lys
    290                 295                 300

Tyr Pro Glu Arg Pro Ile Ile Phe Leu Ser Ala Cys Tyr Leu Phe Val
305                 310                 315                 320

Ser Val Gly Tyr Leu Val Arg Leu Val Ala Gly His Glu Lys Val Ala
                325                 330                 335

Cys Ser Gly Gly Ala Pro Gly Ala Gly Arg Gly Gly Ala Gly Gly
            340                 345                 350

Ala Ala Ala Ala Gly Ala Gly Ala Ala Gly Arg Gly Ala Ser Ser Pro
            355                 360                 365

Gly Ala Arg Gly Glu Tyr Glu Glu Leu Gly Ala Val Glu Gln His Val
370                 375                 380

Arg Tyr Glu Thr Thr Gly Pro Ala Leu Cys Thr Val Val Phe Leu Leu
385                 390                 395                 400

Val Tyr Phe Phe Gly Met Ala Ser Ser Ile Trp Trp Val Ile Leu Ser
                405                 410                 415

Leu Thr Trp Phe Leu Ala Ala Gly Met Lys Trp Gly Asn Glu Ala Ile
                420                 425                 430

Ala Gly Tyr Ser Gln Tyr Phe His Leu Ala Ala Trp Leu Val Pro Ser
                435                 440                 445

Val Lys Ser Ile Ala Val Leu Ala Leu Ser Ser Val Asp Gly Asp Pro
450                 455                 460

Val Ala Gly Ile Cys Tyr Val Gly Asn Gln Ser Leu Asp Asn Leu Arg
465                 470                 475                 480

Gly Phe Val Leu Ala Pro Leu Val Ile Tyr Leu Phe Ile Gly Thr Met
                485                 490                 495

Phe Leu Leu Ala Gly Phe Val Ser Leu Phe Arg Ile Arg Ser Val Ile
            500                 505                 510

Lys Gln Gln Gly Gly Pro Thr Lys Thr His Lys Leu Glu Lys Leu Met
            515                 520                 525

Ile Arg Leu Gly Leu Phe Thr Val Leu Tyr Thr Val Pro Ala Ala Val
            530                 535                 540

Val Val Ala Cys Leu Phe Tyr Glu Gln His Asn Arg Pro Arg Trp Glu
545                 550                 555                 560

Ala Thr His Asn Cys Pro Cys Leu Arg Asp Leu Gln Pro Asp Gln Ala
                565                 570                 575

Arg Arg Pro Asp Tyr Ala Val Phe Met Leu Lys Tyr Phe Met Cys Leu
            580                 585                 590

Val Val Gly Ile Thr Ser Gly Val Trp Val Trp Ser Gly Lys Thr Leu
            595                 600                 605

Glu Ser Trp Arg Ala Leu Cys Thr Arg Cys Cys Trp Ala Ser Lys Gly
610                 615                 620

Ala Ala Val Gly Ala Gly Ala Gly Gly Ser Gly Pro Gly Gly Ser Gly
625                 630                 635                 640

Pro Gly Pro Gly Gly Gly Gly His Gly Gly Gly Gly Ser Leu
                645                 650                 655

Tyr Ser Asp Val Ser Thr Gly Leu Thr Trp Arg Ser Gly Thr Ala Ser
            660                 665                 670

Ser Val Ser Tyr Pro Lys Gln Met Pro Leu Ser Gln Val
            675                 680                 685

<210> SEQ ID NO 7
<211> LENGTH: 355
<212> TYPE: PRT
```

<213> ORGANISM: Homo sapiens

<400> SEQUENCE: 7

```
Met Glu Pro His Leu Leu Gly Leu Leu Leu Gly Leu Leu Leu Gly Gly
1               5                   10                  15

Thr Arg Val Leu Ala Gly Tyr Pro Ile Trp Trp Ser Leu Ala Leu Gly
            20                  25                  30

Gln Gln Tyr Thr Ser Leu Gly Ser Gln Pro Leu Leu Cys Gly Ser Ile
        35                  40                  45

Pro Gly Leu Val Pro Lys Gln Leu Arg Phe Cys Arg Asn Tyr Ile Glu
    50                  55                  60

Ile Met Pro Ser Val Ala Glu Gly Val Lys Leu Gly Ile Gln Glu Cys
65                  70                  75                  80

Gln His Gln Phe Arg Gly Arg Arg Trp Asn Cys Thr Thr Ile Asp Asp
                85                  90                  95

Ser Leu Ala Ile Phe Gly Pro Val Leu Asp Lys Ala Thr Arg Glu Ser
            100                 105                 110

Ala Phe Val His Ala Ile Ala Ser Ala Gly Val Ala Phe Ala Val Thr
        115                 120                 125

Arg Ser Cys Ala Glu Gly Thr Ser Thr Ile Cys Gly Cys Asp Ser His
    130                 135                 140

His Lys Gly Pro Pro Gly Glu Gly Trp Lys Trp Gly Gly Cys Ser Glu
145                 150                 155                 160

Asp Ala Asp Phe Gly Val Leu Val Ser Arg Glu Phe Ala Asp Ala Arg
                165                 170                 175

Glu Asn Arg Pro Asp Ala Arg Ser Ala Met Asn Lys His Asn Asn Glu
            180                 185                 190

Ala Gly Arg Thr Thr Ile Leu Asp His Met His Leu Lys Cys Lys Cys
        195                 200                 205

His Gly Leu Ser Gly Ser Cys Glu Val Lys Thr Cys Trp Trp Ala Gln
    210                 215                 220

Pro Asp Phe Arg Ala Ile Gly Asp Phe Leu Lys Asp Lys Tyr Asp Ser
225                 230                 235                 240

Ala Ser Glu Met Val Val Glu Lys His Arg Glu Ser Arg Gly Trp Val
                245                 250                 255

Glu Thr Leu Arg Ala Lys Tyr Ser Leu Phe Lys Pro Pro Thr Glu Arg
            260                 265                 270

Asp Leu Val Tyr Tyr Glu Asn Ser Pro Asn Phe Cys Glu Pro Asn Pro
        275                 280                 285

Glu Thr Gly Ser Phe Gly Thr Arg Asp Arg Thr Cys Asn Val Thr Ser
    290                 295                 300

His Gly Ile Asp Gly Cys Asp Leu Leu Cys Cys Gly Arg Gly His Asn
305                 310                 315                 320

Thr Arg Thr Glu Lys Arg Lys Glu Lys Cys His Cys Ile Phe His Trp
                325                 330                 335

Cys Cys Tyr Val Ser Cys Gln Glu Cys Ile Arg Ile Tyr Asp Val His
            340                 345                 350

Thr Cys Lys
        355
```

<210> SEQ ID NO 8
<211> LENGTH: 15
<212> TYPE: PRT
<213> ORGANISM: Homo sapiens

-continued

<400> SEQUENCE: 8

Arg Glu Ser Ala Phe Val His Ala Ile Ala Ser Ala Gly Val Ala
1               5                   10                  15

<210> SEQ ID NO 9
<211> LENGTH: 14
<212> TYPE: PRT
<213> ORGANISM: Homo sapiens

<400> SEQUENCE: 9

Arg Ser Cys Ala Glu Gly Thr Ser Thr Ile Cys Gly Cys Asp
1               5                   10

<210> SEQ ID NO 10
<211> LENGTH: 13
<212> TYPE: PRT
<213> ORGANISM: Homo sapiens

<400> SEQUENCE: 10

Trp Lys Trp Gly Gly Cys Ser Glu Asp Ala Asp Phe Gly
1               5                   10

<210> SEQ ID NO 11
<211> LENGTH: 16
<212> TYPE: PRT
<213> ORGANISM: Homo sapiens

<400> SEQUENCE: 11

Cys Lys Cys His Gly Leu Ser Gly Ser Cys Glu Val Lys Thr Cys Trp
1               5                   10                  15

<210> SEQ ID NO 12
<211> LENGTH: 12
<212> TYPE: PRT
<213> ORGANISM: Homo sapiens

<400> SEQUENCE: 12

Asp Leu Val Tyr Tyr Glu Asn Ser Pro Asn Phe Cys
1               5                   10

<210> SEQ ID NO 13
<211> LENGTH: 355
<212> TYPE: PRT
<213> ORGANISM: Mus musculus

<400> SEQUENCE: 13

Met Glu Pro His Leu Leu Gly Leu Leu Leu Gly Leu Leu Ser Gly
1               5                   10                  15

Thr Arg Val Leu Ala Gly Tyr Pro Ile Trp Trp Ser Leu Ala Leu Gly
            20                  25                  30

Gln Gln Tyr Thr Ser Leu Ala Ser Gln Pro Leu Leu Cys Gly Ser Ile
        35                  40                  45

Pro Gly Leu Val Pro Lys Gln Leu Arg Phe Cys Arg Asn Tyr Ile Glu
    50                  55                  60

Ile Met Pro Ser Val Ala Glu Gly Val Lys Leu Gly Ile Gln Glu Cys
65                  70                  75                  80

Gln His Gln Phe Arg Gly Arg Arg Trp Asn Cys Thr Thr Ile Asp Asp
                85                  90                  95

Ser Leu Ala Ile Phe Gly Pro Val Leu Asp Lys Ala Thr Arg Glu Ser
                100                 105                 110

Ala Phe Val His Ala Ile Ala Ser Ala Gly Val Ala Phe Ala Val Thr

```
                 115                 120                 125

Arg Ser Cys Ala Glu Gly Thr Ser Thr Ile Cys Gly Cys Asp Ser His
    130                 135                 140

His Lys Gly Pro Pro Gly Glu Gly Trp Lys Trp Gly Gly Cys Ser Glu
145                 150                 155                 160

Asp Ala Asp Phe Gly Val Leu Val Ser Arg Glu Phe Ala Asp Ala Arg
                165                 170                 175

Glu Asn Arg Pro Asp Ala Arg Ser Ala Met Asn Lys His Asn Asn Glu
            180                 185                 190

Ala Gly Arg Thr Thr Ile Leu Asp His Met His Leu Lys Cys Lys Cys
        195                 200                 205

His Gly Leu Ser Gly Ser Cys Glu Val Lys Thr Cys Trp Trp Ala Gln
    210                 215                 220

Pro Asp Phe Arg Ala Ile Gly Asp Phe Leu Lys Asp Lys Tyr Asp Ser
225                 230                 235                 240

Ala Ser Glu Met Val Val Glu Lys His Arg Glu Ser Arg Gly Trp Val
                245                 250                 255

Glu Thr Leu Arg Ala Lys Tyr Ala Leu Phe Lys Pro Pro Thr Glu Arg
            260                 265                 270

Asp Leu Val Tyr Tyr Glu Asn Ser Pro Asn Phe Cys Glu Pro Asn Pro
        275                 280                 285

Glu Thr Gly Ser Phe Gly Thr Arg Asp Arg Thr Cys Asn Val Thr Ser
    290                 295                 300

His Gly Ile Asp Gly Cys Asp Leu Leu Cys Cys Gly Arg Gly His Asn
305                 310                 315                 320

Thr Arg Thr Glu Lys Arg Lys Glu Lys Cys His Cys Val Phe His Trp
                325                 330                 335

Cys Cys Tyr Val Ser Cys Gln Glu Cys Ile Arg Ile Tyr Asp Val His
            340                 345                 350

Thr Cys Lys
        355

<210> SEQ ID NO 14
<211> LENGTH: 351
<212> TYPE: PRT
<213> ORGANISM: Homo sapiens

<400> SEQUENCE: 14

Met Phe Leu Ser Lys Pro Ser Val Tyr Ile Cys Leu Phe Thr Cys Val
1               5                   10                  15

Leu Gln Leu Ser His Ser Trp Ser Val Asn Asn Phe Leu Met Thr Gly
            20                  25                  30

Pro Lys Ala Tyr Leu Ile Tyr Ser Ser Val Ala Ala Gly Ala Gln
        35                  40                  45

Ser Gly Ile Glu Glu Cys Lys Tyr Gln Phe Ala Trp Asp Arg Trp Asn
    50                  55                  60

Cys Pro Glu Arg Ala Leu Gln Leu Ser Ser His Gly Gly Leu Arg Ser
65                  70                  75                  80

Ala Asn Arg Glu Thr Ala Phe Val His Ala Ile Ser Ser Ala Gly Val
                85                  90                  95

Met Tyr Thr Leu Thr Arg Asn Cys Ser Leu Gly Asp Phe Asp Asn Cys
            100                 105                 110

Gly Cys Asp Asp Ser Arg Asn Gly Gln Leu Gly Gly Gln Gly Trp Leu
        115                 120                 125
```

```
Trp Gly Gly Cys Ser Asp Asn Val Gly Phe Gly Glu Ala Ile Ser Lys
        130                 135                 140

Gln Phe Val Asp Ala Leu Glu Thr Gly Gln Asp Ala Arg Ala Ala Met
145                 150                 155                 160

Asn Leu His Asn Asn Glu Ala Gly Arg Lys Ala Val Lys Gly Thr Met
                165                 170                 175

Lys Arg Thr Cys Lys Cys His Gly Val Ser Gly Ser Cys Thr Thr Gln
            180                 185                 190

Thr Cys Trp Leu Gln Leu Pro Glu Phe Arg Glu Val Gly Ala His Leu
        195                 200                 205

Lys Glu Lys Tyr His Ala Ala Leu Lys Val Asp Leu Leu Gln Gly Ala
210                 215                 220

Gly Asn Ser Ala Ala Arg Gly Ala Ile Ala Asp Thr Phe Arg Ser
225                 230                 235                 240

Ile Ser Thr Arg Glu Leu Val His Leu Glu Asp Ser Pro Asp Tyr Cys
                245                 250                 255

Leu Glu Asn Lys Thr Leu Gly Leu Leu Gly Thr Gly Arg Glu Cys
            260                 265                 270

Leu Arg Arg Gly Arg Ala Leu Gly Arg Trp Glu Leu Arg Ser Cys Arg
        275                 280                 285

Arg Leu Cys Gly Asp Cys Gly Leu Ala Val Glu Glu Arg Arg Ala Glu
290                 295                 300

Thr Val Ser Ser Cys Asn Cys Lys Phe His Trp Cys Cys Ala Val Arg
305                 310                 315                 320

Cys Glu Gln Cys Arg Arg Val Thr Lys Tyr Phe Cys Ser Arg Ala
                325                 330                 335

Glu Arg Pro Arg Gly Gly Ala Ala His Lys Pro Gly Arg Lys Pro
                340                 345                 350

<210> SEQ ID NO 15
<211> LENGTH: 15
<212> TYPE: PRT
<213> ORGANISM: Homo sapiens

<400> SEQUENCE: 15

Arg Glu Thr Ala Phe Val His Ala Ile Ser Ser Ala Gly Val Met
1               5                   10                  15

<210> SEQ ID NO 16
<211> LENGTH: 14
<212> TYPE: PRT
<213> ORGANISM: Homo sapiens

<400> SEQUENCE: 16

Arg Asn Cys Ser Leu Gly Asp Phe Asp Asn Cys Gly Cys Asp
1               5                   10

<210> SEQ ID NO 17
<211> LENGTH: 13
<212> TYPE: PRT
<213> ORGANISM: Homo sapiens

<400> SEQUENCE: 17

Trp Leu Trp Gly Gly Cys Ser Asp Asn Val Gly Phe Gly
1               5                   10

<210> SEQ ID NO 18
<211> LENGTH: 16
<212> TYPE: PRT
```

<213> ORGANISM: Homo sapiens

<400> SEQUENCE: 18

Cys Lys Cys His Gly Val Ser Gly Ser Cys Thr Thr Gln Thr Cys Trp
1               5                   10                  15

<210> SEQ ID NO 19
<211> LENGTH: 12
<212> TYPE: PRT
<213> ORGANISM: Homo sapiens

<400> SEQUENCE: 19

Glu Leu Val His Leu Glu Asp Ser Pro Asp Tyr Cys
1               5                   10

<210> SEQ ID NO 20
<211> LENGTH: 350
<212> TYPE: PRT
<213> ORGANISM: Mus musculus

<400> SEQUENCE: 20

Met Phe Leu Met Lys Pro Val Cys Val Leu Val Thr Cys Val Leu
1               5                   10                  15

His Arg Ser His Ala Trp Ser Val Asn Asn Phe Leu Met Thr Gly Pro
                20                  25                  30

Lys Ala Tyr Leu Val Tyr Ser Ser Val Ala Ala Gly Ala Gln Ser
            35                  40                  45

Gly Ile Glu Glu Cys Lys Tyr Gln Phe Ala Trp Asp Arg Trp Asn Cys
50                  55                  60

Pro Glu Arg Ala Leu Gln Leu Ser Ser His Gly Gly Leu Arg Ser Ala
65                  70                  75                  80

Asn Arg Glu Thr Ala Phe Val His Ala Ile Ser Ser Ala Gly Val Met
                85                  90                  95

Tyr Thr Leu Thr Arg Asn Cys Ser Leu Gly Asp Phe Asn Cys Gly
            100                 105                 110

Cys Asp Asp Ser Arg Asn Gly Gln Leu Gly Gly Gln Gly Trp Leu Trp
        115                 120                 125

Gly Gly Cys Ser Asp Asn Val Gly Phe Gly Glu Ala Ile Ser Lys Gln
130                 135                 140

Phe Val Asp Ala Leu Glu Thr Gly Gln Asp Ala Arg Ala Ala Met Asn
145                 150                 155                 160

Leu His Asn Asn Glu Ala Gly Arg Lys Ala Val Lys Gly Thr Met Lys
                165                 170                 175

Arg Thr Cys Lys Cys His Gly Val Ser Gly Ser Cys Thr Thr Gln Thr
            180                 185                 190

Cys Trp Leu Gln Leu Pro Glu Phe Arg Glu Val Gly Ala His Leu Lys
        195                 200                 205

Glu Lys Tyr His Ala Ala Leu Lys Val Asp Leu Leu Gln Gly Ala Gly
210                 215                 220

Asn Ser Ala Ala Gly Arg Gly Ala Ile Ala Asp Thr Phe Arg Ser Ile
225                 230                 235                 240

Ser Thr Arg Glu Leu Val His Leu Glu Asp Ser Pro Asp Tyr Cys Leu
                245                 250                 255

Glu Asn Lys Thr Leu Gly Leu Leu Gly Thr Glu Gly Arg Glu Cys Leu
            260                 265                 270

Arg Arg Gly Arg Ala Leu Gly Arg Trp Glu Arg Arg Ser Cys Arg Arg
        275                 280                 285

Leu Cys Gly Asp Cys Gly Leu Ala Val Glu Glu Arg Arg Ala Glu Thr
            290                 295                 300

Val Ser Ser Cys Asn Cys Lys Phe His Trp Cys Cys Ala Val Arg Cys
305                 310                 315                 320

Glu Gln Cys Arg Arg Arg Val Thr Lys Tyr Phe Cys Ser Arg Ala Glu
                325                 330                 335

Arg Pro Pro Arg Gly Ala Ala His Lys Pro Gly Lys Asn Ser
            340                 345                 350

<210> SEQ ID NO 21
<211> LENGTH: 354
<212> TYPE: PRT
<213> ORGANISM: Homo sapiens

<400> SEQUENCE: 21

Met Arg Ala Arg Pro Gln Val Cys Glu Ala Leu Leu Phe Ala Leu Ala
1               5                   10                  15

Leu Gln Thr Gly Val Cys Tyr Gly Ile Lys Trp Leu Ala Leu Ser Lys
            20                  25                  30

Thr Pro Ser Ala Leu Ala Leu Asn Gln Thr Gln His Cys Lys Gln Leu
        35                  40                  45

Glu Gly Leu Val Ser Ala Gln Val Gln Leu Cys Arg Ser Asn Leu Glu
    50                  55                  60

Leu Met His Thr Val Val His Ala Ala Arg Glu Val Met Lys Ala Cys
65                  70                  75                  80

Arg Arg Ala Phe Ala Asp Met Arg Trp Asn Cys Ser Ser Ile Glu Leu
                85                  90                  95

Ala Pro Asn Tyr Leu Leu Asp Leu Glu Arg Gly Thr Arg Glu Ser Ala
            100                 105                 110

Phe Val Tyr Ala Leu Ser Ala Ala Ala Ile Ser His Ala Ile Ala Arg
        115                 120                 125

Ala Cys Thr Ser Gly Asp Leu Pro Gly Cys Ser Cys Gly Pro Val Pro
    130                 135                 140

Gly Glu Pro Pro Gly Pro Gly Asn Arg Trp Gly Gly Cys Ala Asp Asn
145                 150                 155                 160

Leu Ser Tyr Gly Leu Leu Met Gly Ala Lys Phe Ser Asp Ala Pro Met
                165                 170                 175

Lys Val Lys Lys Thr Gly Ser Gln Ala Asn Lys Leu Met Arg Leu His
            180                 185                 190

Asn Ser Glu Val Gly Arg Gln Ala Leu Arg Ala Ser Leu Glu Met Lys
        195                 200                 205

Cys Lys Cys His Gly Val Ser Gly Ser Cys Ser Ile Arg Thr Cys Trp
    210                 215                 220

Lys Gly Leu Gln Glu Leu Gln Asp Val Ala Ala Asp Leu Lys Thr Arg
225                 230                 235                 240

Tyr Leu Ser Ala Thr Lys Val Val His Arg Pro Met Gly Thr Arg Lys
                245                 250                 255

His Leu Val Pro Lys Asp Leu Asp Ile Arg Pro Val Lys Asp Ser Glu
            260                 265                 270

Leu Val Tyr Leu Gln Ser Ser Pro Asp Phe Cys Met Lys Asn Glu Lys
        275                 280                 285

Val Gly Ser His Gly Thr Gln Asp Arg Gln Cys Asn Lys Thr Ser Asn
    290                 295                 300

Gly Ser Asp Ser Cys Asp Leu Met Cys Cys Gly Arg Gly Tyr Asn Pro

```
                305                 310                 315                 320
Tyr Thr Asp Arg Val Val Glu Arg Cys His Cys Lys Tyr His Trp Cys
                    325                 330                 335
Cys Tyr Val Thr Cys Arg Arg Cys Glu Arg Thr Val Glu Arg Tyr Val
                340                 345                 350
Cys Lys

<210> SEQ ID NO 22
<211> LENGTH: 15
<212> TYPE: PRT
<213> ORGANISM: Homo sapiens

<400> SEQUENCE: 22

Arg Glu Ser Ala Phe Val Tyr Ala Leu Ser Ala Ala Ile Ser
1               5                   10                  15

<210> SEQ ID NO 23
<211> LENGTH: 14
<212> TYPE: PRT
<213> ORGANISM: Homo sapiens

<400> SEQUENCE: 23

Arg Ala Cys Thr Ser Gly Asp Leu Pro Gly Cys Ser Cys Gly
1               5                   10

<210> SEQ ID NO 24
<211> LENGTH: 13
<212> TYPE: PRT
<213> ORGANISM: Homo sapiens

<400> SEQUENCE: 24

Asn Arg Trp Gly Gly Cys Ala Asp Asn Leu Ser Tyr Gly
1               5                   10

<210> SEQ ID NO 25
<211> LENGTH: 16
<212> TYPE: PRT
<213> ORGANISM: Homo sapiens

<400> SEQUENCE: 25

Cys Lys Cys His Gly Val Ser Gly Ser Cys Ser Ile Arg Thr Cys Trp
1               5                   10                  15

<210> SEQ ID NO 26
<211> LENGTH: 12
<212> TYPE: PRT
<213> ORGANISM: Homo sapiens

<400> SEQUENCE: 26

Glu Leu Val Tyr Leu Gln Ser Ser Pro Asp Phe Cys
1               5                   10

<210> SEQ ID NO 27
<211> LENGTH: 354
<212> TYPE: PRT
<213> ORGANISM: Mus musculus

<400> SEQUENCE: 27

Met Arg Ala Arg Pro Gln Val Cys Glu Ala Leu Leu Phe Ala Leu Ala
1               5                   10                  15
Leu His Thr Gly Val Cys Tyr Gly Ile Lys Trp Leu Ala Leu Ser Lys
            20                  25                  30
```

```
Thr Pro Ala Ala Leu Ala Leu Asn Gln Thr Gln His Cys Lys Gln Leu
            35                  40                  45
Glu Gly Leu Val Ser Ala Gln Val Gln Leu Cys Arg Ser Asn Leu Glu
 50                  55                  60
Leu Met Arg Thr Ile Val His Ala Arg Gly Ala Met Lys Ala Cys
 65                  70                  75                  80
Arg Arg Ala Phe Ala Asp Met Arg Trp Asn Cys Ser Ser Ile Glu Leu
                85                  90                  95
Ala Pro Asn Tyr Leu Leu Asp Leu Glu Arg Gly Thr Arg Glu Ser Ala
               100                 105                 110
Phe Val Tyr Ala Leu Ser Ala Ala Thr Ile Ser His Thr Ile Ala Arg
               115                 120                 125
Ala Cys Thr Ser Gly Asp Leu Pro Gly Cys Ser Cys Gly Pro Val Pro
           130                 135                 140
Gly Glu Pro Pro Gly Pro Gly Asn Arg Trp Gly Gly Cys Ala Asp Asn
145                 150                 155                 160
Leu Ser Tyr Gly Leu Leu Met Gly Ala Lys Phe Ser Asp Ala Pro Met
               165                 170                 175
Lys Val Lys Lys Thr Gly Ser Gln Ala Asn Lys Leu Met Arg Leu His
               180                 185                 190
Asn Ser Glu Val Gly Arg Gln Ala Leu Arg Ala Ser Leu Glu Thr Lys
           195                 200                 205
Cys Lys Cys His Gly Val Ser Gly Ser Cys Ser Ile Arg Thr Cys Trp
           210                 215                 220
Lys Gly Leu Gln Glu Leu Gln Asp Val Ala Ala Asp Leu Lys Thr Arg
225                 230                 235                 240
Tyr Leu Ser Ala Thr Lys Val Val His Arg Pro Met Gly Thr Arg Lys
               245                 250                 255
His Leu Val Pro Lys Asp Leu Asp Ile Arg Pro Val Lys Asp Ser Glu
           260                 265                 270
Leu Val Tyr Leu Gln Ser Ser Pro Asp Phe Cys Met Lys Asn Glu Lys
               275                 280                 285
Val Gly Ser His Gly Thr Gln Asp Arg Gln Cys Asn Lys Thr Ser Asn
           290                 295                 300
Gly Ser Asp Ser Cys Asp Leu Met Cys Cys Gly Arg Gly Tyr Asn Pro
305                 310                 315                 320
Tyr Thr Asp Arg Val Val Glu Arg Cys His Cys Lys Tyr His Trp Cys
               325                 330                 335
Cys Tyr Val Thr Cys Arg Arg Cys Glu Arg Thr Val Glu Arg Tyr Val
               340                 345                 350
Cys Lys

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
gccgcttcta ccacagact                                              19

<210> SEQ ID NO 29
<211> LENGTH: 19
<212> TYPE: DNA
<213> ORGANISM: Artificial Sequence
```

```
<220> FEATURE:
<223> OTHER INFORMATION: Primer

<400> SEQUENCE: 29
ttcataccgc agtctcccc                                             19

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ggacacggac aggattgaca                                            20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
acccacggaa tcgagaaaga                                            20

<210> SEQ ID NO 32
<211> LENGTH: 25
<212> TYPE: PRT
<213> ORGANISM: Homo sapiens

<400> SEQUENCE: 32

Gln Asn Thr Ser Asp Gly Ser Gly Gly Pro Gly Gly Gly Pro Thr Ala
 1               5                  10                  15

Tyr Pro Thr Ala Pro Tyr Leu Pro Asp
            20                  25

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
cagaacacgt ccgacaaagg                                            20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
tccttctccc ccagaaagtg                                            20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
``` gagcacccctt tccactgtcc                                            20

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
acgggcaaaa cgagtctcc                                              19

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
atccccgact tgtggatttg                                             20

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
atggtggcga acaatctcg                                              19

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gcatggaagg accaggtgat                                             20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
ctccttagct gagcggctgt                                             20

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
ggattataac cgaagcgaaa cc                                          22

<210> SEQ ID NO 42
<211> LENGTH: 21
<212> TYPE: DNA
<213> ORGANISM: Artificial Sequence -continued
<220> FEATURE:
<223> OTHER INFORMATION: Primer

<400> SEQUENCE: 42
tgcgcacctt gttgtagagt g                                              21

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ttggattttg gtgtccaaag c                                              21

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ggaggggcac actgttcaat                                                20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
tacctgccag acccaccttt                                                20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gcgaaccgtc tctcctcttc                                                20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gctctacaac cgcgtcaaga                                                20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
gcgctcatcc tggctaaaga                                                20

```
<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
cccattcata aaggacttgg gagg                                          24

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gtatggaggc acccgagaac                                               20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
cacgagcgac tcttctccac                                               20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
ggacacggac aggattgaca                                               20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
acccacggaa tcgagaaaga                                               20

<210> SEQ ID NO 54
<211> LENGTH: 25
<212> TYPE: PRT
<213> ORGANISM: Mus musculus

<400> SEQUENCE: 54

Gln Asn Thr Ser Asp Gly Ser Gly Gly Ala Gly Gly Ser Pro Thr Ala
 1               5                  10                  15

Tyr Pro Thr Ala Pro Tyr Leu Pro Asp
            20                  25

<210> SEQ ID NO 55
<211> LENGTH: 25
<212> TYPE: PRT
<213> ORGANISM: Homo sapiens
```

```
<400> SEQUENCE: 55

Leu Gly Glu Arg Asp Cys Gly Ala Pro Cys Glu Pro Gly Arg Ala Asn
1               5                   10                  15

Gly Leu Met Tyr Phe Lys Glu Glu Glu
            20                  25

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
gcgtggacaa tggctactca ag                                          22

<210> SEQ ID NO 57
<211> LENGTH: 19
<212> TYPE: DNA
<213> ORGANISM: Artificial Sequence
<220> FEATURE:
<223> OTHER INFORMATION: Primer

<400> SEQUENCE: 57
ctggtcctca tcgtttagc                                              19

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
tgatggagtt ggacatggcc atg                                         23

<210> SEQ ID NO 59
<211> LENGTH: 24
<212> TYPE: DNA
<213> ORGANISM: Artificial Sequence
<220> FEATURE:
<223> OTHER INFORMATION: Primer

<400> SEQUENCE: 59
cccattcata aaggacttgg gagg                                        24
```

FRIZZLED PROTEINS AND DETECTION AND TREATMENT OF CANCER

CROSS-REFERENCE TO RELATED APPLICATIONS

This application is the National Stage of International Application No. PCT/US2005/001514 filed on Jan. 5, 2005, which claims the benefit of U.S. Provisional Application No. 60/611,919 filed Sep. 21, 2004, which are Incorporated herein by reference in their entireties.

STATEMENT AS TO FEDERALLY SPONSORED RESEARCH

This invention was made with Government support under National Institutes of Health Grant Nos. CA035711, AA002666, and AA008169. The Government has certain rights in this invention.

TECHNICAL FIELD

This invention relates to detection and treatment of liver cancer.

BACKGROUND

Hepatocellular carcinoma (HCC) is the major primary malignant tumor of the liver. Although viral etiological factors have been identified, the molecular mechanisms that contribute to tumor progression during hepatocarcinogenesis remain largely unknown. The Frizzled family of proteins is composed of ten or more seven-transmembrane proteins that act as receptors for Wnt proteins. The Wnt/Frizzled signaling network influences diverse biological processes ranging from cell fate determination to cell motility and proliferation.

β-catenin is a multifactorial protein with a role in cell-cell adhesion that involves strengthening the linkage of cadherin and α-catenin to the actin cytoskeleton. In the absence of Wnt/Frizzled signaling, β-catenin is phosphorylated by interactions with glycogen synthase kinase (GSK)-3β, and forms a complex with axin and the adenomatous polyposis coli protein (APC). Subsequently, β-catenin is targeted for degradation by the ubiquitinproteasome system. In contrast, binding of a Wnt ligand to its Frizzled receptor stabilizes intracellular β-catenin through the inhibition of GSK-3β enzymatic activity. Subsequently, β-catenin translocates into the nucleus in association with high mobility group domain factors such as Tcf/Lef. This complex is associated with transcriptional up-regulation of growth regulatory and cell migration related genes.

SUMMARY

The present invention is based, in part, on the discovery that Frizzled 7 (FZD7) is commonly overexpressed, and Frizzled 8 (FZD8) is commonly underexpressed, at the mRNA and protein level, in many HCC, for example hepatitis B virus (HBV) related HCC. Liver cancer cells that overexpress FZD7 exhibit enhanced cell motility and migration. Overexpression appears to be an early event during the multi-step process of hepatocyte transformation. Accordingly, FZD7 is a novel molecular target for therapy of liver cancer.

Accordingly, in one aspect, the invention provides a method of determining whether a cell (e.g., a liver cell) is, or is at risk for becoming, a cancer cell. The method includes (a) providing a test cell (e.g., a liver cell); (b) determining whether the cell's level of FZD7 expression is higher, or FZD8 expression is lower, than that of a control cell; and (c) classifying the test cell as (i) a cancer cell or (ii) at risk for becoming a cancer cell, if the test cell's level of FZD7 expression is higher, or the test cell's level of FZD8 expression is lower, than that of the control cell. Where the method includes determining the cell's level of FZD7 expression, the method can further include: (c) determining whether the test cell's level of FZD8 expression is lower than that of a control cell, wherein a lower level of expression of FZD8 indicates that the test cell is, or is at risk for becoming, a cancer cell. Where the method includes determining the cell's level of FZD8 expression, the method can further include: (c) determining whether the test cell's level of FZD7 expression is higher than that of a control cell, wherein a higher level of expression of FZD7 indicates that the test cell is, or is at risk for becoming, a cancer cell.

In another aspect, the invention provides a method of determining whether a patient is suffering from or at risk for cancer, e.g., whether a test tissue sample comes from a patient that is suffering from or at risk for cancer. The method can include: providing a test tissue sample (e.g., a liver tissue such as tumerous or peritumorous liver tissue) obtained from a patient, and (b) determining whether the level of FZD7 expression is higher, or whether the level of FZD8 expression is lower, in the test tissue sample than that in a comparable tissue sample obtained from a healthy individual, wherein a higher level of expression of FZD7 or a lower level of expression of FZD8 in the test tissue sample is an indication that the sample is from a patient suffering from or at risk for cancer. Where the method includes determining the level of FZD7 expression, the method can further include: (c) determining whether the level of FZD8 expression in the test tissue sample is lower than that in a tissue sample obtained from a healthy individual, wherein a lower level of expression of FZD8 is an indication that the sample comes from a patient is suffering from or at risk for cancer. Where the method includes determining the level of FZD8 expression, the method can further include: (c) determining whether the level of FZD7 expression in the test tissue sample is higher than that in a tissue sample obtained from a healthy individual, wherein a higher level of expression of FZD7 is an indication that the patient is suffering from or at risk for cancer.

In any of the methods described herein, determining the level of FZD7 or FZD8 expression can include determining the amount of FZD7 or FZD8 mRNA in the cell, e.g., using a Northern blot assay or an RT-PCR assay. In other embodiments, determining the level of FZD7 or FZD8 expression can include determining the amount of FZD7 or FZD8 protein in the cell, e.g., using an antibody, e.g., an antibody that binds to SEQ ID NOS:32 or 55.

In still another aspect, the invention includes a method of treating cancer (e.g., liver cancer) in a patient. The method includes administering to the patient an effective amount of a compound that reduces Wnt/FZD7 signaling in FZD7-expressing cells of the patient and that is optionally non-lethal to the FZD7-expressing cells. The compound can be a compound that reduces FZD7 expression in the patient, e.g., an antisense oligonucleotide, a double stranded RNA (dsRNA) that includes a nucleotide sequence that hybridizes under physiological conditions to a FZD7 nucleotide sequence, an isolated FZD7 receptor or a Wnt binding fragment thereof, and/or a genetic construct encoding a truncated form of FZD7 (e.g., a form of FZD7 lacks FZD7's intracellular and/or transmembrane domain). The compound can be administered by any route, e.g., by administration to the patient's liver.

In yet another aspect, the invention includes a method of reducing motility in a cancer cell. The method includes administering to the cell an effective amount of a compound capable of reducing Wnt/FZD7 signaling in the cell and which is optionally non-lethal to the cell. The compound can be a compound that reduces expression of FZD 7 in the cell, e.g., an antisense oligonucleotide, a double stranded RNA (dsRNA) that includes a nucleotide sequence that hybridizes under physiological conditions to a FZD7 nucleotide sequence, an isolated FZD7 receptor or a Wnt binding fragment thereof, and/or a genetic construct encoding a truncated form of FZD7 (e.g., a form of FZD7 lacks FZD7's intracellular and/or transmembrane domain).

In another aspect, the invention includes the use of a compound that reduces Wnt/FZD7 signaling in FZD7-expressing cells in the manufacture of (i) a medicament for the treatment of liver cancer or (ii) a medicament that reduces the motility of liver cancer cells. Optionally, the medicament is non-lethal to FZD7 expressing cells. The medicament can be manufactured using a compound that reduces FZD7 expression in the patient, e.g., an antisense oligonucleotide, a double stranded RNA (dsRNA) that includes a nucleotide sequence that hybridizes under physiological conditions to a FZD7 nucleotide sequence, an isolated FZD7 receptor or a Wnt binding fragment thereof, and/or a genetic construct encoding a truncated form of FZD7 (e.g., a form of FZD7 lacks FZD7's intracellular and/or transmembrane domain).

In still another aspect, the invention includes a transgenic, animal, e.g., a non-human animal, whose genome comprises a c-myc transgene and an IRS-1 transgene, wherein the animal exhibits increased susceptibility to hepatocellular carcinoma, as compared to a wild type counterpart. The animal can be a mammal, e.g., a primate, pig, rodent (e.g., mouse or rat), rabbit, cow, horse, cat, dog, sheep or goat. The transgenic animal can develop precancerous hepatocyte dysplasia in less than about 90 days from birth, e.g., in less than about 60 days from birth.

In another aspect, the invention includes a method of making a transgenic animal, e.g., a non-human animal, susceptible to HCC. The method includes: (a) crossing a first parental non-human animal whose genome comprises a c-myc transgene that is expressed in hepatic cells with a second parental animal whose genome comprises a IRS-1 transgene that is expressed in hepatic cells; and (b) isolating a progeny animal that expresses the transgenes of both parental animals and is a transgenic animal susceptible to HCC. The animal can be a non-human mammal, e.g., a primate, pig, rodent (e.g., mouse or rat), rabbit, cow, horse, cat, dog, sheep or goat.

In yet another aspect, the invention includes a method of identifying a compound for treating liver cancer. The method includes: (a) administering a test compound to a transgenic animal described herein; and (b) determining whether the compound reduces the incidence or level of liver cancer in the transgenic animal. A Compound identified by a method described herein can be used in the manufacture of a medicament for (i) the treatment of liver cancer or (ii) reducing motility of a liver cancer cell.

In still another aspect, the invention includes, method of identifying an anticancer agent. The method includes: (a) administering a test compound to a cell; and (b) determining whether the compound reduces Wnt/FZD7 signaling in the cell, wherein a compound that reduces Wnt/FZD7 signaling is a candidate anticancer agent. The cell of step (a) can be, for example, a liver cell. Step (b) can be performed, for example, by (i) determining whether the compound reduces expression of FZD7 in the cell, (ii) detecting the amount of FZD7 mRNA in the cell, or (iii) detecting the amount of FZD7 protein in the cell. The method can further include: (c) determining whether the candidate anti-cancer agent is capable of: (i) reducing cancer cell motility; (ii) reducing β-catenin accumulation in a cancer cell; or (iii) treating cancer in vitro or in vivo; wherein a candidate that is capable of at least one of these is an anti-cancer agent. A compound identified by a method described herein can be used in the manufacture of a medicament for (i) the treatment of liver cancer or (ii) reducing motility of a liver cancer cell.

In another aspect, the invention includes a method for identifying an anti-cancer agent. The method includes: (a) providing a polypeptide comprising the amino acid sequence of a FZD7 receptor protein or a fragment thereof; (b) contacting the polypeptide with a test compound; (c) detecting binding between the polypeptide and the test compound; (d) selecting the test compound if it binds to the polypeptide; and (e) determining whether the selected compound (I) reduces Wnt/FZD7 signaling in a cell that expresses FZD7, (ii) reduces motility of a cancer cell, (iii) reduces β-catenin accumulation in a cancer cell; or (iv) can be used to treat cancer in vitro, or in vivo, wherein a test compound that reduces does any one or more of a (i)-(iv) is an anti-cancer agent. The polypeptide of (a) can be a naturally occurring polypeptide or a recombinant polypeptide. The polypeptide can include SEQ ID NO:2, e.g., along with at least one non-FZD7 sequence. The polypeptide can be provided as a polypeptide expressed on the surface of a cell or as an isolated polypeptide. Compounds identified by this method can be used in the manufacture of a medicament for (i) the treatment of liver cancer or (ii) reducing motility of a liver cancer cell.

In another aspect, the invention include the use of any of the compounds described herein (e.g., candidate anti-cancer agents and/or anti-cancer agents) (a) for the treatment of liver cancer or (b) in the preparation of a pharmaceutical composition for treatment or prevention of a condition described herein, e.g., cancer, e.g., liver cancer. The composition can be used in a method for treating cancer in accordance with the methods described herein. The composition can be in any form described herein, e.g., a liquid or solid composition.

Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DESCRIPTION OF DRAWINGS

FIG. 1C: The FZD7 mRNA steady state levels in HCC cell lines expressed as relative abundance of FZD7 mRNA. The value represents the mean ±SD from 3 separate experiments.

FIG. 2A: the percent of non-migrated, and total migrated (migrated-adherent, and migrated non-adherent) cells were evaluated by a luminescent based as say. The values (percent of cells) are expressed as mean ±SD from 6 separate measurements. t-test, *p<0.01, **p<0.001 as compared to values obtained with HepG2 cells FIG. 2B: Correlation between FZD7 mRNA steady state levels and the percent of total migrated cells (both migrated-adherent and migrated-non-adherent). Z-test of correlation, p=0.02.

FIG. 3C illustrates measurements of a Tcf transcriptional activity. The HCC cell lines were co-transfected with either TOPflash (■) or FOPflash (□) and β-galactosidase expressing plasmid. Note the high level of Tcf mediated transcription activity in all three cell lines. There was a general correlation between FZD7 levels and Tcf transcriptional activity.

FIG. 4A: FZD7-FL: wild-type fall-length FZD7 protein; FZD7-ΔC: FZD7 protein truncated in the intracellular domain; FZD7-ΔTΔC: secreted FZD7 protein truncated in both the transmembrane and intracellular domains; CRD: cystein rich domain. The Wnt-ligand interacts with the CRD of FZD7 and with the epidermal growth factor repeat (EGFR) regions 1 and 2 of LRP5/6 as represented by grey boxes. FIG. 4B: a bar graph illustrating expression in a heterogenous population of Huh7 cells stably transfected with pcDNA3/FZD7-ΔTΔC or pcDNA3/empty vector as a control. Expression was assessed by quantitative real-time RT-PCR with either a first set of primers located in the extracellular domain, or a second set located in the intracellular domain of FZD7 receptor. Expression levels were normalized to the values obtained with pcDNA3. FIG. 4C: Western blot illustrating expression of FZD7-ΔTΔC as assessed using the monoclonal anti-M2 flag tag antibody in a heterogenous population of Huh7 cells stably transfected with FZD7-ΔTΔC or pcDNA3/empty vector. FIG. 4D: a bar graph illustrating expression of various forms of FZD7 in Huh7 cells. Cells were stably transfected with pLenti6/V5-GFP clone-4 (GFP-C4) served as a negative control; Huh7 cells stably transfected with pLenti6/V5-FZD7-ΔC clones-1 to 8 (ΔC-C1 to C8); Huh7 cells transiently transduced with pLenti6/V5-FZD7-C (ΔC-Tr). Huh7 cells stably transduced with pLenti6/V5-FZD7-FL clone-1 (FL-C1) served as positive controls for RT-PCR assessment with sets of primers targeting either the extracellular domain or the intracellular domain of FZD7 receptor. Expression levels were normalized to the values observed with pLenti6/V5-GFP-C4. FIG. 4E: Western blot analysis of expression of FZD7-ΔC using rabbit polyclonal anti-human FZD7 antibody with or without immunoprecipitation with a goat anti-human V5 antibodies coupled to agarose beads. Experiments were performed in Huh7 cells transduced with pLenti6/V5-FZD7-ΔC and pLenti6/V5-GFP-C4 as a negative control.

FIG. 5A: Western blots illustrating the levels of β-catenin protein in Huh7, Focus, Hep3B, and HepG2 HCC cell lines transfected with the secreted form of the FZD7-ΔTΔC receptor. FIG. 5B: Western blot illustrating the level of β-catenin protein in Huh7 cells following transduction with the transmembrane FZD7-ΔC mutant receptor cloned into pLenti6/V5. FIG. 5C: bar graph illustrating the motility of Huh7 cells toward soluble collagen-I under conditions of transient transfection with pLenti6/V5-FZD7-ΔTΔC, pLenti6/V5-FZD7-ΔC, or pLenti6/V5-GFP as a control. FIG. 5D: bar graph illustrating motility measurements of representative clones under conditions of stable integration and expression of: C1=FZD7-ΔTΔC; C5=FZD7-ΔC, and C6=FZD7-ΔC. The percent of non-migrated, and total migrated (migrated-adherent, and migrated non-adherent) cells were evaluated by a luminescent-based assay after 3 hours at 37° C. The values (percent of cells) expressed as mean ±SD, are from 6 separate measurements. t-test, *p<0.05, **p<0.01 when compared with GFP negative control.

FIGS. 6A-6B are a diagram and bar graph illustrating β-catenin constructs and the results of a cell motility assay. FIG. 6A: an illustration of the β-catenin constructs. Approximate location of functional domains: black, protein instability; right-leaning hatch, N-terminal transactivation domain; left-leaning hatch, C-terminal transactivation domain; grey, armadillo repeats, protein-protein interaction. FIG. 6B: a bar graph illustrating motility measurements of FZD7-ΔC-C6 and GFP-C4 blasticidin-selected clonal Huh7 cell populations initially transduced with pLenti6/V5-D-TOPO® lentiviral vectors expressing either the FZD7-ΔC negative dominant mutant or GFP as control, and co-transduced once again with a pLenti6/V5-D-TOPO® lentiviral vector expressing a biologically active ΔN/ΔC β-catenin mutant or GFP to keep constant the total amounts of plasmid DNA. The percent of non-migrated and total migrated (migrated-adherent, and migrated nonadherent) cells were evaluated by a luminescent-based assay after 3 hours at 37° C. The values (percent of cells) expressed as mean ±SD were derived from 6 separate measurements. Note the restoration of cell motility by the ΔN/ΔC mutant β-catenin in the setting of inhibition of the signal transduction of the receptor level with stable expression of the dominant negative FZD7 ΔC-C6 receptor mutant protein.

FIG. 7A: a bar graph illustrating quantitative real-time RT-PCR assessment of FZD7 mRNA levels in human HCC tumors (T) and the corresponding peritumorous liver parenchyma (pT), derived from Taiwan and South Africa. Non-parametric paired test, *p<0.0001; paried t-test, p=0.0187, when comparing levels in tumor to peritumoral areas. FIG. 7B: Western blot analysis of FZD7 receptor protein expression in HCC tumors (T) and the corresponding peritumorous areas (pT), as well as in Huh7 and HepG2 human hepatoma cell lines. FIG. 7C: Western blot analysis of β-catenin protein accumulation in cytosolic (C) or nuclear (N) enriched fractions from two HCC tumors and their corresponding peritumoral areas compared to two normal liver samples. Both peritumoral area and tumor overexpress FZD7 mRNA as shown by values listed below the Western blots and expressed as relative abundance of FZD7 mRNA. Each tumor and peritumor region had a wildtype β-catenin exon-3 as assessed by PCR and sequencing.

FIGS. 8A-8E illustrate exemplary FZD7, FZD8, Wnt 3, Wnt 8b and Wnt 11 human and mouse amino acid sequences, including putative binding motifs.

FIG. 9A: Normal liver from a 8 week-old non-transgenic animal. FIG. 9B: Liver from a 24 week-old IRS-1/c-myc double transgenic showing large dysplastic cells (arrows). FIG. 9C: Peritumorous liver from a 36 week-old IRS-1/c-myc double transgenic showing large size foci of dysplastic cells. FIG. 9D: Well-differentiated HCC tumor of the trabecular type derived from a 36 week-old IRS-1/c-myc double transgenic mouse. FIG. 9E: Liver from a 12 week-old X/c-myc double transgenic animal showing large dysplastic cells (arrows). FIG. 9F: Peritumorous liver from a 29 week-old X/c-myc double transgenic illustrating a large foci of dysplastic cells. FIG. 9G: Representative example of a well-differentiated HCC tumor of trabecular type derived from a 29 week-old X/c-myc double transgenic animal. FIG. 9H: Liver derived from a 5 week-old SV40-Tag single transgenic line showing proliferating hepatocytes with dysplastic features (arrows). FIG. 9I: Peritumorous liver from a 15 week-old SV40-Tag single transgenic showing diffuse microscopic infiltration by small HCC cells. FIG. 9J: Small cell HCC tumor derived from a 15 week-old SV40-Tag single transgenic animal.

FIG. 10A: c-myc Tg mice. FIG. 10B: IRS-1/c-myc Tg mice. FIG. 10C: X/c-myc Tg mice. FIG. 10D: SV40-Tag Tg mice. Black=HCC tumors, grey=dysplastic liver, and white=normal liver derived from non-transgenic littermates. Each value was normalized to the mean value of the corresponding non-transgenic littermates; nb number of animals; t-Student test, (*)p<0.05, (**)p<0.01, (†)p<0.001. All animals had a wild type β-catenin gene.

FIG. 12A: FZD7 expression as revealed by a goat polyclonal antibody in whole cell extracts derived from non-transgenic normal (Lanes 1-2), and early dysplastic liver derived from 12 week-old X/c-myc double transgenics (Lanes 3-4), HCC tumors from 29 week-old X/c-myc double transgenics (Lanes 6 and 8), and the corresponding adjacent liver with multiple dysplastic foci (Lanes 5 and 7). FIG. 12B: the specificity of the 75 kDa band corresponding to the murine FZD7 observed on Western blot analysis with the goat polyclonal antibody, (A) was confirmed with a newly prepared rabbit polyclonal antibody targeting a 25-mer synthetic peptide specific of extracellular domain of FZD7 that reacts with both mouse and human derived FDZ7 receptors. The human hepatoma cell lines Huh7 and HepG2 served as high and low positive human controls as assessed by quantitative FT-PCR (21). In addition, murine HCC tumor derived from a SV40-Tag single transgenic and one 5-week-old dysplatic tumor-free liver served as high and low positive controls as assessed by quantitative RT-PCR.

FIG. 14A: Western blot analysis of GSK3 β and phospho-GSK3 β level derived from: non-transgenic liver (black bar); early dysplastic liver of IRS-1/c-myc (8 and 24 weeks), X/c-myc (12 weeks) and SV40-Tag mice (5 weeks); tumors (T); and late dysplasia in the corresponding non-tumor (pT) of IRS-1/c-myc (36 weeks) and X/c-myc mice (30 weeks). Error bars represent the SEM of three independent experiments. FIG. 14B: Representative immunoblots with anti-GSK3 β and anti-phospho-GSK3 β antibodies.

DETAILED DESCRIPTION

Figure 1:
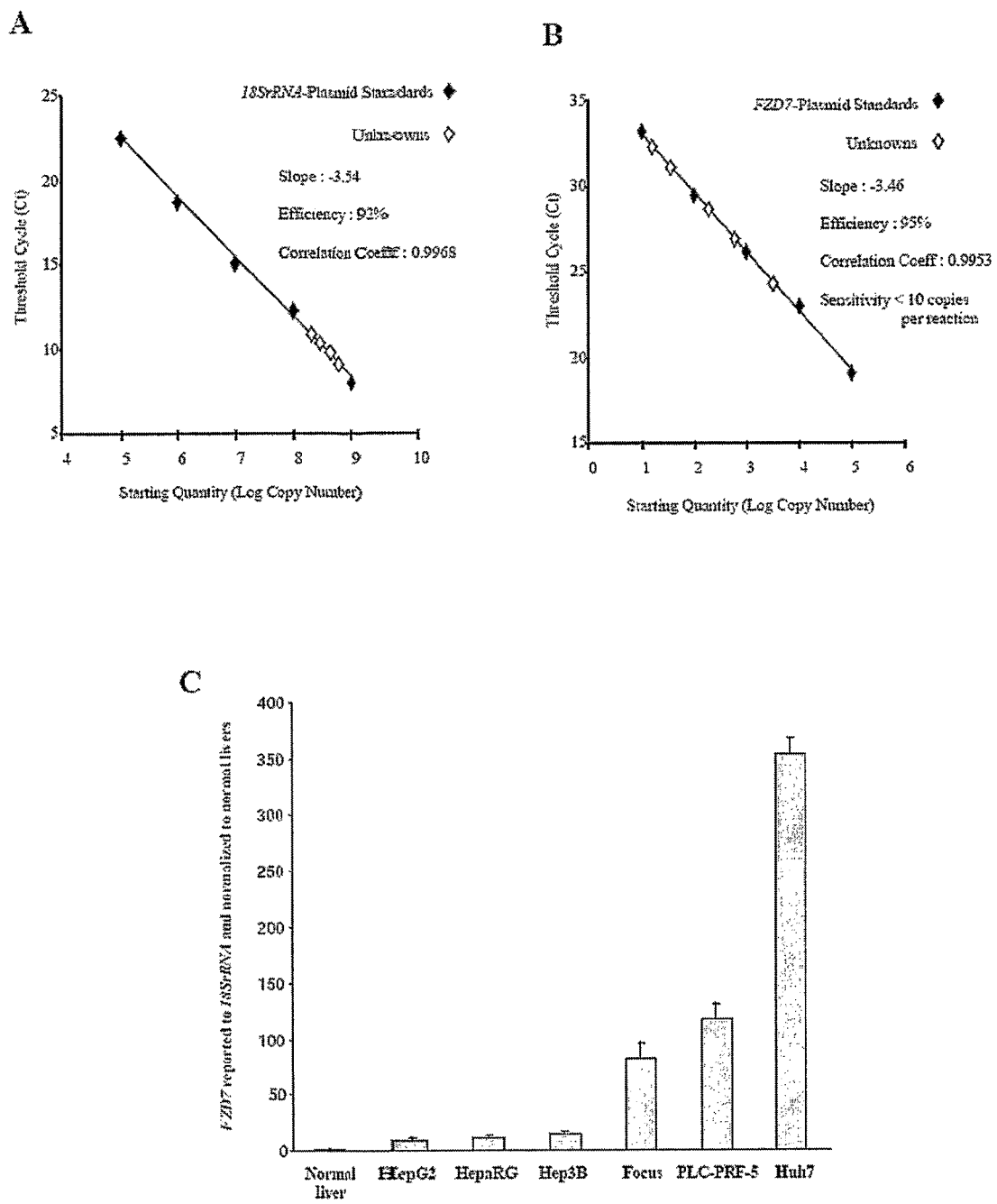
FIGS. 1A-1C are graphs that illustrate the results of a real time PCR assay for Frizzled-7 gene. Closed diamonds represent the standard curves for 18S rRNA (FIG. 1A) and FZD7 (FIG. 1B). Open diamonds represent mean values of unknown HCC tumor samples performed in duplicate. The standard curves show a 5 order of magnitude linear dynamic range.

This invention is based, at least in part, on the discovery that particular Frizzled (FZD) proteins, e.g., FZD7 and 8, are associated with certain cancers, such as liver cancer. Accordingly, the present specification provides, inter alia, methods of using FZD proteins, genes, FZD-specific antibodies and probes in diagnosis and treatment of cancer and for screening test compounds for an ability to treat cancer. Also disclosed are compounds useful for treating cancer such as liver cancer.

I. Nucleic Acids, Proteins, Vectors, and Host Cells

The terms "Frizzled," "FZD," "Frizzled protein" and "Frizzled receptor" refer to a family of mammalian proteins related to the *Drosophila* Frizzled genes, which play a role in the development of tissue polarity. The Frizzled family comprises at least 10 mammalian genes. Exemplary human Frizzled receptors include Frizzled 1, Frizzled 2, Frizzled 3, Frizzled 4, Frizzled 5, Frizzled 6, Frizzled 7, Frizzled 8, Frizzled 9 and Frizzled 10. Frizzled receptors are involved in a dynamic model of transmembrane signal transduction analogous to G-protein-coupled receptors with amino-terminal ligand binding domains.

The terms "Wnt protein," "Wnt ligand" and "Wnt" refer to a family of mammalian proteins related to the *Drosophila* segment polarity gene, wingless. In humans, the Wnt family of genes typically encode 38 to 43 kDa cysteine rich glycoproteins having hydrophobic signal sequence and a conserved asparagine-linked oligosaccharide consensus sequence (see e.g., Shimizu et al., Cell Growth Differ 8:1349-1358 (1997)). The Wnt family contains at least 19 mammalian members. Exemplary Wnt proteins include Wnt-1, Wnt-2, Wnt-2b (also known as Wnt-13), Wnt-3, Wnt-3A, Wnt-4, Wnt-5A, Wnt-5B, Wnt-6, Wnt-7A, Wnt-7B, Wnt-8A, Wnt-8B, Wnt-10A, Wnt-10B, Wnt-11, Wnt 14, Wnt 15, and Wnt 16.

In addition to Wnt ligands, a family of secreted Frizzled-related proteins (sFRPs) has been isolated. sFRPs appear to function as soluble endogenous modulators of Wnt signaling by competing with the membrane-spanning Frizzled receptors for the binding of secreted Wnt ligands. sFRPs can either antagonize Wnt function by binding the protein and blocking access to its cell surface signaling receptor, or they can enhance Wnt activity by facilitating the presentation of ligand to the Frizzled receptors.

The term "Wnt/FZD signaling pathway" refers to an intracellular signal transduction pathway that is initiated by an interaction between a Frizzled receptor, e.g., FZD7, and one or more of its ligands, e.g., a Wnt protein, e.g., Wnt 3, 8b or 11. Typically, a Wnt/FZD interaction involves binding of a Wnt protein, e.g., Wnt 3, 8b or 11, to a Frizzled receptor, e.g., FZD7, leading to activation of a signal transduction pathway. In some instances, activation of the Wnt/Frizzled signaling pathway will lead to induction of downstream-Wnt and/or FZD-inducible genes. A "downstream Wnt/FZD regulated gene product" is a protein or RNA that is regulated (e.g., up- or down-regulated) as a result of signaling by a Wnt/FZD signaling pathway.

The invention includes the use of certain FZD and Wnt nucleic acids. For example, the present invention includes the use of certain FZD7 and 8 nucleic acids, such as those that encode the amino acid sequences of the exemplary human and mouse FZD7 (SEQ ID NOs:1 and 3, respectively) and 8 (SEQ ID NO:4 and 6, respectively) receptors set forth in FIGS. 8A to 8E. As another example, the invention includes the use of certain Wnt 3, 8b, and 11 nucleic acids, such as those that encode the amino acid sequences of the exemplary human and mouse Wnt 3 (SEQ ID NOs:7 and 13, respectively), 8b (SEQ ID NOs:14 and 20, respectively), and 11 (SEQ ID NOs:21 and 27, respectively) proteins set forth in FIGS. 8A to 8E.

Also included within the present invention are the use of certain fragments of FZD and Wnt nucleic acids, e.g., a fragment of a nucleic acid sequence that encodes SEQ ID NOs:1, 3, 4, 6, 7, 13, 14, 20, 21, or 27. Fragments of FZD or Wnt nucleic acids encode at least one useful fragment of a FZD or Wnt polypeptide (e.g., a human or rodent polypeptide), respectively, such as a binding domain (e.g., a CRD domain) or other useful fragment. For example, a useful fragment of a FZD nucleic acid may encode a fragment of a FZD receptor having binding activity, e.g., a fragment corresponding to SEQ ID NO:3 or 5. As another example, a useful fragment of an Wnt nucleic acid may encode a fragment of a Wnt polypeptide having binding activity, e.g., a fragment corresponding to any one or more of SEQ ID NOs:8 to 12, 15 to 19 and 22 to 26.

FZD and Wnt nucleic acids described herein include both RNA and DNA, including genomic DNA and synthetic (e.g., chemically synthesized) DNA. Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a nucleic acid the structure of which is not identical to that of any naturally occurring nucleic acid or to that of any spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells; and (iii) cell clones, e.g., as these occur in a DNA library such as a cDNA or genomic DNA library.

In some embodiments, the invention includes the use of nucleic acid sequences that are substantially homologous to a FZD or Wnt nucleic acid. A nucleic acid sequence that is "substantially homologous" to a FZD or Wnt nucleic acid is at least 75% homologous to FZD or Wnt nucleic acid sequences that encode any one of SEQ ID NOs:1 to 27. For example, substantially homologous nucleic acid sequences can be at least about 80%, 85%, 90%, 95%, 98%, or at least about 99% homologous to sequences that encode SEQ ID NOs:1 to 27. For purposes of comparison of nucleic acids, the length of the reference nucleic acid sequence will be at least 50 nucleotides, but can be longer, e.g., at least 60 nucleotides, or more nucleotides.

As used herein, "percent homology" of two amino acid sequences or two nucleic acid sequences is determined using the algorithm of Karlin and Altschul (1990) *Proc. Nat'l Acad. Sci. USA* 87:2264-2268, modified as in Karlin and Altschul (1993) *Proc. Nat'l Acad. Sci. USA* 90:5873-5877. Such an algorithm is incorporated into the NBLAST and XBLAST programs of Altschul, et al. (1990); *J. Mol. Biol.* 215:403-410. BLAST nucleotide searches are performed with the NBLAST program, score=100, wordlength=12 to obtain nucleotide sequences homologous to FZD or Wnt nucleic acid molecules used in the invention. BLAST protein searches are performed with the XBLAST program, score=50, wordlength=3 to obtain amino acid sequences homologous to a reference polypeptide. To obtain gapped alignments for comparison purposes, Gapped BLAST is utilized as described in Altschul et al., (1997) *Nucleic Acids Res.* 25:3389-3402. When utilizing BLAST and Gapped BLAST programs, the default parameters of the respective programs (e.g., XBLAST and NBLAST) are used. See the World Wide Web at address ncbi.nlm.nih.gov.

The invention also includes the use of nucleic acids that hybridize under stringent hybridization conditions (as defined herein) to all or a portion of nucleotide sequences that encode any of SEQ ID NOs:1 to 27, or to a complement of such nucleic acid sequences. The hybridizing portion of the hybridizing nucleic acids is typically at least 15 (e.g., 20, 25, 30, or 50) nucleotides in length. The hybridizing portion of the hybridizing nucleic acid is at least about 75% (e.g., at least 80%, 90%, 95% or 98%) identical to the sequence of a portion or all of a nucleic acid encoding an FZD or Wnt polypeptide, or to its complement. Hybridizing nucleic acids of the type described herein can be used, for example, as a cloning probe, a primer (e.g., a PCR primer), or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE).

Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch. Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

Nucleic acids that hybridize to nucleotide sequence that encode any of SEQ ID NOs:1 to 27 are considered "antisense oligonucleotides."

Also included in the invention are genetic constructs (e.g., vectors and plasmids) that include a FZD and/or Wnt nucleic acid described herein, operably linked to a transcription and/or translation sequence to enable expression, e.g., expression vectors. A selected nucleic acid, e.g., a DNA molecule encoding a FZD or Wnt polypeptide, is "operably linked" to another nucleic acid molecule, e.g., a promoter, when it is positioned in such a way that the other molecule can direct transcription and/or translation of the selected nucleic acid. For example, the selected nucleic acid can be positioned adjacent to the other nucleic acid molecule.

Also included in the invention are various engineered cells which contain a FZD and/or Wnt nucleic acid described herein. For example, the invention includes transformed host cells, i.e., cells into which (or into an ancestor of which) has been introduced, by means of recombinant DNA techniques, a nucleic acid encoding a FZD and/or Wnt polypeptide. Both prokaryotic and eukaryotic cells are included, e.g., mammalian cells (e.g., liver cells), fungi, and bacteria (such as *Escherichia coli*), and the like. An engineered cell exemplary of the type included in the invention is a liver cell that overexpresses a FZD7 transgene.

A cell that "overexpresses FZD" is a cancer cell and/or transgenic cell in which expression of a particular FZD protein, such as FZD7 and/or 8, is at least about 1.5 times, e.g., at least about 2, 3, 4 or 5 times, the level of expression in a non-cancer cell or non-transgenic cell, respectively, from the same tissue type. In some embodiments, FZD expression in a cell can be compared to expression in a non-cancer or non-transgenic cell of a different tissue-type or a panel of non-cancer or non-transgenic cells of a different tissue type. In addition, expression of one type of FZD protein (e.g., FZD7) can be compared to other FZD proteins in the same cell. Methods for determining the level of expression of a particular gene are well known in the art. Such methods include, but are not limited to, RT-PCR, real time PCR and use of antibodies against the gene products.

The use of certain FZD and Wnt polypeptides are also included within the present invention. Examples of FZD polypeptides used in the present invention are human and mouse FZD polypeptides, such as those shown in SEQ ID NOs:1 and 3, respectively, and SEQ ID NOs:4 and 6, respectively. Examples of Wnt polypeptides used in the present invention are human and mouse Wnt 3, 8b and 11 polypeptides, such as those shown in SEQ ID NOs:7, 13, 14, 20, 21 and 27. Also included used in the present invention are certain fragments of FZD and Wnt polypeptides, e.g., fragments of SEQ ID NOs:1, 3, 4, 6, 7, 13, 14, 20, 21 and 27. Fragments of FZD and Wnt polypeptides may include at least one binding domain, or other useful portion of a full-length FZD and Wnt polypeptide. For example, useful fragments of FZD and Wnt polypeptides include, but are not limited to, fragments having binding activity (e.g., SEQ ID NOs: 2, 5, 8 to 12, 15 to 19, and 22 to 26).

The terms "protein" and "polypeptide" both refer to any chain of amino acids, regardless of length or post-translational modification (e.g., glycosylation or phosphorylation). Thus, the terms "Frizzled protein," "Wnt protein," "Frizzled polypeptide," and "Wnt polypeptide" include full-length naturally occurring isolated proteins, as well as recombinantly or synthetically produced polypeptides that correspond to the full-length naturally occurring proteins, or to a fragment of the full-length naturally occurring or synthetic polypeptide.

As discussed above, the terms "Frizzled polypeptide," and "Wnt polypeptide" include biologically active fragments of naturally occurring or synthetic FZD and Wnt polypeptides, respectively. Fragments of a protein can be produced by any of a variety of methods known to those skilled in the art, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of such mutagenized DNA can produce polypeptide fragments. Digestion with "end-nibbling" endonucleases can generate DNAs that encode an array of fragments. DNAs that encode fragments of a protein can also be generated, e.g., by random shearing, restriction digestion, chemical synthesis of oligonucleotides, amplification of DNA using the polymerase chain reaction, or a combination of the above-discussed methods. Fragments can also be chemically synthesized using techniques known in the art, e.g., conventional Merrifield solid phase FMOC or t-Boc chemistry.

A purified or isolated compound is a composition that is at least 60% by weight the compound of interest, e.g., a FZD polypeptide, Wnt polypeptide, or antibody. For example, the preparation can be at least 75% (e.g., at least 90%, 95%, or even 99%) by weight the compound of interest. Purity can be measured by any appropriate method known in the art, e.g., column chromatography, polyacrylamide gel electrophoresis, or IPLC analysis.

In certain embodiments, FZD and Wnt polypeptides include sequences substantially identical to all or portions of a naturally occurring FZD and Wnt polypeptides. Polypeptides "substantially homologous" to the FZD and Wnt polypeptide sequences described herein have an amino acid sequence that is at least 65% (e.g., at least 75%, 80%, 85%, 90%, 95% or 99%, e.g., 100%), homologous to an amino acid sequence represented by SEQ ID NOs:1 to 27 (measured as described herein). For purposes of comparison, the length of the reference FZD and Wnt polypeptide sequence can be at least 16 amino acids, e.g., at least 20 or 25 amino acids.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The invention also includes the use of fusion proteins (and nucleic acids that encode such fusion proteins) in which a portion of a FZD (e.g., FZD7 and/or 8) or Wnt (e.g., Wnt 3, 8b and/or 11) polypeptide is fused to an unrelated polypeptide (e.g., a marker polypeptide or a fusion partner) to create a fusion protein. For example, the polypeptide can be fused to a hexa-histidine tag or a FLAG tag to facilitate purification of bacterially expressed polypeptides or to a hemagglutinin tag or a FLAG tag to facilitate purification of polypeptides expressed in eukaryotic cells. The invention also includes, for example, the use of isolated polypeptides (and the nucleic acids that encode these polypeptides) that include a first portion and a second portion, wherein the first portion includes, e.g., a FZD or Wnt polypeptide, and the second portion includes an unrelated polypeptide, e.g., an immunoglobulin constant (Fc) region or a detectable marker.

The fusion partner can be, for example, a polypeptide that facilitates secretion, e.g., a secretory sequence. Such a fused polypeptide is typically referred to as a preprotein. The secretory sequence can be cleaved by the host cell to form the mature protein. Also within the invention are nucleic acids that encode a FZD and/or Wnt polypeptide fused to a polypeptide sequence to produce an inactive preprotein. Preproteins can be converted into the active form of the protein by removal of the inactivating sequence.

II. Methods for Detecting Cancer

Without being bound by theory, it appears that various FZD proteins, e.g., FZD7 and 8, are important in cancer, e.g., liver cancer. In particular, hepatocytes appear to overexpress FZD7 early during the process of transformation, e.g., prior to the development of HCC. Similarly, such cells often underexpress FZD8.

Accordingly, the present invention provides methods of detecting cancer cells, facilitating the diagnosis of the presence and severity (e.g., tumor grade, tumor burden, and the like) of cancer in a patient, facilitating a determination of the prognosis of a patient and assessing the responsiveness of the patient to therapy (e.g., by providing a measure of therapeutic effect through, for example, assessing tumor burden during or following a chemotherapeutic regimen).

Detection can be based on detection of a polynucleotide (e.g., a FZD7 and/or 8 polynucleotide) that is differentially expressed in a cancer cell (e.g., as compared to a non-cancer cell) and/or detection of a polypeptide (e.g., a FZD7 and/or 8 polypeptide) encoded by a polynucleotide that is differentially expressed in a cancer cell. The detection methods of the invention can be conducted in vitro or in vivo, on a biological sample, e.g., isolated cells and/or whole tissues.

A "biological sample" as used herein is a sample of biological tissue or fluid that contains nucleic acids or polypeptides, e.g., a FZD7 protein, polynucleotide or transcript. Such samples include, but are not limited to, tissue obtained from, e.g., liver, lung, lymph nodes, colon, stomach, pancreas, bile duct, small bowel and/or esophagus. Biological samples may also include sections of tissues such as biopsy and autopsy samples, frozen sections taken for histologic purposes, blood, plasma, serum, sputum, stool, tears, mucus, bile, saliva, lymph, hair, skin, etc. Biological samples also include explants and primary and/or transformed cell cultures derived from patient tissues. A biological sample is typically obtained from a eukaryotic organism, e.g., a primate such as a chimpanzee or human; cow; horse; goat; sheep; dog; cat; a rodent, e.g., guinea pig, rat or mouse; rabbit; bird; reptile; or fish. A sample is usually provided by removing a sample of cells from an animal, but can also be accomplished by providing previously isolated cells (e.g., isolated by another person, at another time and/or for another purpose), or by performing the methods of the invention in vivo. Archival tissues, having treatment or outcome history, can be used.

In some embodiments, methods are provided for detecting a cancer cell by detecting expression in the cell of a transcript (e.g., a FZD7 and/or 8 transcript) that is differentially expressed in a cancer cell. Any of a variety of known methods can be used for detection including but not limited to, detection of a transcript by hybridization of mRNA with an appropriate hybridization probe; detection of a transcript by a polymerase chain reaction using specific oligonucleotide primers; and in situ hybridization using an appropriate hybridization probe. The methods can be used to detect and/or measure mRNA levels of a gene that is differentially expressed in a cancer cell. In some embodiments, the methods comprise: a) contacting a sample with a polynucleotide that corresponds to a differentially expressed gene described herein under conditions that allow hybridization; and b) detecting hybridization, if any.

Detection of differential hybridization, when compared to a suitable control, is an indication of the presence in the sample of a polynucleotide that is differentially expressed in a cancer cell. Appropriate controls include, for example, a sample that is not a cancer cell, a sample that is known not to contain a polynucleotide that is differentially expressed in a cancer cell, and use of a labeled polynucleotide of the same "sense" as the polynucleotide that is differentially expressed in the cancer cell. Conditions that allow hybridization are known in the art and have been described in more detail above. Detection can also be accomplished by any known method, including, but not limited to, in situ hybridization, PCR (polymerase chain reaction) and/or RT-PCR (reverse transcription-PCR), or combinations of known techniques. A variety of labels and labeling methods for polynucleotides are known in the art and can be used in the assay methods of the invention. Specificity of hybridization can be determined by comparison to appropriate controls.

Polynucleotides generally comprising at least 10 nt, at least 12 nt or at least 15 contiguous nucleotides of a polynucleotide described herein, such as those having the sequence as depicted herein, can be used for a variety of purposes, such as probes or PCR primers for detection and/or measurement of transcription levels of a polynucleotide that is differentially expressed in a cancer cell. As will be appreciated by the skilled artisan, the probe can be detectably labeled and contacted with, for example, an array comprising immobilized polynucleotides obtained from a test sample (e.g., mRNA). Alternatively, the probe can be immobilized on an array and the test sample detectably labeled. The use of these and other variations of the methods of the invention are well within the skill in the art and are within the scope of the invention.

Nucleotide probes can be used to detect expression of a gene corresponding to the provided polynucleotide. In Northern blots, mRNA is separated electrophoretically and contacted with a probe. A probe is detected as hybridizing to an mRNA species of a particular size. The amount of hybridization can be quantified to determine relative amounts of expression. Probes can be used for in situ hybridization to cells to detect expression. Probes can also be used in vivo for diagnostic detection of hybridizing sequences. Probes can be labeled with a radioactive isotope or other types of detectable labels, e.g., chromophores, fluorophores and/or enzymes. Other examples of nucleotide hybridization assays are described in WO92/02526 and U.S. Pat. No. 5,124,246.

PCR is another means for detecting small amounts of target nucleic acids (see, e.g., Mullis et al., Meth. Enzymol. (1987) 155:335; U.S. Pat. Nos. 4,683,195; and 4,683,202). Two primer oligonucleotides that hybridize with the target nucleic acids can be used to prime the reaction. The primers can be composed of sequence within or 3' and 5' to the polynucleotides described herein. After amplification of the target by standard PCR methods, the amplified target nucleic acids can be detected by methods known in the art, e.g., Southern blot. mRNA or cDNA can also be detected by traditional blotting techniques (e.g., Southern blot, Northern blot, etc.) described in Sambrook et al., "Molecular Cloning: A Laboratory Manual" (New York, Cold Spring Harbor Laboratory, 1989) (e.g., without PCR amplification). In general, mRNA or cDNA generated from mRNA using a polymerase enzyme can be purified and separated using gel electrophoresis, and transferred to a solid support, such as nitrocellulose. The solid support can be exposed to a labeled probe and washed to remove any unhybridized probe. Duplexes containing the labeled probe can then be detected.

Methods using PCR amplification can be performed on the DNA from one or more cells. The use of the polymerase chain reaction is described in Saiki et al. (1985) Science 239:487, and a review of techniques may be found in Sambrook et al., "Molecular Cloning: A Laboratory Manual" (New York, Cold Spring Harbor Laboratory, 1989; pp. 14.2-14.33). A detectable label may be included in the amplification reaction. Suitable detectable labels include fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4,4',5',7,7'-hexachlorofluorescein (HEX), 5-carboxyfluorescein (5-FAM) or N,N,N',N'-tetramethyl-6-carboxyrho-damine (TAMRA)), radioactive labels, (e.g., $^{32}P$, $^{35}S$, $^{3}H$, etc.), and the like. The label may be a two stage system, where the polynucleotide is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In one embodiment, expression level is assessed by using real time PCR. RNA is isolated from a sample of interest. PCR primers are designed to amplify the specific gene of interest. PCR product accumulation is measured using a dual-labeled fluorogenic oligonucleotide probe. The probe is labeled with two different flourescent dyes, the 5' terminus reporter dye and the 3'-terminus quenching dye. The oligonucleotide probe is selected to be homologous to an internal target sequence present in the PCR amplicon. When the probe is intact, energy transfer occurs between the two fluorophors, and the fluorescent emission is quenched. During the extension phase of PCR, the probe is cleaved by 5' nuclease activity of Taq polymerase. Therefore, the reporter is no longer in proximity to the quencher, and the increase in emission intensity is measured. An exemplary method for detecting FZD expression using real time PCR is provided in the Examples section, below. The primers can also be used in other methods, for example RT-PCR. This assay provides a quantitative measure of nucleic acid.

In other embodiments, methods are provided for detecting a cancer cell by detecting expression of a protein (e.g., a FZD7 and/or 8 protein) that is differentially expressed by the cell. Any of a variety of known methods can be used for detection, including but not limited to methods that employ binding compounds, e.g., antibodies, e.g., as is useful in ELISA and/or Western blotting methods. Such an antibodies can be polyclonal or monoclonal, or antigen binding fragment thereof, and can be labeled with a detectable marker (e.g., fluorophore, chromophore or isotope, etc). Where appropriate, the compound can be attached to a solid support such as a bead, plate, filter, resin, etc. Determination of formation of the compound/target complex can be effected by contacting the complex with a further compound (e.g., a secondary antibody) that specifically binds to the first compound (or complex). Like the first compound, the further compound can be attached to a solid support and/or can be labeled with a detectable marker.

The materials needed to perform the detection methods described herein can be provided as part of a kit. Thus, the invention further provides kits for detecting the presence and/or a level of a polynucleotide that is differentially expressed in a cancer cell (e.g., by detection of an mRNA encoded by the differentially expressed gene of interest), and/or a polypeptide encoded thereby, in a biological sample. Procedures using these kits can be performed by clinical laboratories, experimental laboratories, medical practitioners or private individuals. The kits of the invention for detecting a polypeptide encoded by a polynucleotide that is differentially expressed in a cancer cell may comprise a moiety, such as an antibody, that specifically binds the polypeptide. The kits of the invention used for detecting a polynucleotide that is differentially expressed in a cancer cell may comprise a moiety that specifically hybridizes to such a polynucleotide. The kit may optionally provide additional components that are useful in the procedure including, e.g., buffers, developing reagents, labels, reacting surfaces, means for detection, control samples, standards, instructions, and interpretive information.

The present invention further relates to methods of detecting/diagnosing a neoplastic or preneoplastic condition in a mammal (for example, a human). "Diagnosis" as used herein generally includes determination of a patient's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

One exemplary detection/diagnostic method includes: (a) obtaining from a mammal (e.g., a human) a biological sample (e.g., liver tissue), (b) detecting in the sample the presence of a FZD7 and/or 8 gene product (e.g., protein or mRNA), and (c) comparing the amount of FZD7 and/or 8 gene product present with that in a control sample. In accordance with this method, the presence in the sample of elevated levels of FZD7 gene product and/or reduced levels of FZD8 gene product indicates that the subject has a neoplastic or preneoplastic condition, e.g., liver cancer or a risk for developing liver cancer.

The identification of elevated levels of FZD7 protein and/or reduced levels of FZD8 protein in accordance with the present invention makes possible the identification of patients that are likely to benefit from specialized therapy. For example, a biological sample from a post primary therapy subject (e.g., subject having undergone surgery) can be screened for the presence of elevated levels of the protein, determined by studies of normal populations, being indicative of residual tumor tissue. Similarly, tissue surrounding the cut site of a surgically removed tumor (e.g., peritumorous tissue) can be examined (e.g., by immunofluorescence), the presence of elevated levels of FZD7 or reduced levels of FZD8 (relative to the surrounding tissue) being indicative of potential development of the disease in this tissue or incomplete removal of the tumor. The ability to identify such patients makes it possible to tailor therapy to the needs of the particular patient. Subjects undergoing non-surgical therapy, e.g., chemotherapy or radiation therapy, can also be monitored, the presence in samples from such subjects of elevated levels of FZD7 or reduced levels of FZD8 being indicative of the need for continued treatment. Skilled practitioners will also appreciate that staging of cancer (e.g., liver cancer) for purposes of optimizing treatment regimens can be performed using the methods described herein.

III. Methods for Identifying Compounds Capable of Treating Cancer

The invention provides methods for screening test compounds for an ability to treat cancer, e.g., liver cancer. A "test compound" as described herein is any compound that can be screened using the methods described herein. For example, a test compound can be, e.g., a small organic or inorganic molecule (M.W. less than 1,000 Da). Alternatively or in addition, the test compound can be a polypeptide (e.g., a polypeptide having a random or predetermined amino acid sequence or a naturally-occurring or synthetic polypeptide) or a nucleic acid, such as a DNA or RNA molecule. A test compound can be naturally occurring (e.g., an herb or a natural product), or synthetic, or can include both natural and synthetic components. A test compound can have a formula weight of less than about 10,000 grams per mole, less than 5,000 grams per mole, less than 1,000 grams per mole, or less than about 500 grams per mole. The test compound can be, for example, any organic or inorganic compound (e.g., heteroorganic or organometallic compound), an amino acid, amino acid analog, polypeptide, peptidomimetic (e.g., peptoid), oligopeptide (e.g., from about 5 to about 25 amino acids in length, preferably from about 10 to 20 or 12 to 18 amino acids in length, preferably 12, 15, or 18 amino acids in length), nucleotide, nucleotide analog, polynucleotide, polynucleotide analog, ribonucleic acid, deoxyribonucleic acid, antisense oligonucleotide, ribozyme, saccharide, lipid (e.g., a sphingolipid), and/or a fatty acid, or any combination thereof.

The terms "antagonist" or "inhibitor" of Wnt/FZD signaling (e.g., Wnt/FZD7 signaling) refer to compounds that, e.g., bind to Wnt proteins (e.g., Wnt 3, 8, and/or 11) and/or FZD receptors (e.g., FZD7) and/or partially or totally block or inhibit Wnt/FZD signaling (e.g., Wnt/FZD7 signaling) as measured in known assays for Wnt/FZD signaling (e.g., measurement of β-catenin levels, oncogene expression controlled by Tcf and Lef transcription factors or other downstream Wnt/Frizzled regulated gene products). Inhibitors include, e.g., antibodies directed against Wnt or FZD proteins, modified versions of Wnt or FZD proteins, naturally occurring and synthetic ligands, antagonists, agonists, antibodies, small chemical molecules, and the like. Assays for detecting inhibitors or antagonists are described in more detail below.

Libraries of Test Compounds

In certain embodiments, screens of the present invention utilize libraries of test compounds. A "library" is a collection of compounds (e.g., as a mixture or as physically separated individual compounds) synthesized from various combinations of one or more starting components. At least some of the compounds must differ from at least some of the other compounds in the library. A library can include, e.g., 5, 10, 50, 100, 1000, or even 10,000, 50,000, or 100,000, or more different compounds (i.e., not simply multiple copies of the same compounds, although some compounds in the library may be duplicated or represented more than once). Each of the different compounds will be present in an amount such that its presence can be determined by some means, e.g., can be isolated, analyzed, and/or detected with a receptor or suitable probe. The actual quantity of each different compound needed so that its presence can be determined will vary due to the actual procedures used and may change as the technologies for isolation, detection, and analysis advance. When the compounds are present in a mixture in substantially equimolar amounts, for example, an amount of 100 picomoles of each compound can often be detected. Libraries can include both libraries of individual compounds (e.g., present substantially as a single type of compound-per-well, made via parallel synthesis or the pool and split pool method) and mixtures containing substantially equimolar amounts of each desired compound (i.e., wherein no single compound dominates). Either library format can allow identification of an active compound discovered in an assay.

Test compounds can be screened individually or in parallel. An example of parallel screening is a high throughput drug screen of large libraries of chemicals. Such libraries of candidate compounds can be generated or purchased, e.g., from Chembridge Corp., San Diego, Calif. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. *Acc. Ches. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an antiidiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of Hobbs DeWitt et al (*Proc. Natl. Acad. Sci. U.S.A.* 90:6909 (1993)). Other synthesis methods, including the "tea-bag" technique of Houghten (see, e.g., Houghten et al., *Nature* 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al, *J. Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening libraries of test compounds are described above.

Screening Methods

The invention provides methods for identifying compounds capable of treating cancer, e.g., liver cancer. Although applicants do not intend to be bound by any particular theory as to the biological mechanism involved, such compounds are thought to modulate specifically (1) Wnt/FZD signaling (e.g., by binding to FZD7, Wnt 3, Wnt 8b and/or Wnt 11 polypeptides and/or reducing (e.g., preventing) Wnt/FZD-mediated transcription) and/or (2) expression of FZD7 and/or FZD8.

In certain aspects of the present invention, screening for such compounds is accomplished by (i) identifying from a group of test compounds those that bind to a FZD7, Wnt 3, Wnt 8b and/or Wnt 11 polypeptide, modulate an interaction between FZD7 and its ligand (e.g., Wnt 3, Wnt 8b and/or Wnt 11) and/or modulate (i.e., increase or decrease) transcription and/or translation of FZD7 and/or FZD8; and, optionally, (ii) further testing such compounds for their ability to modulate Wnt/FZD signaling, reduce cancer cell motility, reduce β-catenin accumulation in cancer cells and/or to treat cancer in vitro or in vivo. Test compounds that bind to FZD7, Wnt 3, Wnt 8b and/or Wnt 11 polypeptides, modulate an interaction between FZD7 and its ligand (e.g., Wnt 3, Wnt 8b and/or Wnt 11), or modulate transcription and/or translation of FZD7 and/or FZD8, are referred to herein as "candidate anti-cancer agents." Candidate anti-cancer agents further tested and found to be capable of modulating in vitro or in vivo Wnt/FZD signaling, reducing cancer cell motility, reduce β-catenin accumulation in cancer cells, and/or treating cancer are considered "anti-cancer agents." In the screening methods of the present invention, candidate anti-cancer agents can be, but do not necessarily have to be, tested to determine whether they are anti-cancer agents. Assays of the present invention may be carried out in biological samples, whole cell preparations and/or ex vivo cell-free systems.

In one aspect, the invention includes methods for screening test compounds to identify compounds that bind to FZD polypeptides, e.g., FZD7 polypeptides, and/or to Wnt polypeptides, e.g., Wnt 3, 8b and/or 11 polypeptides. Binding of a test compound to a FZD or Wnt polypeptide can be detected, for example, in vitro by reversibly or irreversibly immobilizing the test compound(s) or the Wnt or FZD polypeptide on a substrate, e.g., the surface of a well of a 96-well polystyrene microtitre plate. Methods for immobilizing polypeptides and other small molecules are well known in the art. For example, microtitre plates can be coated with a FZD or Wnt polypeptide by adding the polypeptide in a solution (typically, at a concentration of 0.05 to 1 mg/ml in a volume of 1-100 µl) to each well, and incubating the plates at room temperature to 37° C. for a given amount of time, e.g., for 0.1 to 36 hours. Polypeptides not bound to the plate can be removed by shaking excess solution from the plate, and then washing the plate (once or repeatedly) with water or a buffer. Typically, the polypeptide is in water or a buffer. The plate can then be washed with a buffer that lacks the bound polypeptide. To block the free protein-binding sites on the plates, plates can be blocked with a protein that is unrelated to the bound polypeptide. For example, 300 µl of bovine serum albumin (BSA) at a concentration of 2 mg/ml in Tris-HCl can be used. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a particle, e.g., beaded agarose or beaded sepharose, can be used as the substrate. Test compounds can then be added to the coated plate and allowed to bind to the FZD or Wnt polypeptide (e.g., at 37° C. for 0.5-12 hours). The plate can then be rinsed as described above. Skilled practitioners will appreciate that many variations of this method are possible. For example, the method can include coating a substrate with a test compound and adding Wnt or FRZ polypeptides to the substrate-bound compound.

Binding of FZD or Wnt to a second compound, e.g., the test compound described above or to a binding partner (e.g., FZD7 to Wnt 3, 8b and/or 11; discussed in further detail below), can be detected by any of a variety of art-known methods. For example, an antibody that specifically binds to a FZD or Wnt polypeptide (i.e., an anti-FZD antibody, e.g., the polyclonal antibody described in the Examples section, or an anti-Wnt antibody) can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds to the Fc portion of the anti-FZD or anti-Wnt antibody). In an alternative detection method, the FZD or Wnt polypeptide is labeled (e.g., with a radioisotope, fluorophore, chromophore, or the like), and the label is detected. In still another method, a FZD or Wnt polypeptide is produced as a fusion protein with a protein that can be detected optically, e.g., green fluorescent protein (which can be detected under UV light). In an alternative method, the polypeptide is produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen or epitope that can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various methods for identifying polypeptides (e.g., test polypeptides) that bind to a FZD or Wnt polypeptides, the conventional two-hybrid assays of protein/protein interactions can be used (see e.g., Chien et al., *Proc. Natl. Acad. Sci. USA,* 88:9578, 1991; Fields et al., U.S. Pat. No. 5,283,173; Fields and Song, *Nature,* 340:245, 1989; Le Douarin et al., *Nucleic Acids Research,* 23:876, 1995; Vidal et al., *Proc. Natl. Acad. Sci. USA,* 93:10315-10320, 1996; and White, *Proc. Natl. Acad. Sci. USA,* 93:10001-10003, 1996). Generally, two-hybrid methods involve reconstitution of two separable domains of a transcription factor. One fusion protein includes the FZD or Wnt polypeptide fused to either a transactivator domain or DNA binding domain of a transcription factor (e.g., of Gal4). The other fusion protein contains a test polypeptide or a binding partner for the polypeptide included in the first fusion protein, fused to either the DNA binding domain or a transactivator domain of a transcription factor. Binding of the FZD or Wnt polypeptide to the test polypeptide or binding partner reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

In another aspect, the invention includes methods for screening test compounds to identify a compound that modulates a protein-protein interaction between FZD and Wnt polypeptides. A method useful for high throughput screening of compounds capable of modulating protein-protein interactions between transcriptional regulators is described in Lepourcelet et al., Cancer Cell 5: 91-102 (2004), which is incorporated herein by reference in its entirety. Typically, a first compound is provided. The first compound is a FZD (e.g., FZD7) or Wnt (e.g., Wnt 3, 8b, or 11) polypeptide or biologically active fragment thereof. A second compound is provided that is different from the first compound and is labeled. The second compound is a FZD (e.g., FZD7) or Wnt (e.g., Wnt 3, 8b, or 11) polypeptide or biologically active fragment thereof. A test compound is provided. The first compound, second compound and test compound are contacted with each other. The amount of label bound to the first compound is then determined. A change in protein-protein interaction between the first compound and the second compound as assessed by label bound is indicative of the usefulness of the test compound in modulating a protein-protein interaction between the FZD and Wnt polypeptide.

In certain embodiments, the first compound provided is attached to a solid support. Solid supports include, e.g., resins (e.g., agarose and beads) and multiwell plates. In certain embodiments, the method includes a washing step after the contacting step, so as to separate bound and unbound label.

In certain embodiments, a plurality of test compounds is contacted with the first compound and second compound. The different test compounds can be contacted with the other compounds in groups or separately. In certain embodiments, each of the test compounds is contacted with both the first compound and the second compound in an individual well. For example, the method can screen libraries of test compounds. Libraries of test compounds are discussed in detail above. Libraries can include, e.g., natural products, organic chemicals, peptides, and/or modified peptides, including, e.g., D-amino acids, unconventional amino acids, and N-substituted amino acids. Typically, the libraries are in a form compatible with screening in multiwell plates, e.g., 96-well plates. The assay is particularly useful for automated execution in a multiwell format in which many of the steps are controlled by computer and carried out by robotic equipment. The libraries can also be used in other formats, e.g., synthetic chemical libraries affixed to a solid support and available for release into microdroplets.

In certain embodiments, the first compound is a FZD7 polypeptide or fragment thereof and the second compound is a Wnt polypeptide, such as Wnt 3, 8b, or 11, or fragment thereof. In other embodiments, the first compound is a Wnt polypeptide, such as Wnt 3, 8b, or 11 polypeptide or fragment thereof, and the second compound is a FZD7 polypeptide or fragment thereof. The solid support to which the first compound is attached can be, e.g., sepharose beads, SPA beads (microspheres that incorporate a scintillant) or a multiwell plate. SPA beads can be used when the assay is performed without a washing step, e.g., in a scintillation proximity assay. Sepharose beads can be used when the assay is performed with a washing step. The second compound can be labeled with any label that will allow its detection, e.g., a radiolabel, a fluorescent agent, biotin, a peptide tag, or an enzyme fragment. The second compound can also be radiolabeled, e.g., with $^{125}$I or $^3$H.

In certain embodiments, the enzymatic activity of an enzyme chemically conjugated to, or expressed as a fusion protein with, the first or second compound, is used to detect bound protein. A binding assay in which a standard immunological method is used to detect bound protein is also included. In certain other embodiments, the interaction of Wnt and FZD polypeptides or fragments thereof is detected by fluorescence resonance energy transfer (FRET) between a donor fluorophore covalently linked to a FZD or Wnt polypeptide (e.g., a fluorescent group chemically conjugated to FZD or Wnt, or a variant of green fluorescent protein (GFP) expressed as an FZD or Wnt-GFP chimeric protein) and an acceptor fluorophore covalently linked to a substrate protein, where there is suitable overlap of the donor emission spectrum and the acceptor excitation spectrum to give efficient nonradiative energy transfer when the fluorophores are brought into close proximity through the protein-protein interaction of FZD and Wnt polypeptides.

In other embodiments, the protein-protein interaction is detected by reconstituting domains of an enzyme, e.g., beta-galactosidase (see Rossi et al, Proc. Natl. Acad. Sci. USA 94:8405-8410 (1997)).

In still other embodiments, the protein-protein interaction is assessed by fluorescence ratio imaging (Bacskai et al, Science 260:222-226 (1993)) of suitable chimeric constructs of FZD and Wnt polypeptides in cells, or by variants of the two-hybrid assay (Fearon et al, Proc Natl Acad Sci USA 89:7958-7962 (1992); Takacs et al, Proc Natl Acad Sci USA 90:10375-10379 (1993); Vidal et al, Proc Natl Acad Sci USA 93:10321-10326 (1996)) employing suitable constructs of FZD and Wnt polypeptides and tailored for a high throughput assay to detect compounds that inhibit the FZD/Wnt interaction. These embodiments have the advantage that the cell permeability of the test compounds is assured.

For example, in one assay, a FZD or Wnt polypeptide or fragment thereof is adsorbed to ELISA plates. The FZD or Wnt polypeptides are then exposed to test compounds, followed by a glutathione-S-transferase (GST)-binding partner fusion protein, e.g., a GST-FZD or -Wnt polypeptide fusion protein. Bound protein is detected with goat anti-GST antibody, alkaline phosphatase (AP)-coupled anti-goat IgG, and AP substrate. Compounds that interfere with protein-protein interactions yield reduced AP signals in the ELISA plates.

In still another aspect, the invention provides methods of identifying test compounds that modulate (e.g., increase or decrease) expression of a FZD polypeptide. The method includes contacting a FZD nucleic acid with a test compound and then measuring expression of the encoded FZD polypeptide. In a related aspect, the invention features a method of identifying compounds that modulate (e.g., increase or decrease) the expression of FZD polypeptides by measuring expression of a FZD polypeptide in the presence of the test compound or after the addition of the test compound in: (a) a cell line into which has been incorporated a recombinant construct including the FZD nucleic acid sequence or fragment or an allelic variation thereof; or (b) a cell population or cell line that naturally selectively expresses FZD, and then measuring the expression of the FZD protein.

Since the FZD nucleic acids described herein have been identified, they can be cloned into various host cells (e.g., mammalian cells, insect cells, bacteria or fungi) for carrying out such assays in whole cells.

In certain embodiments, an isolated nucleic acid molecule encoding a FZD polypeptide is used to identify a compound that modulates (e.g., increases or decreases) the expression of FZD in vivo (e.g., in a FZD-producing cell). In such embodiments, cells that express a FZD (e.g., FZD7 and/or 8) are cultured, exposed to a test compound (or a mixture of test compounds), and the level of FZD expression is compared with the level of FZD expression or activity in cells that are otherwise identical but that have not been exposed to the test compound(s). Standard quantitative assays of gene expression can be used.

Expression of FZD can be measured using art-known methods, for example, by Northern blot PCR analysis or RNAse protection analyses using a nucleic acid molecule of the invention as a probe. Other examples include enzyme-linked immunosorbent assay (ELISA), radioimmunoassay (RIA) and fluorescent activated cell sorting (FACS). The level of expression in the presence of the test molecule, compared with the level of expression in its absence, will indicate whether or not the test compound modulates the expression of a FZD polypeptide.

In still another aspect, the invention provides methods of screening test compounds utilizing cell systems that are sensitive to perturbation of one or several transcriptional/translational components.

In certain embodiments, the methods include identifying candidate compounds that interfere with steps in FZD translational accuracy, such as maintaining a proper reading frame during translation and terminating translation at a stop codon. This method involves constructing cells in which a detectable reporter polypeptide can only be produced if the normal process of staying in one reading frame or of terminating translation at a stop codon has been disrupted. This method further involves contacting the cell with a test compound to examine whether it increases or decreases the production of the reporter polypeptide.

In other embodiments, the cell system is a cell-free extract and the method involves measuring transcription or translation in vitro. Conditions are selected so that transcription or translation of the reporter is increased or decreased by the addition of a transcription modifier or a translation modifier to the cell extract.

One method for identifying candidate compounds relies upon a transcription-responsive gene product. This method involves constructing a cell in which the production of a reporter molecule changes (i.e., increases or decreases) under conditions in which cell transcription of a FZD nucleic acid changes (i.e., increases or decreases). Specifically, the reporter molecule is encoded by a nucleic acid transcriptionally linked to a sequence constructed and arranged to cause a relative change in the production of the reporter molecule when transcription of a FZD nucleic acid changes. A gene sequence encoding the reporter may, for example, be fused to part or all of the gene encoding the transcription-responsive gene product and/or to part or all of the genetic elements that control the production of the gene product. Alternatively, the transcription-responsive gene product may stimulate transcription of the gene encoding the reporter, either directly or indirectly. The method further involves contacting the cell with a test compound, and determining whether the test compound increases or decreases the production of the reporter molecule in the cell.

Alternatively, the method for identifying candidate compounds can rely upon a translation-responsive gene product. This method involves constructing a cell in which cell translation of a FZD nucleic acid changes (i.e., increases or decreases). Specifically, the reporter molecule is encoded by nucleic acid translationally linked to a sequence constructed and arranged to cause a relative increase or decrease in the production of the reporter molecule when transcription of a FZD nucleic acid changes. A gene sequence encoding the reporter may, for example, be fused to part or all of the gene encoding the translation-responsive gene product and/or to part or all of the genetic elements that control the production of the gene product. Alternatively, the translation-responsive gene product may stimulate translation of the gene encoding the reporter, either directly or indirectly. The method further involves contacting the cell with a test compound, and determining whether the test compound increases or decreases the production of the first reporter molecule in the cell.

For these and any method described herein, a wide variety of reporters may be used, with typical reporters providing conveniently detectable signals (e.g., by spectroscopy). By way of example, a reporter gene may encode an enzyme that catalyses a reaction that alters light absorption properties.

Examples of reporter molecules include but are not limited to β-galactosidase, invertase, green fluorescent protein, luciferase, chloramphenicol acetyltransferase, beta-glucuronidase, exo-glucanase, glucoamylase and radiolabeled reporters. For example, the production of the reporter molecule can be measured by the enzymatic activity of the reporter gene product, such as β-galactosidase.

Any of the methods described herein can be used for high throughput screening of numerous test compounds to identify candidate anti-cancer agents. By high-throughput screening is meant that the method can be used to screen a large number of candidate compounds relatively easily and quickly.

Having identified a test compound as a candidate anti-cancer agent, the compound can be further tested in vivo or in vitro using techniques known in the art to confirm whether it is an anti-cancer agent, e.g., to determine whether it can treat cancer, modulate Wnt/FZD signaling, modulate cancer cell motility and/or modulate FZD expression in vitro (e.g., using isolated cells or cell-free systems) or in: vivo (e.g., using an animal, e.g., rodent, model system) if desired.

In vitro testing of a candidate compound can be accomplished by means known to those in the art, such as assays involving the use of cells, e.g., wild type, cancerous and/or transgenic liver cells. Exemplary assays for monitoring Wnt/FZD signaling, FZD expression and cancer cell motility, as well as useful cells that can be used in such assays, are described in the Examples section, below.

Alternatively or in addition, in vivo testing of candidate compounds can be performed by means known to those in the art. For example, the candidate compound(s) can be administered to a mammal, such as a rodent (e.g., mouse) or rabbit. Such animal model systems are art-accepted for testing potential pharmaceutical agents to determine their therapeutic efficacy in patients, e.g., human patients. Animals that are particularly useful for in vivo testing are wild type animals or non-wild type animals (e.g., mice) that over-produce FZD polypeptides, e.g., animals that overexpress a FZD transgene (e.g., a FZD7 transgene) and/or that display reduced production of FZD8 polypeptides. Other animals that are useful for in vivo testing are animals bred to develop liver cancer. Certain particularly useful transgenic mice that develop liver cancer are described in the Examples section and are included in the present invention.

In a typical in vivo assay, an animal (e.g., a wild type or transgenic mouse) is administered, by any route deemed appropriate (e.g., by injection), a dose of a candidate compound. Conventional methods and criteria can then be used to monitor animals for the desired activity. If needed, the results obtained in the presence of the candidate compound can be compared with results in control animals that are not treated with the test compound.

Medicinal Chemistry

Once a compound (or agent) of interest has been identified, standard principles of medicinal chemistry can be used to produce derivatives of the compound for further rounds of testing. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al. (1988) *J. Antibiot.* 41: 1430-8. Furthermore, if the biochemical target of the compound (or agent) is known or determined, the structure of the target and the compound can inform the design and optimization of derivatives. Molecular modeling software is commercially available (e.g., Molecular Simulations, Inc.) for this purpose.

IV. Antibodies

The invention features purified or isolated antibodies that bind, e.g., specifically bind, to a FZD and/or Wnt polypeptide, i.e., anti-FZD and anti-Wnt antibodies. An antibody "specifically binds" to a particular antigen, e.g., a FZD7 and/or 8 polypeptide, when it binds to that antigen, but recognizes and binds to a lesser extent (e.g., does not recognize and bind) to other molecules in a sample. Antibodies of the invention include monoclonal antibodies, polyclonal antibodies, humanized or chimeric antibodies, single chain antibodies, Fab fragments, F(ab')$_2$ fragments, and molecules produced using a Fab expression library.

An example of a type of antibody included in the present invention is the polyclonal anti-FZD7 antibody described in the Examples section, below. Methods for producing polyclonal antibodies are well known to those of skill in the art.

As used herein, the term "antibody" refers to a protein comprising at least one, e.g., two, heavy (H) chain variable regions (abbreviated herein as VH), and at least one, e.g., two, light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of proteins of immunological Interest, Fifth Edition*, U.S. Department of Health and Human Services, NIH Publication No. 91-3242, and Chothia, C et al. (1987) *J. Mol. Biol.* 196:901-917). Each VH and VL is composed of three CDR's and four FRs, arranged from amino-terminus to carboxy-terminus in the following order: FR1, CDR1, FR2, CDR2, FR3, CDR3, FR4.

An anti-FZD or -Wnt antibody can further include a heavy and light chain constant region, to thereby form a heavy and light immunoglobulin chain, respectively. The antibody can be a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2, and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

A "FZD binding fragment" and "Wnt binding fragment" of an antibody refers to one or more fragments of a full-length antibody that retain the ability to specifically bind to FZD or Wnt polypeptides, respectively, or to portions thereof. Examples of polypeptide binding fragments of an antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the terms "FZD binding fragment" and "Wnt binding fragment" of an antibody. These antibody fragments can be obtained using conventional techniques known to those with skill in the art.

To produce antibodies, polypeptides (or antigenic fragments (e.g., fragments of a polypeptide that appear likely to be antigenic by criteria such as high frequency of charged residues) or analogs of such polypeptides), e.g., those produced by recombinant or peptide synthetic techniques (see, e.g., *Solid Phase Peptide Synthesis*, supra; Ausubel et al., supra), can be used. In general, the polypeptides can be coupled to a carrier protein, such as KLH, as described in Ausubel et al., supra, mixed with an adjuvant, and injected into a host mammal. A "carrier" is a substance that confers stability on, and/or aids or enhances the transport or immunogenicity of, an associated molecule. For example, FZD or Wnt proteins, or fragments thereof, can be generated using standard techniques of PCR, and can be cloned into a pGEX expression vector (Ausubel et al., supra). Fusion proteins can be expressed in *E. coli* and purified using a glutathione agarose affinity matrix as described in Ausubel et al., supra.

Typically, various host animals are injected with FZD and/or Wnt polypeptides. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Such procedures result in the production of polyclonal antibodies, i.e., heterogeneous populations of antibody molecules derived from the sera of the immunized animals. Antibodies can be purified from blood obtained from the host animal, for example, by affinity chromatography methods in which FZD and/or Wnt is polypeptide antigens are immobilized on a resin.

The present invention also includes anti-FZD and anti-Wnt monoclonal antibodies. Monoclonal antibodies (mAbs), which are homogeneous populations of antibodies specific for a particular antigen, can be prepared using FZD or Wnt polypeptides and standard hybridoma technology (see, e.g., Kohler et al., Nature, 256:495, 1975; Kohler et al., Eur. J. Immunol., 6:511, 1976; Kohler et al., Eur. J. Immunol., 6:292, 1976; Hammerling et al., In Monoclonal Antibodies and T Cell Hybridomas, Elsevier, N.Y., 1981; Ausubel et al., supra).

Typically, monoclonal antibodies are produced using any technique that provides for the production of antibody molecules by continuous cell lines in culture, such as those described in Kohler et al., Nature, 256:495, 1975, and U.S. Pat. No. 4,376,110; the human B-cell hybridoma technique (Kosbor et al., Immunology Today, 4:72, 1983; Cole et al., Proc. Natl. Acad. Sci. USA, 80:2026, 1983); and the EBV-hybridoma technique (Cole et al., Monoclonal Antibodies and Cancer Therapy, Alan R. Liss, Inc., pp. 77-96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies can be tested for recognition, e.g., specific recognition, of FZD or Wnt polypeptides in an immunoassay, such as a Western blot or immunoprecipitation analysis using standard techniques, e.g., as described in Ausubel et al., supra. Antibodies that specifically bind to FZD or Wnt polypeptides (e.g., FZD7, FZD8, Wnt 3, Wnt 8b and/or Wnt 11) are useful in the invention. For example, such antibodies can be used in an immunoassay to detect the polypeptide in a sample, e.g., a tissue sample.

Alternatively or in addition, a monoclonal antibody can be produced recombinantly, e.g., produced by phage display or by combinatorial methods as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982.

Anti-FZD and -Wnt antibodies can be fully human antibodies (e.g., an antibody made in a mouse which has been genetically engineered to produce an antibody from a human immunoglobulin sequence), or non-human antibodies, e.g., rodent (mouse or rat), rabbit, horse, cow, goat, primate (e.g., monkey), camel, donkey, pig, or bird antibodies.

An anti-FZD and anti-Wnt antibody can be one in which the variable region, or a portion thereof, e.g., the CDRs, is generated in a non-human organism, e.g., a rat or mouse. The anti-FZD and anti-Wnt antibody can also be, for example, chimeric, CDR-grafted, or humanized antibodies. The anti-FZD and anti-Wnt antibody can also be generated in a non-human organism, e.g., a rat or mouse, and then modified, e.g., in the variable framework or constant region, to decrease antigenicity in a human.

Techniques developed for the production of "chimeric antibodies" (Morrison et al., Proc. Natl. Acad. Sci., 81:6851, 1984; Neuberger et al., Nature, 312:604, 1984; Takeda et al., Nature, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778; and 4,946,778 and 4,704,692) can be adapted to produce single chain antibodies specific for a FZD or Wnt polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries can be constructed (Huse et al., Science, 246:1275, 1989) to allow rapid and easy identification of monoclonal Fab fragments with the desired specificity.

Polyclonal and monoclonal antibodies (or fragments thereof) that specifically bind to a FZD and/or Wnt polypeptides can be used, for example, to detect expression of FZD and/or Wnt in various tissues of a patient. For example, a FZD7 and/or 8 polypeptide can be detected in conventional immunoassays of biological tissues or extracts. Examples of suitable assays include, without limitation, Western blotting, ELISAs, radioimmunoassays, and the like.

V. Pharmaceutical Compositions

Any pharmaceutically active compound, agent, nucleic acid, polypeptide, or antibody (all of which can be referred to herein as "active compounds"), can be incorporated into pharmaceutical compositions. Such compositions typically include the active compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition can be formulated to be compatible with its intended route of administration. Examples of routes of administration include enteral (e.g., oral or rectal) and parenteral, e.g., intravenous (e.g., into the portal vein of the liver), intradermal, subcutaneous, transdermal, transmucosal, and pulmonary administration. Administration may be directly into the liver, e.g., by injection or by topical administration during surgery. Solutions or suspensions used for injection can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol and sodium chloride. Prolonged absorption of the injectable compositions can be achieved by including an agent which delays absorption, e.g., aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories (e.g., with conventional suppository bases such as cocoa butter and other glycerides). For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It may be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., liver, in order to minimize potential damage to healthy cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The terms "effective amount" and "effective to treat," as used herein, refer to an amount or concentration of a compound described herein utilized for a period of time (including acute or chronic administration and periodic or continuous administration) that is effective within the context of its administration for causing an intended effect or physiological outcome. For compounds described herein, an effective amount, e.g., of a polypeptide (i.e., an effective dosage), ranges from about 0.001 to 500 mg/kg body weight, e.g. about 0.01 to 50 mg/kg body weight, e.g. about 0.1 to 20 mg/kg body weight. The polypeptide can be administered one time per week for between about 1 to 10 weeks, e.g. between 2 to 8 weeks, about 3 to 7 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a compound can include a single treatment or, preferably, can include a series of treatments.

With respect to antibodies, partially human antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described by Cruikshank et al. ((1997) *J. Acquired Immune Deficiency Syndromes and Human Retrovirology* 14:193).

If the compound is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a FZD or Wnt polypeptide cur nucleic acid, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules (e.g., FZD, e.g., FZD7, DNA) can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. Exemplary constructs that can potentially be used in gene therapy methods are described in the Examples section, below.

The pharmaceutical compositions can be included in a container, pack, or dispenser together with instructions for administration.

VI. Cancer and Treatments Therefor

The term "cancer" refers to animal cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "hapatocellular carcinoma" (HCC) refers to cancer that arises from hepatocytes, the major cell type of the liver.

The term "patient" is used throughout the specification to describe an animal, human or non-human, rodent or non-rodent, to whom treatment according to the methods of the present invention is provided. Veterinary and human clinical applications are contemplated. The term "patient" includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs. The term "treat(ment)," is used herein to denote delaying the onset of, inhibiting, alleviating the effects of, or prolonging the life of a patient suffering from, a condition, e.g., cancer.

Cancers that may be treated using the methods and compositions of the present invention include, but are not limited to, cancers of the liver, stomach, colon, rectum, mouth/pharynx, esophagus, larynx, pancreas, lung, small bowel, and bile ducts, among others.

Individuals considered at risk for developing cancer may benefit particularly from the invention, primarily because prophylactic treatment can begin before there is any evidence of a tumor. Individuals "at risk" include, e.g., individuals exposed to carcinogens, e.g., by consumption, e.g., by inhalation and/or ingestion, at levels that have been shown statistically to promote cancer in susceptable individuals. Also included are individuals exposed to a virus, e.g., a hepatitis virus, e.g., hepatitis B virus (HBV). Also included are individuals at risk due to exposure to ultraviolet radiation, or their environment, occupation, and/or heredity, as well as those who show signs of a precancerous condition. Similarly, individuals in very early stages of cancer or development of metastases (i.e., only one or a few aberrant cells are present in the individual's body or at a particular site in an individual's tissue)) may benefit from such prophylactic treatment.

Skilled practitioners will appreciate that a patient can be diagnosed by a physician (or veterinarian, as appropriate for the patient being diagnosed) as suffering from or at risk for cancer using the methods described herein, optionally using additional methods, e.g., assessing a patient's medical history, performing other diagnostic tests and/or by employing imaging techniques.

One strategy for treating patients suffering from or at risk for cancer is to modulate Wnt/FZD signaling in the patient. The goal is to increase signaling where signaling is too low and to decrease signaling where signaling is too high. Modulation of Wnt/FZD signaling falls into two basic categories: decreasing (i.e., reducing, e.g., eliminating) Wnt/FZD signaling and increasing (i.e., supplementing or providing) Wnt/FZD signaling where there is insufficient or no activity. Whether Wnt/FZD signaling should be inhibited or increased depends upon the intended application. Wnt/FZD signaling can be modulated using the active compounds (e.g., candidate compounds and/or anti-cancer agents) described herein. Compounds that decrease Wnt/FZD signaling activity, e.g., by decreasing expression of FZD7 and/or interfering with an interaction between FZD7 and its ligand (e.g., Wnt 3, 8b and/or 11) can be used, e.g., as treatments for cancer, e.g., liver cancer: Compounds that increase activity, e.g., by increasing expression of FZD8 can also be used, e.g., as treatments for cancer, e.g., liver cancer.

Decreasing Wnt/FZD Signaling

Art-known methods for decreasing the expression of a particular protein in a patient can be used to decrease Wnt/FZD signaling. For example, an antisense nucleic acid effective to inhibit expression of an endogenous FZD gene, e.g., FZD7 gene, can be utilized. As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA.

Antisense molecules are designed so as to interfere with transcription or translation of a target gene (e.g., a gene encoding FZD7 or Wnt 3, 8b or 11) upon hybridization with the target gene or transcript. The antisense nucleic acid can include a nucleotide sequence complementary to an entire FZD or Wnt RNA or only a portion of the RNA. On one hand, the antisense nucleic acid needs to be long enough to hybridize effectively with FZD or Wnt RNA. Therefore, the minimum length is approximately 12 to 25 nucleotides. On the other hand, as length increases beyond about 150 nucleotides, effectiveness at inhibiting translation may increase only marginally, while difficulty in introducing the antisense nucleic acid into target cells may increase significantly. Accordingly, an appropriate length for the antisense nucleic acid may be from about 15 to about 150 nucleotides, e.g., 20, 25, 30, 35, 40, 45, 50, 60, 70, or 80 nucleotides. The antisense nucleic acid can be complementary to a coding region of FZD or Wnt mRNA or a 5' or 3' non-coding region of a FZD mRNA, or both. One approach is to design the antisense nucleic acid to be complementary to a region on both sides of the translation start site of the FZD or Wnt mRNA.

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides complementary to and spanning the length of a FZD mRNA can be prepared, followed by testing for inhibition of FZD or Wnt expression. Optionally, gaps of 5-10 nucleotides can be left between the oligonucleotides to reduce the number of oligonucleotides synthesized and tested.

The antisense nucleic acid can be chemically synthesized, e.g., using a commercial nucleic acid synthesizer according to the vendor's instructions. Alternatively, the antisense nucleic acids can be produced using recombinant DNA techniques. An antisense nucleic acid can incorporate only naturally occurring nucleotides. Alternatively, it can incorporate variously modified nucleotides or nucleotide analogs to increase its in vivo half-life or to increase the stability of the duplex formed between the antisense molecule and its target RNA. Examples of nucleotide analogs include phosphorothioate derivatives and acridine-substituted nucleotides. Given the description of the targets and sequences, the design and production of suitable antisense molecules is within ordinary skill in the art. For guidance concerning antisense nucleic acids, see, e.g., Goodchild, "Inhibition of Gene Expression by Oligonucleotides," in *Topics in Molecular and Structural Biology*, Vol. 12: *Oligodeoxynucleotides* (Cohen, ed.), MacMillan Press, London, pp. 53-77 (1989).

Delivery of antisense oligonucleotides can be accomplished by any method known to those of skill in the art. For example, delivery of antisense oligonucleotides for cell culture and/or ex vivo work can be performed by standard methods such as the liposome method or simply by addition of membrane-permeable oligonucleotides.

Delivery of antisense oligonucleotides for in vivo applications can be accomplished, for example, via local injection of the antisense oligonucleotides at a selected site, e.g., a liver. This method has previously been demonstrated for psoriasis growth inhibition and for cytomegalovirus inhibition. See, for example, Wraight et al., (2001). *Pharmacol Ther.* 90(1):89-104; Anderson et al., (1996) *Antimicrob Agents Chemother* 40: 2004-2011; and Crooke et al., (1996) *J Pharmacol Exp Ther* 277: 923-937.

Similarly, RNA interference (RNAi) techniques can be used to inhibit FZD or Wnt expression, in addition or as an alternative to the use of antisense techniques. For example, small interfering RNA (siRNA) duplexes directed against FZD or Wnt nucleic acids could be synthesized and used to prevent expression of the encoded protein(s).

Another approach to inhibiting Wnt/FZD signaling involves administering to a patient a candidate compound or anti-cancer agent that binds to FZD polypeptides (e.g., FZD7 polypeptides) and/or their binding partners (e.g., Wnt 3, 8b and/or 11), thereby preventing interaction between the two. Such compounds and agents may, for example, bind to the FZD polypeptide (e.g., to the CRD domain of the FZD polypeptide) and/or to the Wnt polypeptide (e.g., to a binding domain of the Wnt polypeptide) in such a way that interaction between the proteins is prevented. Such candidate compounds and anti-cancer agents can be identified using screening methods described herein. An example of a compound that can bind to a Wnt polypeptide, e.g., Wnt 3, 8b and/or 11, is a FZD7 receptor or truncated form thereof, as described in the Examples section, below.

Yet another approach to inhibiting Wnt/FZD signaling involves administering to a patient a vector (e.g., a gene therapy vector) that encodes a mutated (e.g., truncated) form of a FZD receptor, e.g., a FZD7 receptor. Expression of the mutated form of the receptor by the patient's cells that incorporate the construct can interfere with Wnt/FZD signaling in the cells. For example, a construct that encodes a secreted and soluble form of a FZD receptor (e.g., a FZD7 receptor) can be used. Expression of such a construct by target cells would cause the cells to secrete a soluble form of the FZD receptor that would bind Wnt polypeptides, rendering them unable to bind to intact FZD receptors on the cell surface. Alternatively or in addition, a construct that encodes a membrane bound but inactive form of a FZD receptor (i.e., a mutant FZD receptor unable to perform some function performed by a counterpart wild-type FZD receptor) can be used. Expression of such a construct by target cells may bind up Wnt polypeptides or interfere with Wnt/FZD signaling via an internal mechanism not involving Wnt polypeptides. The vector can be derived from a non-replicating linear or circular DNA or RNA vector, or from an autonomously replicating plasmid or viral vector. Methods for constructing suitable expression vectors are known in the art, and useful materials are commercially available. Exemplary expression vectors that encode useful mutated FZD7 polypeptides are described in the Examples section, below.

Increasing Wnt/FZD Signaling

New or supplemental Wnt/FZD signaling can be provided in vivo by increasing expression of FZD polypeptides (e.g., FZD8 polypeptides) in the patient. For example, a FZD polypeptide can be generated directly within an organism, e.g., a human, by expressing within the cells of the organism a nucleic acid construct containing a nucleotide sequence encoding a FZD polypeptide (e.g., a FZD8 polypeptide). Any appropriate expression vector suitable for transfecting the cells of the organism of interest can be used for such purposes.

VII. Transgenic Animals

The present invention also features transgenic animals that develop liver cancer and overexpress FZD7 in their liver cells. Such animals represent model systems for the study of liver cancer and for the development of therapeutic agents that can modulate Wnt/FZD signaling and treat cancer.

Transgenic animals can be, for example, farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats).

Any technique known in the art can be used to introduce transgenes into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983). Especially useful are the methods described in Yang et al. (*Proc. Natl. Acac. Sci. USA* 94:3004-3009, 1997).

For a review of techniques that can be used to generate and assess transgenic animals, skilled artisans can consult Gordon (*Intl. Rev. Cytol.* 115:171-229, 1989), and may obtain additional guidance from, for example: Hogan et al. *Manipulating the Mouse Embryo*, Cold Spring Harbor Press, Cold Spring Harbor, N.Y., 1986); Krimpenfort et al. (*Bio/Technology* 9:86, 1991), Palmiter et al. (*Cell* 41:343, 1985), Kraemer et al. (*Genetic Manipulation of the Early Mammalian Embryo*, Cold Spring Harbor Press, Cold Spring Harbor, N.Y., 1985), Hammer et al. (*Nature* 315:680, 1985), Purcel et al. (*Science,* 244:1281, 1986), Wagner et al. (U.S. Pat. No. 5,175,385), and Krimpenfort et al. (U.S. Pat. No. 5,175,384).

Methods for constructing a transgenic animal that develops liver cancer are also described below in the Examples section. A particularly useful transgenic animal is the IRS-1/c-myc double transgenic mouse described therein. Such transgenic animals are included within the present invention.

EXAMPLES

The invention is illustrated in part by the following examples, which are not to be taken as limiting the invention in any way.

Example 1

Functional Consequences of Frizzled-7 Receptor Overexpression in Human Hepatocellular Carcinoma HCC Tumors and Cell Lines HCC tumor tissues were obtained from 30 males in Taiwan and South Africa. Samples were obtained from sixteen individuals from Taiwan, all of whom had HBV-related disease. These sixteen individuals had undergone surgery for resection of tumor. There were fourteen samples from South African individuals who were 28-57 years old. Of these, ten had HBV-, one had HCV-, and two had hemochromatosis-related HCC. One individual's HCC was of unknown etiology. There was a matched uninvolved nontumorous liver sample for all 30 HCC. Cirrhosis and/or fibrosis was present in 85%. Huh7, Focus, HepaRG[19], Hep3B, and HepG2 hepatoma cell lines were grown in minimum essential medium Eagle (MEM) (Cellgro), and PLC/PRF/5 in DMEM (Cellgro), supplemented with 10% (vol/vol) fetal calf serum (FCS) (Sigma), 1×-MEM non-essential amino acid solution (Sigma), and 1% (vol/vol) penicillin/streptomycin (Sigma).

Real-Time RT-PCR Assay

The copy number of FZD7 mRNAs was quantified in unknown samples by measuring the $C_t$ value followed by normalization to 18S ribosomal RNA (18S rRNA) after comparison to a standard curve for both FZD7 and 18S rRNA. This ratio of FZD7/18S rRNA was subsequently normalized to a calibrator (mean value obtained from normal livers) and expressed as relative abundance of FZD7 mRNA. Standards were prepared with 10-fold dilutions of the corresponding PCR products cloned into the pCR®2.1 Vector (Invitrogen, Life Technology). The specificity of the FZD7 and 18S rRNA inserts was provided by sequence analysis. Serial dilution of FZD7- and 18S rRNA-plasmids were aliquoted and stored at −20° C. until use. Primers were selected using the Primer3 website (www-genome.wi.mit.edu/cgi-in/primer/primer3_www.cgi). Primers for FZD7 and 18S rRNA respectively (Invitrogen™ Life Technologies) were as follows: (a) FZD7, 5'-GCCGCTTCTACCACAGACT-3' (SEQ ID NO:28; forward) and 5'-TTCATACCGCAGTCTCCCC-3' (SEQ ID NO:29; reverse) to yield a 54 bp amplicon; (b) human 18S rRNA, 5'-GGACACGGACAGGATTGACA-3' (SEQ ID NO:30; forward) and 5'-ACCCACGGAATC-GAGAAAGA-3' (SEQ ID NO:31; reverse) to give a 50 bp amplicon. BLASTN searches were conducted against dbEST and nr (the nonredundant set of GenBank database sequences) to confirm the gene specificity of the nucleotide sequences chosen for the primers to confirm the lack of DNA polymorphism.

Total RMA was extracted from liver specimens and HCC cell lines by using TRIzol® reagent (Invitrogen, Life Technology). The quality of the RNA samples was determined by electrophoresis through agarose gels and staining with ethidium bromide; the 18S and 28S ribosomal RNA bands were visualized under UV light. A total amount of 250 ng total RNA was treated with DNase-I, RNase-free, and reverse transcribed with random hexamers and the AMV reverse transcriptase, all from Roche Diagnostics Corporation (Indianapolis, USA). All PCR reactions were performed using an iCycler iQ™ Multi-Color Real Time PCR Detection System (Bio-Rad, Hercules, USA) with a mix composed of 1×SYBR® Green PCR Master Mix (Applied Biosystems, USA), 500 nM each primer, and 5 ng cDNA (equivalent total RNA) from unknown samples. The thermal cycling conditions comprised an initial step at 95° C. for 10 minutes, followed by 40 cycles at 95° C. for 15 seconds and 60° C. for 1 minute. Experiments were performed in duplicate. Each PCR run included FZD7 and 18S standard curves, a non-template control, and the unknown cDNAs analyzed for FZD7 and 18S rRNA copy numbers.

Cell Motility Assay

A luminescence-based assay was used to evaluate cell motility and migration. This assay assesses non-migrated, migrated-adherent, and migrated non-adherent hepatoma cells through uncoated polyvinylpyrrolidone-free polycarbonate filters as previously described[14] in chambers partitioned with 13 mm diameter, 8 µM pore polycarbonate membranes (Osmonics, Inc.). After 72 hours of growth in 1% FCS, cells were re-suspended in serum-free medium with soybean trypsin inhibitor (Sigma) at 0.5 mg per mL. In the lower chamber, collagen-I (Sigma) was diluted to 100 µg/mL in 200 µL of serum-free medium.[8] After assembly of the chambers, $1 \times 10^5$ of the resuspended cells were added to the upper chamber, and incubated for 3 hours in a $CO_2$ humidified incubator to allow cell migration to proceed. The cells remaining on the upper surface of the membrane (non-migrated) were harvested with a sterile cotton swab and placed into a well containing ATP lysis buffer (Packard Instrument Company, Meriden, Conn.). To harvest migrated adherent cells, the membrane (devoid of non-migrated cells) was placed into another well containing ATP lysis buffer. The migrated non-adherent cells were harvested by re-suspending the cells in the lower compartment of the blind chamber and placing them into a third well containing ATP lysis buffer. ATPLite substrate was added to each well and luminescent counts per second were measured in a TopCount Microplate reader (Packard instrument Company). The results were analyzed using Excel (Micro soft Corp., Seattle, Wash.) to calculate percentages of non-migrated, migrated-adherent, and migrated non-adherent cells in each assay.

Transfection and Retroviral Transduction

Because the N-terminal ectodomain of Frizzled receptors functions as a natural antagonist of Frizzled-mediated signal transduction, a mutant cDNA with a C-terminal truncation (FZD7-ΔTΔC) was generated as previously described.[44] The cDNA FZD7-ΔTΔC cDNA was subcloned into a pcDNA3 mammalian expression vector (Invitrogen) and certified for protein expression by an in vitro translation reaction.[44] The in vitro effect of stable expression of FZD7-ΔTΔC was examined in human hepatoma cells. The pcDNA3/FZD7-ΔTΔC, and pcDNA3/empty vectors were transfected by electroporation (250V voltage/15 millisecond pulse with Gene Pulser II, BioRad). Stable transfectants were selected with 800 µg/ml Geneticin (Gibco) added to the culture medium. Expression of the FZD7-ΔTΔC gene was assessed by quantitative real-time RT-PCR and Western blot analysis.

Two different FZD7 truncated mutants either with deletions in the intracellular domain alone (FZD7-ΔC) or in both the intracellular and transmembrane domains (FZD7-ΔTΔC) as well as a GFP control, were prepared by PCR using the Pfu-polymerase (Stratagene). Constructs were cloned into the lentiviral pLenti6/V5 Directional TOPO® vector (Invitrogen) downstream of the cytomegalovirus promoter. All constructs were verified by sequence analysis of both strands. Virions were produced in 293FT cells, aid viral stocks were frozen at –80° C. Hepatoma cells were transduced at a MOI of 5, and stable clones were selected in the presence of blasticidin (4 µg/mL). Quantitative real-time RT-PCR and Western blot analysis were used to detect gene expression. A mutant construct of β-catenin with biologic activity (ΔN/ΔC) was prepared by PCR using the Pfu-polymerase (Stratagene) as previously described[2] and following transfection, HCC motility was assessed 72 hours later.

Transient transfection assays were performed to assess for Tcf transcriptional activity. In brief, cells were seeded in 6 well plates at a density of $3 \times 10^5$ cells/well the day prior to transfection. Transfections were performed with either TOPflash (Tcf Reporter Plasmid) or FOPflash (mutant Tcf binding sites) and β-galactosidase expressing plasmid in triplicate using Lipofectamine 2000 (Life Technologies, Inc., Rockville, Md.). Focus, Huh7 and Hep3B cells were harvested 48 hours after transfection and luciferase activity was measured by a luminometer TopCount microplate reader (Packard Instrument Co.). Transfection efficiency was normalized by measurement of β-galactosidase activity. The experiment was performed three times.

Immunoprecipitation

Transfected cells were washed with cold phosphate-buffered saline, and pelleted at 2,000 rpm for 5 minutes and resuspended in 500 µl of solubilization buffer (136 mM NaCl, 2.7 mM KCl, 12 mM $Na_2HPO_4$, 1.8 mM $KH_2PO_4$, pH 7.4, 1% NP-40 with protease inhibitors). Lysates were incubated for 3 hours at 4° C. on a rocker platform and then microcentrifuged at 13,000 rpm for 15 minutes at 4° C. to pellet-out cell debris. Lysates were immunoprecipitated in a 1.0-ml total volume with 500 µL of lysate, 480 µL of solubilization buffer, and 20 µL of goat anti-human V5 antibodies coupled to agarose beads (Bethyl Laboratories, Inc.) for 12 hours at 4° C. with constant shaking. The beads were washed twice with the solubilization buffer. Bound proteins were eluted by boiling for 5 minutes in SDS sample buffer. The proteins were separated on 10% polyacrylamide gel, transferred to PVDF membrane (NEN™ Life ScienceProducts, Boston, Mass.).

Protein Extraction and Western Blot Analysis

For whole protein extraction, hepatoma cells at 50% confluence were homogenized in lysis buffer [30 mM Tris (pH 7.5), 150 mM NaCl, 1% NP-40, 0.5% Na deoxycholate, 0.1% SDS, 10% glycerol, and 2 mM EDTA] with protease inhibitors (Roche Molecular Biochemicals) and sonicated. Protein concentration was determined with the BCA Protein Assay Kit (Pierce) using BSA as standard. Subcellular fractionations were performed as previously described.[33]

Aliquots of proteins were resolved on SDS/PAGE and transferred onto PVDF membranes (NEN™ Life ScienceProducts, Boston, Mass.) by electroblotting. The membranes were blocked with 5% nonfat dry milk in Tris-buffered saline containing 0.1% Tween 20 and then probed with a mouse monoclonal anti-β-catenin antibody diluted at 1:500 (Transduction Laboratories), or a mouse monoclonal anti-PCNA antibody diluted at 1:1,000 (Oncogene Science). A specific rabbit polyclonal antibody was prepared against a human FZD7 peptide QNTSDGSGGPGGGPTAYPTAPYLPD (SEQ ID NO:32), amino acids 163-187 (NCBI Protein database accession no. BAA_34668) and used at 1:5,000 dilution. Each primary antibody was followed by incubation with a secondary horseradish peroxidase antibody diluted 1:10,000 and then revealed with the chemiluminescence imaging Western Lightning (PerkinElmer™Life Sciences, Boston, Mass.). The specificity of the antigen-antibody interaction was established by absorption of FZD7 immunoreactivity with specific and not with non-relevant peptides as well as lack of FZD7 protein detection with addition of second antibody alone (data not shown). All of the blots were standardized for equal protein loading by Ponceau S red staining.

Sequencing

PCR amplification of β-catenin exon-3, which contains the 4 potential sites for phosphorylation by GSK-3β, was performed on the cDNAs derived from each tumor sample using a β-catenin exon-2 forward primer, and a β-catenin exon-4 reverse primer as previously described.[35] After resolution of the PCR products by 2% agarose gel electrophoresis and visualization with ethidium bromide, PCR products were excised and cloned into the pCR®2.1 Vector (Invitrogen, Life Technology). Sequencing was performed in both directions using T7 forward and M13 reverse primers.

Statistical Analysis

The dependent or independent t-tests were used for continuous data with StatView Software Version 5.0 (SAS Institute Inc.). Tests were considered significant when their P values were <0.05.

Real-Time RT-PCR Assay for FZD7

Random hexamers were used for the initial reverse transcription step. The amplification was performed with set of primers generating a small amplicon size (around 50 bp) for both FZD7 and 18S rRNA. FIG. 1 shows the standard curves for the FZD7 and 18S rRNA and illustrates the values obtained for unknown tumor samples. A linear relationship between the $C_t$ and the log of the starting copy number was demonstrated ($R_2 \geq 0.99$). The efficiency of the reaction (E), calculated by the formula: $E=10_{1/m}-1$, where in is the slope of the standard curve,[4] ranged from 90 to 100% in the assays performed at different times. The same features with respect to the dynamic range and efficiency of the reactions were observed with serial dilutions of cDNAs derived from the Huh7 cell line, or from human HCC tumors when using 10 to 0.625 ng of equivalent total RNA (data not shown). Sensitivity was <10 copies per reaction for FZD7 and 100 copies for 18S rRNA.

FZD7 gene expression was measured in HepG2, Hep3B, HepaRG, PLC/PRF/5, Focus, and Huh7; values obtained on four normal adult liver tissues served as a controls and the mean value of these normal livers served as a calibrator for normalization of FZD7 mRNA levels in other unknown samples. All cell lines were found to express FZD7 mRNA gene at higher levels than normal liver (FIG. 1C). Huh7, PLC/PRF/5, and Focus cells exhibited the highest levels of FZD7 mRNA with ratios of 354, 116, and 8, respectively, compared to normal livers. In contrast, Hep3B, HepaRG, and HepG2 had lower levels of expression with ratios of 15, 11, and 9 respectively.

Correlation of Steady State FZD7 mRNA Levels and HCC Motility

Figure 2:
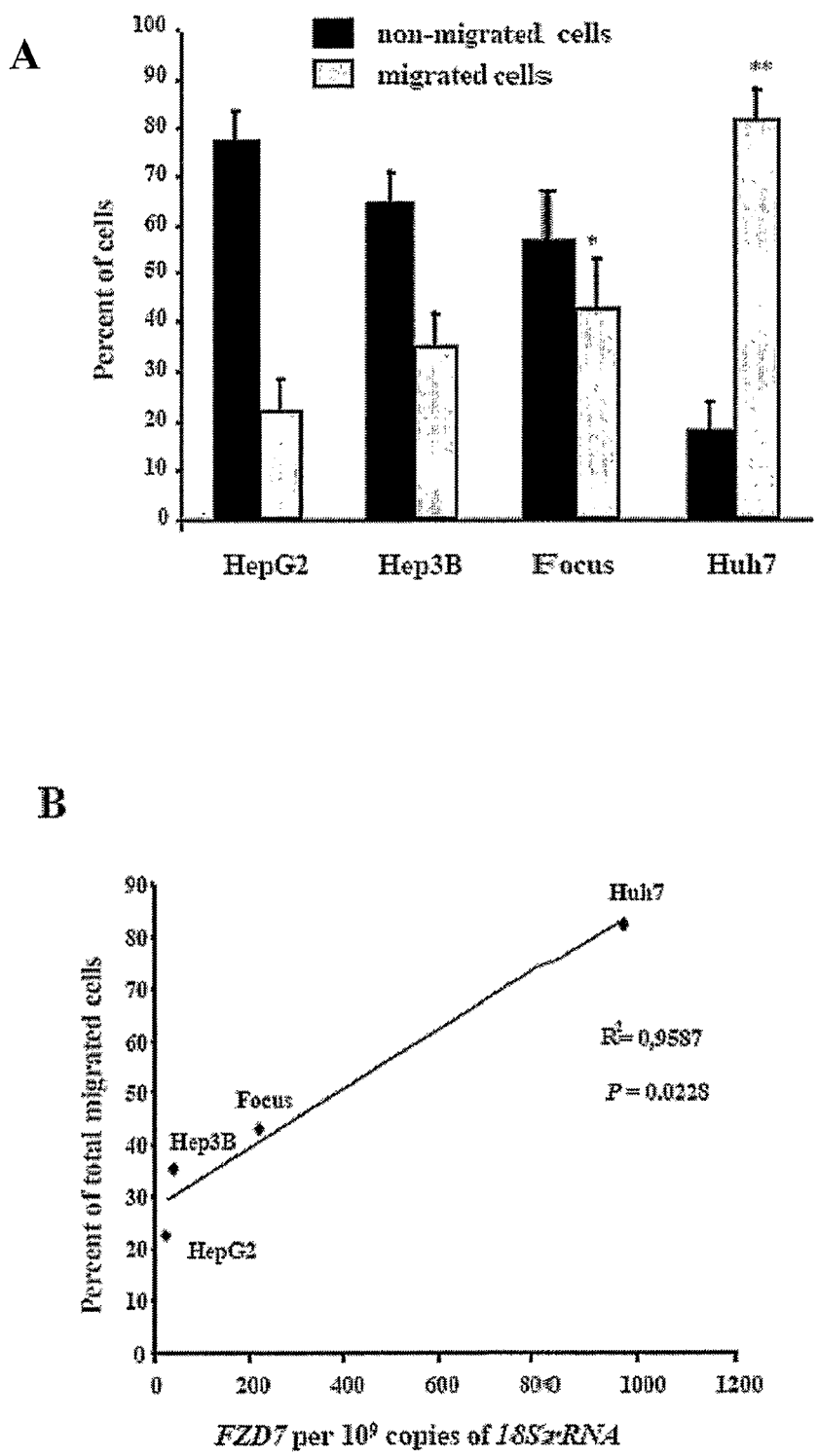
FIGS. 2A-2B are graphs that illustrate measurements of HCC cell motility.

Because the Wnt-Frizzled signal transduction pathway is involved in cell motility and migration,[46] motility of HepG2, Hep3B, Focus, and Huh7 cells in the context of FZD7 gene expression was examined. Fetal calf serum was not used as chemoattractant[14] since serum growth factors may interfere with β-catenin stabilization independent of the Wnt-Frizzled signals.[34,43] Under the experimental conditions of using soluble collagen-I as a chemoattractant, a significant correlation between FZD7 steady state mRNA levels and percent of total migrated cells (both adherent and nonadherent) was observed (FIGS. 2A and 2B). The highest FZD7 mRNA levels and motility rates were found in Huh7 cells.

Subcellular Localization of β-catenin

Figure 3:
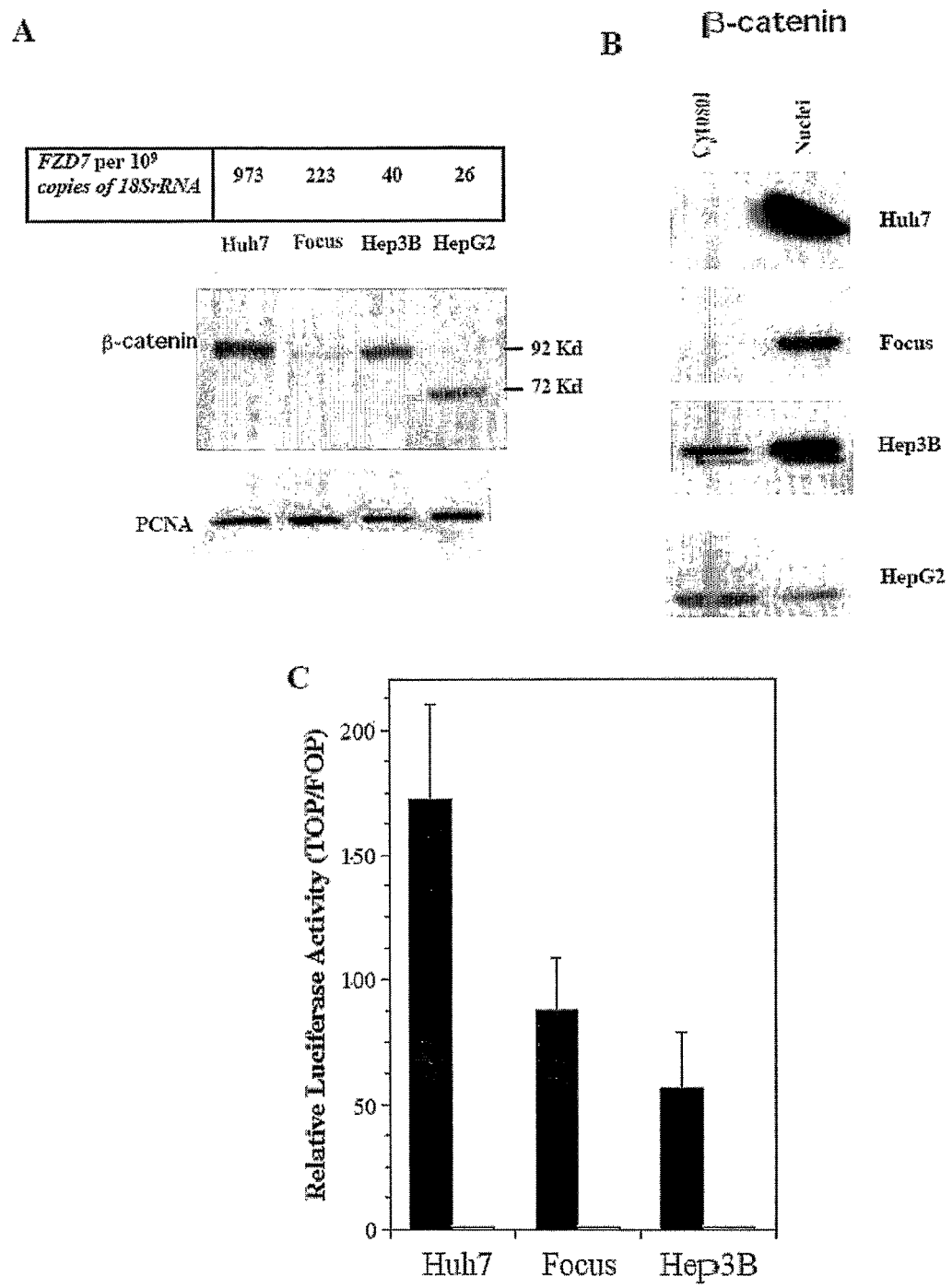
FIGS. 3A-3C are Western blots and a graph illustrating an analysis of total cellular β-catenin and Tcf reporter assay. There is no correlation of PCNA with FZD7 mRNA (FIG. 3A). However, high levels of FZD7 gene expression are associated with nuclear accumulation of β-catenin; lower FZD7 expression levels were associated with both nuclear and cytoplasmic accumulation in HepG2 and Hep3B cells (FIG. 3B).

To explore the hypothesis that Wnt-Frizzled signal may act through the canonical β-catenin pathway to control cellular motility, the β-catenin status in HCC cell lines was evaluated. It was found that Huh7, Focus, and Hep3B cells have a homozygous wild-type β-catenin as described previously.[5] HepG2 cells have a heterozygous deletion in exon-3 and make both wildtype and mutant β-catenin proteins.[9] β-catenin may be bound to either the cytosolic GSK3β/Axin/APC complex or membrane-linked with E-cadherin or c-Met.[34] Upon signaling by Wnt through its Frizzled receptor and subsequent interaction with dishevelled, the GSK3β/Axin/APC/β-catenin complex undergoes dephosphorylation causing β-catenin dissociation from the complex, followed by its nuclear translocation. Thus nuclear versus cytosolic localization of wild-type β-catenin was explored in these HCC cell lines. The β-catenin protein levels are shown in FIG. 3A. It was of interest that two HCC cell lines namely Huh7 and Focus with the highest FZD7 gene expression, had a striking nuclear subcellular localization of wild-type β-catenin (FIG. 3B). Furthermore, the levels of FZD7 mRNA appear to not correlate with the cellular proliferation index as assessed by levels of proliferating cell nuclear antigen (PCNA) (FIG. 3A).

In addition, Huh7, Focus and Hep3B showed high basal Tcf transcriptional activity and there was a general correlation between the level of Tcf transcriptional activity and FZD7 receptor expression (FIG. 3C). These results are also consistent with the levels of β-catenin found within the cell and its nuclear localization. These findings suggest that activation of the canonical Wnt/β-catenin pathway is involved in the multi-step process of hepatocyte transformation.

Figure 4:
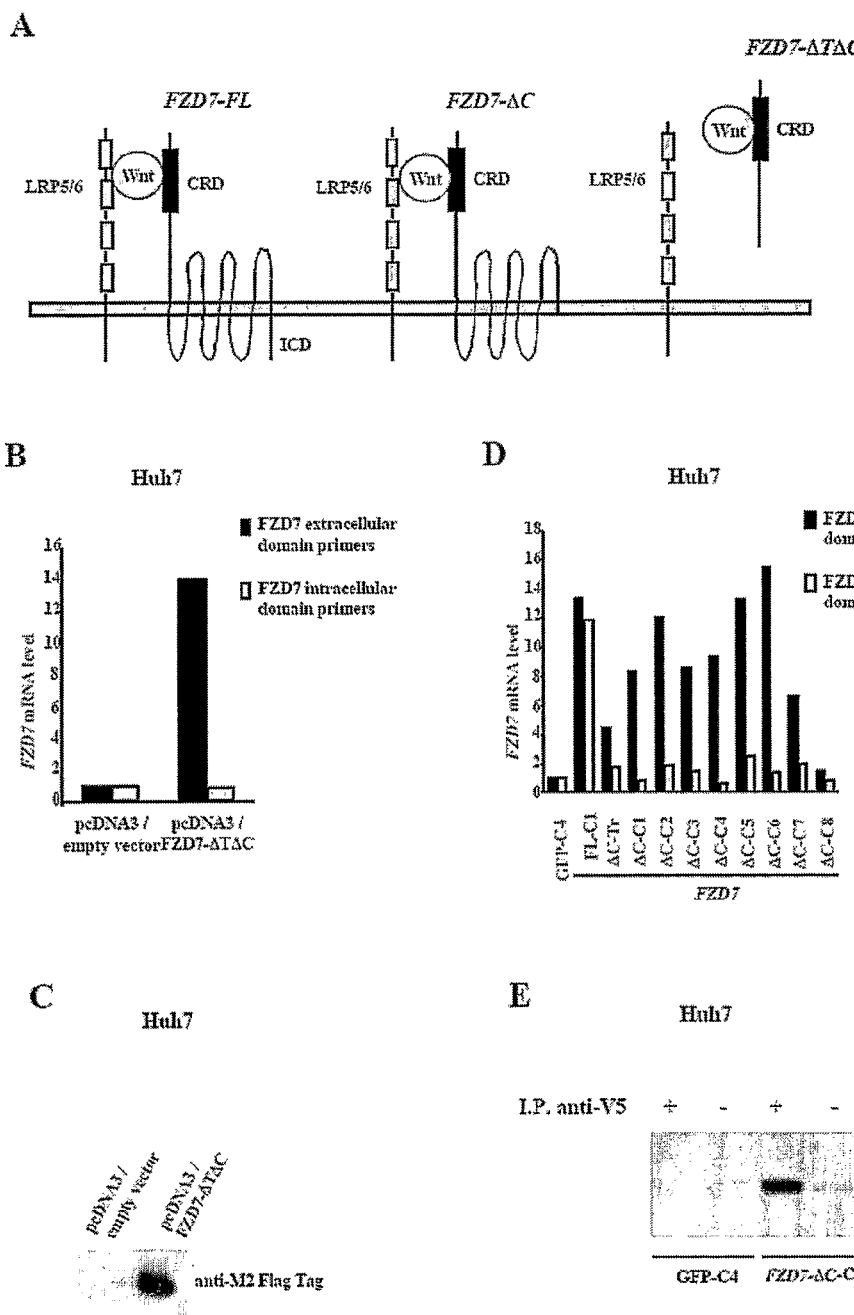
FIGS. 4A-4E are diagrams, graphs and Western blots illustrating construction and expression of FZD7 mutant proteins.

Expression of a Dominant-Negative FZD7 Receptor Mutants Inhibits Wild-Type—Catenin Accumulation and Motility of HCC Cells The motility and accumulation of wild-type β-catenin was assessed in human HCC cell lines after down-regulation of the Wnt-FZD7 signal following ectopic expression of two types of dominant negative FZD7 mutant receptors: 1) The FZD7-ΔTΔC represents a secreted FZD7 receptor where both intracellular and transmembrane domains have been truncated; this construct inhibits Wnt signaling in human esophageal carcinoma cell lines,[44] and 2) the FZD7-ΔC construct where the transmembrane FZD7 receptor has been truncated in the intracellular domain only as depicted in FIG. 4A. Since FZD7-ΔTΔC receptor acts as a soluble Wnt ligand binding protein, studies were performed on a heterogenous population of stably transfected cells. HCC cells were selected in the presence of geneticin and subsequently evaluated for motility and accumulation of wild-type β-catenin. The FZD7-ΔC mutant receptor does not act as a soluble ligand but is closely linked to the membrane with its 7 transmembrane domains. The FZD7-ΔC cDNA was cloned into the lentiviral vector pLenti6/V5-D-TOPO® to allow for a high transduction efficiency in both dividing and non-dividing cells. Preliminary experiments with a similarly cloned GFP construct indicated that over 80% of human HCC cells will abundantly expresse GFP from 72 hr to 3 weeks post-transduction. Ectopic expression of FZD 7-ΔC and FZD7-ΔTΔC was assessed by Western blot and quantitative real-time RT-PCR using different set of primers targeting specifically either the extracellular or the intracellular domain of FZD7, allowing to differentially assess the ectopic expression of FZD 7-ΔC and FZD 7-ΔTΔC by comparison to the endogenous expression of the wild-type full-length FZD7 receptor (FIGS. 4B, 4C, 4D, and 4E).

Figure 5:
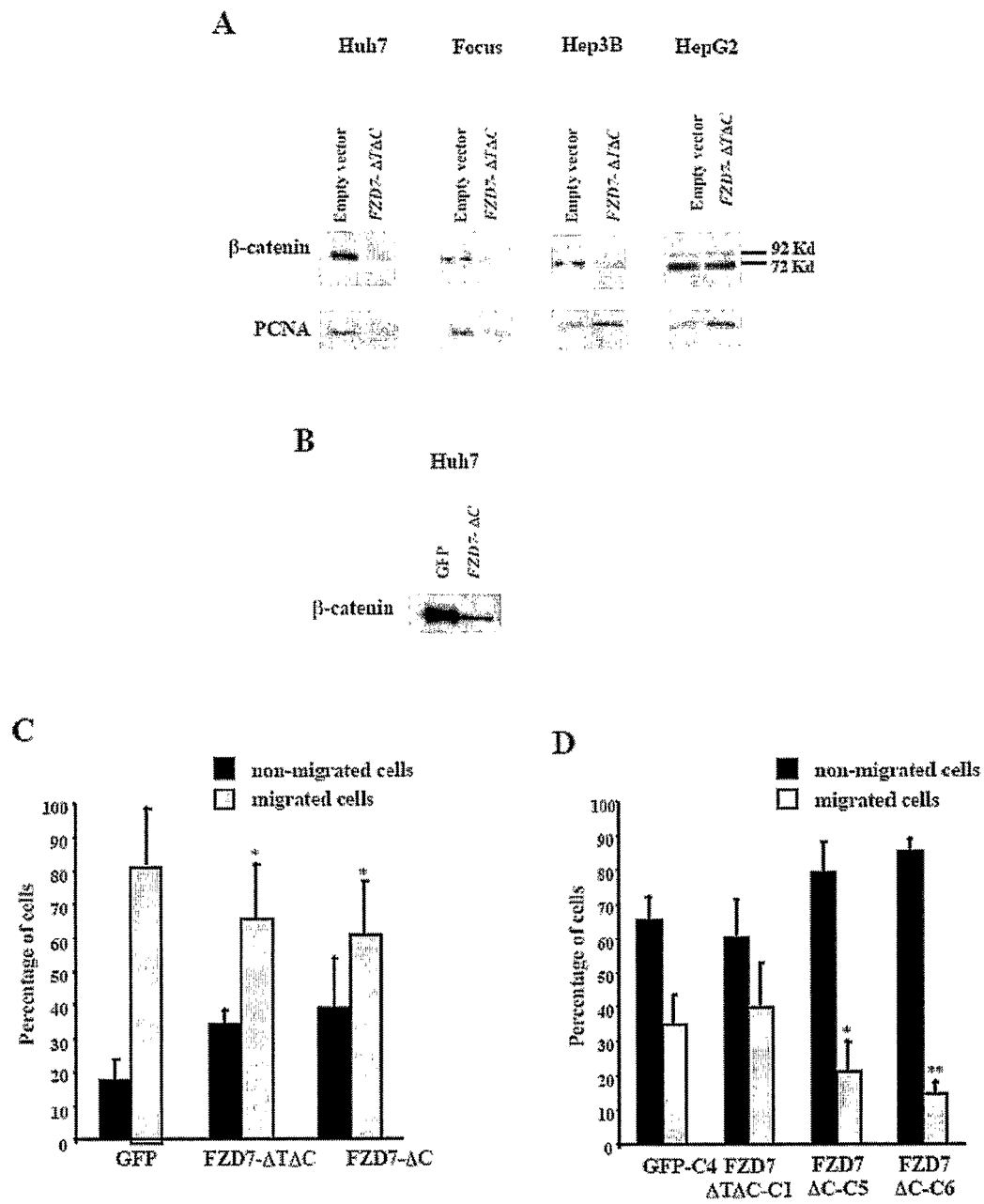
FIGS. 5A-5D are Western blots and graphs illustrating β-catenin protein levels in HCC cells after ectopic expression of a dominant negative FZD7-ΔTΔC mutant receptor expressing construct.

The secreted FZD 7-ΔTΔC ectodomain is a functional antagonist of endogenous FZD7 signaling by suppression of the interaction of APC with β-catenin in the KYSE150 esophageal carcinoma cell line.[44] Results herein demonstrate that ectopic expression of FZD7-ΔTΔC or FZD 7-ΔC causes a decrease of β-catenin protein levels in all HCC cell lines with a homozygous wild-type β-catenin gene presumably through down-regulation of the Wnt-FZD7 signal transduction cascade (FIGS. 5A and 5B). In contrast, β-catenin mRNA steady state levels were not altered by transfection of the dominant negative mutant constructs as assessed by real-time RT-PCR (data not shown). However, no effects of these mutant receptor constructs were observed on β-catenin levels in HepG2 cells which have a heterozygous β-catenin deletion (FIG. 5A).

If FZD7 is potentially involved in cellular motility via the canonical β-catenin pathway, it became important to evaluate the impact of down-regulation of the Wnt-FZD7 signal on motility of Huh7 cells.[35] Results herein demonstrate that ectopic expression of the transmembrane anchored FZD7-ΔC mutant receptor was very effective in reducing the number of motile Huh7 cells under conditions of transient expression as shown in FIG. 5C. In addition, this construct was more efficient in reducing motility than the secreted FZD7-ΔTΔC mutant receptor. These observations were further confirmed by striking inhibitory effects on cell motility by two independent stable clones expressing either FZD 7-ΔC at high levels (FZD 7-ΔC-C5, and FZD7-ΔC-C6 respectively), compared to a FZD7-ΔTΔC expressing clonal cell line (FZD7-ΔTΔC-C1) as shown in FIG. 5D.

In order to establish a clear link between regulation of the canonical Wnt/β-catenin pathway and the FZD7-mediated alteration of cell motility in Huh7 cells, experiments were performed to restore cell motility by ectopic expression of a mutant β-catenin construct in Huh7 cells harboring a low motility phenotype due to overexpression of a dominant-negative FZD7receptor mutant protein. A pLenti6/V5-D-TOPO® lentiviral vector expressing the ΔN/ΔC β-catenin mutant was generated (FIG. 6A) that had been previously shown to exhibit transactivating properties on Lef/Tcf regulated target genes in HEK cells.[2] The FZD7-ΔC-C6 and GFP-C4 blasticidin-selected clonal Huh7 cell populations were co-transduced by the ΔN/ΔC β-catenin mutant lentivirus construct or GFP as a control to keep constant the total amounts of plasmid DNA within Huh7 cells. In this context, the motility of co-transduced Huh7 cells was assessed and demonstrated that the low motility phenotype induced by stable FZD7-ΔC expression could be reversed by ectopic expression of the ΔN/ΔC mutant β-catenin protein (FIG. 6B). These experiments further support a role for activation of the canonical Wnt/β-catenin pathway during hepatic oncogenesis in cells overexpressing FZD7 receptors.

FZD7 mRNA is Overexpressed in Human HCC Tumors

Figure 7:
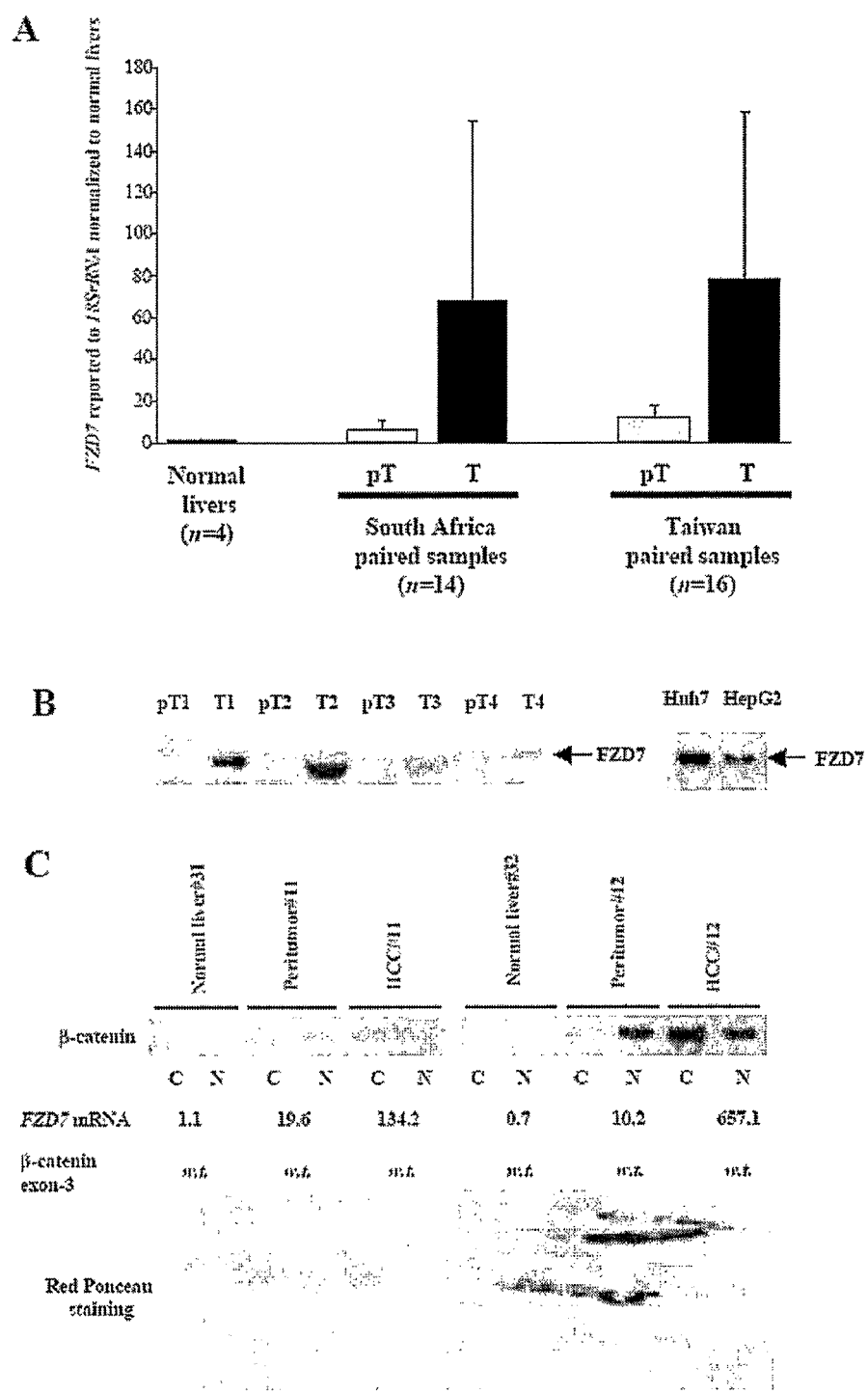
FIGS. 7A-7C are a graph and Western blots illustrating FZD7 expression in human HCC tumors and peritumerous liver parenchyma.

Normal liver showed low FZD7 mRNA expression (FIG. 7A and Table 1, below). Among 30 paired samples tested from two regions of the world, 27 (90%) displayed significant FZD7 overexpression in comparison to corresponding peritumorous areas (non-parametric paried test, p<0.0001; paried t-test, p=0.0187) (FIG. 7A). These findings were confirmed at the protein level by Western blot analysis (FIG. 7B). Results were similar between tumors derived from South Africa, and Taiwan with an average increase of 12 fold between tumor and peritumorous areas. High levels of FZD7 mRNAs as defined by a value above the cut-off (mean of normal liver±3 SD, α=0.01) were observed in 29 tumors (97%), and 23 peritumoral areas (77%) compared to completely normal adult liver controls. These observations led us to believe that FZD7 mRNA up-regulation may be an early event occurring in the preneoplastic peritumorous area of the liver.

Similar to the in vitro observations in HCC cell lines, β-catenin levels in comparison to FZD7 gene expression was explored in human tumors. It was found that, among 5 different HCC expressing FZD7 mRNA at >100-fold above the mean of normal livers, 4 of the 5 HCC were associated with a homozygous wild-type β-catenin exon-3 gene. However, one tumor (HCC #28) had a heterozygous deletion of one β-catenin allele similar to that found in the HepG2 cell line. Western blot analysis of cytosolic and nuclear enriched fractions demonstrated that wild-type β-catenin protein also accumulates in HCC and peritumorous areas in the context of elevated FZD7 mRNA expression and in the absence of β-catenin exon-3 mutations as shown in FIG. 7C. The findings in human tumors, therefore, confirm our in vitro observations in HCC cell lines.

Discussion

The data herein provide direct evidence by real-time RT-PCR that FZD7 receptor gene expression is commonly up-regulated in an early event during the development of HCC. A rabbit polyclonal antibody to a unique peptide of FZD7 was developed to confirm that this receptor is also up-regulated at the protein level as well by Western blot analysis. The biologic consequences of this event are the stabilization of wild-type β-catenin and enhanced tumor cell migration.

Activation of cellular oncogenes (i.e., c-myc),[49] growth factors (i.e., insulin-like growth factor II and transforming growth factor type α)[7,15,48] in association with mutations of tumor suppressor genes (i.e., P53, RB, and IGFIIR)[15,23,50] have been described in human and animal models of HCC. However, these genetic events are present in <50% of HCC tumors and usually occur late in the multistep process of hepatocarcinogenesis and not in precancerous lesions of dysplasia, cirrhosis, and non-cirrhotic chronic hepatitis. More recently, aberrant accumulation of the potential oncogenic β-catenin protein, due to mutations of the gene has been found in both human and murine HCC tumors but such mutations are unusual (15% of HCCs) and of late occurance since they are absent in dysplasia, cirrhosis or liver fibrosis.[13,16]

Additional studies have revealed that in 35-80% of HCC, aberrant accumulation of β-catenin is not associated with mutations of β-catenin, Axin1 or APC genes of this Wnt inducible signal transduction pathway.[12,17,24,30,47] Although p53 gene mutations could contribute, in part, to aberrant accumulation of wild-type β-catenin, the frequency of gene mutations is relatively low. The level of nuclear and cytoplasmic β-catenin accumulation in such tumors therefore remains unexplained.[5] The possibility that other members of the Wnt/β-catenin signal transduction pathway could contribute to aberrant accumulation of wild-type β-catenin in HCC cells was explored. During initiation of the Wnt signaling cascade, binding of a Wnt ligand to its target, the Frizzled receptor, may lead either to the stabilization of intracellular β-catenin protein[20] or activation of downstream molecules such as c-Jun NH$_2$-terminal kinase (JNK) and protein kinase C.[29] However, if Frizzled receptors were overexpressed, this signal transduction pathway might be constitutively activated. Human HCC cell lines, as well as tumors were evaluated, and the biologic consequences of FZD7 overexpression were assessed.

All HCC cell lines were found to overexpress the FZD7 gene at different levels. Indeed analysis of human liver tumors showed frequent FZD7 gene up-regulation as compared with normal liver, and adjacent uninvolved areas. The general finding of significant overexpression in "pre-neoplastic" peritumoral tissue as compared to normal liver suggests that up-regulation of this gene may be an early event in hepatocarcinogenesis. Once complete transformation has occurred, higher levels of FZD7 were observed. These results suggest that activation of the Wnt/β-catenin signaling due to FZD7 receptor overexpression alone or possibly in association with LRP-coreceptor and Wnt ligand expression or overexpression, may be one of the major early events of the stepwise process leading to hepatocyte transformation.

Activation of the canonical Wnt pathway results in accumulation of the free β-catenin pool in the cytoplasm. After forming a transcriptional transactivator complex with TcF/Lef, β-catenin translocates to the nucleus.[20] Subsequently, transactivation of genes involved in cell migration will occur. It was found that high levels of FZD7 mRNA expression were almost exclusively associated with nuclear and/or cytoplasmic accumulation of β-catenin in HCC lines and human tumors with the wild type gene. However, as an exception, up-regulation of FZD7 gene expression was observed in the context of a heterozygous β-catenin exon-3 gene deletion in one HCC tumor (HCC #28) and cell line (HepG2). It is possible that an internal deletion of the β-catenin gene abolishes phosphorylation sites (localized within exon-3) and abrogates the canonical Wnt-Frizzled signaling via the mutated β-catenin allele.[37] In this setting, FZD7 may signal through either (a) the canonical β-catenin pathway via the wild-type β-catenin allele or (b) the non-canonical β-catenin-independent pathway involving the activation of protein kinase C(PKC).[29] Down-regulation of the Wnt-FZD7 signaling by ectopic expression of different dominant negative mutants of FZD7 receptors (i.e., the transmembrane FZD7-ΔC, or the secreted FZD7-ΔTΔC) is associated with markedly reduced accumulation of β-catenin protein in the cytoplasm and nucleus of HCC cell lines that display a homozygous wild-type β-catenin gene. However, the observed inefficiency of dominant negative mutant FZD7 receptors for reducing accumulation of the wild-type β-catenin protein in the environment of a heterozygous β-catenin-mutation, as was shown in HepG2 cells, emphasizes the potential cooperation between non-canonical and β-catenin independent pathways for mediating the Wnt-FZD7 signaling.

The Wnt/Frizzled signaling network influences diverse biological processes.[28] The β-catenin protein belongs to a family of structural proteins that includes catenins and cadherins. By forming a membrane associated complex, these proteins mediate adhesion and are essential for the processes of cellular motility and migration.[32,35] Therefore, the role of FZD7 gene expression in HCC cell motility was investigated. An ATP luminescence-based assay was used to quantify directional cell motility values in chemotaxis chambers and we observed that the magnitude of that steady state FZD7 mRNA levels were strongly correlated with enhanced motility of HCC cells. To further characterize the role of Wnt-FZD7 signal on cell motility, experiments demonstrated that interfering with the Wnt-FZD7 interaction by ectopic expression of dominant negative mutant FZD7 receptors led to marked reduction of HCC cell migration and occurred in the context of a homozygous wild-type β-catenin gene. These results support previous findings on the inhibitory effect of natural secreted Frizzled-related proteins on the motility of human glioma cells.[41] Of interest was the observation that the transmembrane FZD7-ΔC mutant receptor was more effective than the secreted FZD7-ΔTΔC soluble receptor with respect to inhibiting Huh7 cell motility and migration. It is likely that Huh7 cells can secrete yet unidentified Wnt ligand for binding to the FZD7 receptor. The secreted FZD7-ΔTΔC mutant receptor may be less efficient in binding, or could be overwhelmed by the high number of secreted Wnt ligand molecules. In contrast, the transmembrane FZD7-ΔC mutant receptor may be saturated and efficient since it has the capability to bind to the LRP5 co-receptor to allow for optimal transmission of the Wnt signal. Finally, the experiments suggest that the canonical β-catenin pathway may be involved in the FZD7-mediated regulation of Huh7 cell motility. Indeed, it has been observed that ectopic expression of a β-catenin mutant was able to restore high levels of motility in Huh7 cells where the Wnt/β-catenin mediated signal transduction cascade has been inhibited at the receptor level by stable expression of a dominant negative FZD7-ΔC construct.

In summary, deregulation of the Wnt-APC-β-catenin pathway is found in a number of human (colorectal, lung, breast, cervix, melanoma, and HCC) tumors.[6,11,22,26,27,31,38,40,45] Most reports have established that this deregulation may be due to β-catenin gene mutation.[13] This study shows for the first time that over 90% of human HCC have up-regulation of the FZD7 receptor gene and this phenomenon was functionally associated with stabilization of wild-type β-catenin and enhanced HCC cell motility. Therefore, enhanced FZD7 gene expression is the most common and one of the earliest genetic abnormality observed thus far in HCC and is probably responsible for the β-catenin accumulation in human HCC tumors without β-catenin, axin or APC mutations. Molecular mechanisms that may lead to up-regulation of FZD7 gene may include 1) paracrine or autocrine induction by Wnt ligands, 2) gene amplification and 3) demethylation of FZD7 gene promoter sequences.

Although the present study emphasized the canonical Wnt/β-catenin signaling pathway, Wnt/Frizzled signals may activate at least two other intracellular signaling pathways including the planar cell polarity pathway that signals through the small GTPase Rho, and another signaling cascade that activates isoforms of protein kinase C.[16,46] These pathways may play a role in the context of a homozygous wild-type β-catenin gene or in tumors with β-catenin mutations and deletions.

TABLE 1

FZD7 mRNA steady state levels assessed by quantitative real-time RT-PCR in paired samples including HCC tumor (T) versus the corresponding peritumorous liver (pT).

| Geographic Area | HCC Sample # | Etiology | T [FZD7 mRNA levels] | pT [FZD7 mRNA levels] | Ratio T/pT |
|---|---|---|---|---|---|
| Taiwan | 1 | HBV | 18.5 | 7.3 | 2.5 |
|  | 2 | HBV | 46.5 | 6.9 | 6.7 |

TABLE 1-continued

FZD7 mRNA steady state levels assessed by quantitative real-time RT-PCR in paired samples including HCC tumor (T) versus the corresponding peritumorous liver (pT).

| Geographic Area | HCC Sample # | Etiology | T [FZD7 mRNA levels] | pT [FZD7 mRNA levels] | Ratio T/pT |
|---|---|---|---|---|---|
| | 3 | HBV | 11.6 | 5.8 | 2.0 |
| | 4 | HBV | 53.1 | 7.6 | 7.0 |
| | 5 | HBV | 60.7 | 9.5 | 6.4 |
| | 6 | HBV | 16.0 | 3.3 | 4.8 |
| | 7 | HBV | 31.3 | 14.2 | 2.2 |
| | 8 | HBV | 17.1 | 18.5 | 0.9 |
| | 9 | HBV | 9.5 | 13.1 | 0.7 |
| | 10 | HBV | 19.6 | 6.5 | 3.0 |
| | 11 | HBV | 134.2 | 19.6 | 6.8 |
| | 12 | HBV | 657.1 | 10.2 | 64.4 |
| | 13 | HBV | 38.2 | 18.5 | 2.1 |
| | 14 | HBV | 9.5 | 3.6 | 2.6 |
| | 15 | HBV | 84.0 | 30.9 | 2.7 |
| | 16 | HBV | 38.2 | 6.9 | 5.5 |
| South Africa | 17 | HBV | 442.9 | 33.5 | 13.2 |
| | 18 | HBV | 8.4 | 0.7 | 12.0 |
| | 19 | HBV | 4.0 | 0.4 | 10.0 |
| | 20 | Hemochromatosis | 0.7 | 4.4 | 0.2 |
| | 21 | HBV | 33.5 | 6.2 | 5.4 |
| | 22 | HBV | 31.3 | 10.2 | 3.1 |
| | 23 | HBV | 4.7 | 1.1 | 4.3 |
| | 24 | HBV | 7.3 | 0.4 | 18.3 |
| | 25 | HCV | 29.1 | 3.3 | 8.8 |
| | 26 | HBV | 14.9 | 2.2 | 6.8 |
| | 27 | HBV | 33.1 | 4.7 | 7.0 |
| | 28 | Unknown | 296.4 | 2.2 | 134.7 |
| | 29 | Hemochromatosis | 14.9 | 8.4 | 1.8 |
| | 30 | HBV | 20.7 | 1.8 | 11.5 |

| | | Normal Liver | Normal Liver | | |
|---|---|---|---|---|---|
| Taiwan | 31 | 0.4 | | | |
| | 32 | 0.7 | | | |
| So. Africa | 33 | 1.8 | | | |
| | 34 | 1.1 | | | |

REFERENCES

1. Aberle, H., Schwartz, H. and Kemler. R. 1996. Cadherin-catenin complex: protein interactions and their implications for cadherin function. *J. Cell. Biochem.*, 61:514-523.
2. Aoki, M. Sobek. V. Maslyar, D., Hecht, A., and Vogt, P. K. 2002. Oncogenic transformation by β-catenin: deletion analysis and characterization of selected target genes. *Oncogene*, 21:6983-6991.
3. Bhanot, P., Brink, M., Samos, C. H., Hsieh, J. C., Wang, Y., Macke, J. P., Andrew, D., Nathans, J., and Nusse, R. 1996. A new member of the frizzled family from *Drosophila* functions as a Wingless receptor. *Nature*, 6588:225-230.
4. Bieche, I., Laurendeau, I. Tozlu, S., Olivi. M., Vidaud, D., Lidereau. R., and Vidaud M. 1999. Quantitation of MYC gene expression in sporadic breast tumors with a real-time reverse transcription-PCR assay. *Cancer Res.* 59:2759-2765.
5. Cagatay, T., and Ozturk, M. 2002. P53 mutation as a source of aberrant β-catenin accumulation in cancer cells. *Oncogene*, 21:7971-7980.
6. Candidus, S., Bischoff, P., Becker, K. F., and Hofler, H. 1996. No evidence for mutations in the alpha- and beta-catenin genes in human gastric and breast carcinomas. *Cancer Res.*, 56:49-52.
7. Cariani E., Lasserre, C., Seurin, D., Hamelin, B., Kemeny, F., Franco, D., Czech, M. P., Ullrich, A., and Brechot, C. 1988. Differential expression of insulin-like growth factor II mRNA in human primary liver cancers, benign liver tumors, and liver cirrhosis. *Cancer Res*, 48:6844-6849.
8. Carloni, V., Mazzocca. A., Pantaleo. P., Cordella, C. Laffi, G., and Gentilini, P. 2001. The integrin α6β1, is necessary for the matrix-dependent activation of FAK and MAP kinase and the migration of human hepatocarcinoma cells. *Hepatology*, 34:42-49.
9. Carruba, G., Cervello, M., Micell, M. D., Farruggio, R., Notarbartolo, M., Virrusou, L., Giannitrapani, L., Gambino, R., Montalto, G., Castagnetta L. 1999. Truncated form of b-catenin and reduced expression of wild-type catenins feature HepG2 human liver cancer cells. *New York Acad. Sci.*, 886:212-216.
10. Cheon, S. S., Cheah, A. Y., Turley, S., Nadesan, P., Poon, R., Clevers, H., and Alman, B. A. 2002. β-catenin stabilization dysregulates mesenchymal cell proliferation, motility, and invasiveness and causes aggressive fibromatosis and hyperplastic cutaneous wounds. *Proc. Natl. Acad. Sci. USA*, 10:6973-6978.
11. Chung., D. C. 2000. The genetic basis of colorectal cancer: insights into critical pathways of tumorigenesis. *Gastroenterology*, 119:854-8655.
12. Clevers, H. Axin and hepatocellular carcinomas. 2000. *Nat. Genet.*, 24:206-208.
13. de la Coste, A., Romagnolo, B., Billuart, P., Renard, C. A., Buendia, M. A., Sourbrane, O., Fabre, M., Chelly, J., Beldjord C., Kahn, A., and Perret, C. 1998. Somatic mutations of the β-catenin gene are frequent in mouse and human hepatocellular carcinoma. *Proc. Natl. Acad. Sci. USA,* 95:8847-8851.
14. de la Monte. S. M., Lahousse, S. A., Carter, J., and Wands, J. R. 2002. ATP luminescence-based motility-invasion assay. *Biotechniques.* 33:98-100.
15. de Souza, A. T., Hankins, G. R., Washington, M. K., Orton, T. C., and Jirtle, R. L. 1995. M6P/IGF2R gene is mutated in human hepatocellular carcinomas with loss of heterozygosity. *Nat. Genet.,* 11:447-449.
16. Devereux, T. R., Anna, C. H., Foley, J. F., White, C. M. Sills, R. C. and Barrett, J. C. 1999. Mutation of beta-catenin is an early event in chemically induced mouse hepatocellular carcinogenesis. *Oncogene,* 18:4726-4733.
17. Devereux, T. R., Stein, M. C., Flake, G. P., Yu, M. C., Zhang, Z. Q., London, S. J., and Taylor, J. A. 2001. CTNNB1 mutations and beta-catenin protein accumulation in human hepatocellular carcinomas associated with high exposure to aflatoxin B1. *Mol. Carcinog.,* 31:68-73.
18. Feitelson, M. A., Sun, B., Tufan, N. L. S., Liu, J., Pan, J., and Lian, Z. 2002. Genetic mechanisms of hepatocarcinogenesis. *Oncogene,* 21:2593-2604.
19. Gripon, P., Rumin, S., Urban S., Le Seyec, J., Glaise, D., Cannie, I. Guyomard, C., Lucas, J., Trepo, C., and Guguen-Guillouzo, C. 2002. Infection of a human hepatoma cell line by hepatitis B virus. *Proc. Natl. Acad. Sci. USA,* 24:15655-15660.
20. He, T. C., Sparks, A. B., Rago, C., Hermeking, H., Zawel, L. Da Costa, L. T., Morin, P. J., Vogelstein, B., and Kinzler, K. W. 1998. Identification of c-MYC as a target of the APC pathway. *Science,* 5382:1438-1441.
21. Holcombe, R. F., Marsh, J. L., Waterman, M. L., Lin, F., Milovanovic, T., and Truong, T. 2002. Expression of Wnt ligands and Frizzled receptors in colonic mucosa and in colon carcinoma. *Mol. Pathol.,* 55:220-226.
22. Hommura, F., Furuuchi, K., Yamazaki, K., Ogura, S., Kinoshita, I., Shimizu, M., Moriuchi, T., Katoh, H., Nishimura, M., and Dosaka-Akita. H. 2002. Increased expression of beta-catenin predicts better prognosis in non-small cell lung carcinomas. *Cancer,* 94:752-758.
23. Hsu, I. C., Metcalf, R. A., Sun, T., Welsh, J. A., Wang, N. J., and Harris, C. C. 1991. Mutational hotspot in the p53 gene in human hepatocellular carcinomas. *Nature,* 350: 427-428.
24. Hsu, H. C., Jeng Y. M., Mao, T. L., Chu, J. S., Lai, P. L., and Peng, S. Y. 2000. β-catenin mutations are associated with a subset of low-stage hepatocellular carcinoma negative for hepatitis B virus and with favorable prognosis. *Am. J. Pathol.,* 157:763-770.
25. Huang, H., Fuji, H., Sankila, A., Mahler-Araujo, B. M., Matsuda., M., Cathomas, G., and Ohgaki, H. 1999. β-catenin mutations are frequent in human hepatocellular carcinomas associated with hepatitis C virus infection. *Am. J. Pathol.,* 155:1795-1801.
26. Inagawa, S., Itabashi. M. Adachi, S., Kawamoto, T., Hori, M., Shimazaki, J., Yoshimi, F., and Fukao, K. 2002. Expression and prognostic roles of β-catenin in hepatocellular carcinoma: correlation with tumor progression and postoperative survival. *Clin. Cancer Res.,* 8:450-456.
27. Johnsson, M., Borg, A., Nilbert, M., and Andersson, T. 2000. Comments on involvement of adenomatous polyposis coli (APC) β-catenin signaling in human breast cancer. *Eur. J. Cancer,* 36:242-248.
28. Jones, S. E., and Jomary, C. 2002. Secreted Frizzled-related proteins: searching for relationships and patterns. *BioEssays,* 24:811-820.
29. Kuhl, M., Sheldahl, L. C., Park, M., Miller, J. R., and Moon, R. T. 2000. The Wnt/$Ca^{2+}$ pathway. A new vertebrate Wnt signaling pathway takes shape. *Trends Genet.,* 16:279-283.
30. Laurent-Puig, P., Legoix, P., Bluteau, O., Belghiti, J., Franco, D., Binot, F., Mones, G., Thomas, G., Bioulac-Sage, P., and Zucman-Rossi, J. 2001. Genetic alterations associated with hepatocellular carcinomas define distinct pathways of hepatocarcinogenesis. *Gastroenterology,* 120: 1763-1773.
31. Lin, S. Y., Xia, W., Wang, J. C., Kwong, K. Y., Spohn, B., Wen, Y., Pestell, R. G., and Hung, M. C. 2000. β-catenin, a novel prognostic marker for breast cancer: its roles in cyclin D1 expression and cancer progression. *Proc. Natl. Acad. Sci. USA.,* 7:4262-4266.
32. Liu, D., el-Hariry, I., Karayiannakis, A. J., Wilding, J., Chinery, R., Kmiot, W., McCrea, P. D., Gullick, W. J. and Pignatelli. M. 1997. Phosphorylation of β-catenin and epidermal growth factor receptor by intestinal trefoil factor. *Lab. Invest.,* 6:557-563.
33. Maloney, J. A., Tsygankova, O., Szot, A., Yang, L., Li, Q. and Williamson, J. R. 1998. Differential translocation of protein kinase C isozymes by phorbol esters, EGF, and ANG II in rat liver WB cells. *Cell Physiol.* 274:974-982.
34. Monga, S. P. S., Mars, W. M., Pediaditakis. P., Bell, A., Mule, K., Bowen, W. C., Wang, X., Zarnegar, R., and Michalopoulos, G. K. 2002. Hepatocyte growth factor induces Wnt-independent nuclear translocation of β-catenin after Met-β-catenin dissociation in hepatocytes. *Cancer Res.,* 62:2064-2071.
35. Muller, T., Choidas, A., Reichmann, E., and Ullrich, A. 1999. Phosphorylation and free pool of beta-catenin are regulated by tyrosine kinases and tyrosine phosphatases during epithelial cell migration. *J. Biol. Chem.,* 15:10173-10183.
36. Nhieu, J. T., Renard, C. A., Wei, Y., Clerqui, D., Zafrani, E. S., and Buendia M. A. 1999. Nuclear accumulation of mutated β-catenin in hepatocellular carcinoma is associated with increased cell proliferation. *Am. J. Pathol.,* 155: 703-710.
37. Noort, M. V., Meeldijk, J., van der Zee, R., Destree, O., and Clevers, H. 2002. Wnt signaling controls the phosphorylation status of β-catenin. *J. Biol. Chem.,* 20:17901-17905.
38. Park, W. S., Oh, R. R, Park, J. Y., Kim. P. J., Shin, M. S., Lee, J. H., Kim, H. S., Lee., S. H., Kim, S. Y., Park, Y. G., et al. 2001. Nuclear localization of β-catenin is an important prognostic factor in hepatoblastoma. *J. Pathol.,* 193: 483-490.
39. Polakis, P. 1997. The adenomatous polyposis coli (APC) tumor suppressor. *Biochim. Biophys. Acta.,* 1332: F127-147.
40. Rimm. D. L., Caca, K. Hu, G. Harrison, F. B. and Fearon. E. R. 1999. Frequent nuclear/cytoplasmic localization of β-catenin without exon 3 mutations in malignant melanoma. *Am. J. Pathol.,* 154:325-329.
41. Roth. W., Wild-Bode, C. Platten, M., Grimmel, C., Melkonyan, H. S., Dichgans, J., and Weller, M. 2000. Secreted Frizzled-related proteins inhibit motility and promote growth of human malignant, glioma cells. *Oncogene,* 37:4210-4220.
42. Satoh, S., Daigo, Y., Furukawa, Y., Kato, T., Miwa, N., Nishiwaki, T., Kawasoe, T, Ishiguro, H., Fujita, M., Tokino, T., et al. 2000. AXIN1 mutations in hepatocellular carcinomas, and growth suppression in cancer cells by virus-mediated transfer of AXIN1. *Nat. Genet.,* 24:245-250.

43. Satyamoorthy, K., Li, G., Vaidya, B., Patel, D., and Herlyn, M. 2001. Insulin-like growth factor-1 induces survival and growth of biologically early melanoma cells through both the mitogen-activated protein kinase and β-catenin pathways. *Cancer Res.*, 61:7318-7324.

44. Tanaka, S., Akiyoshi, T., Mori, M., Wands, J. R., and Sugimachi, K. 1998. A novel frizzled gene identified in human esophageal carcinoma mediates APC/β-catenin signals. *Proc. Natl. Acad. Sci. USA*. 95:10164-10169.

45. Ueda, M. Gemmill, R. M., Wset, J., Winn, R., Sugita. M., Tanaka, M., Ueki, M., and Drabkin, H. A. 2001. Mutations of the beta- and gamma-catenin genes are uncommon in human lung, breast, kidney, cervical and ovarian carcinomas. *Br. J. Cancer;* 85:64-68.

46. Weeraratna, A. T., Jiang, Y., Hostetter. G., Rosenblatt, K., Duray, P., Bittner, M., and Trent, J. M. 2002. Wnt5a signaling directly affects cell motility and invasion of metastatic melanoma. *Cancer Cell*, 3:279-288.

47. Wong, C. M., Fan, S. T., and Ng, I. O. 2001. β-catenin mutation and overexpression in hepatocellular carcinoma: clinicopathologic and prognostic significance. *Cancer;* 92:136-145.

48. Yeh, Y. C., Tsai. J. F. Chuang, L. Y., Yeh, H. W., Tsai, J. H., Florine, D. L., and Tam, J. P. 1987. Elevation of transforming growth factor alpha and its relationship to the epidermal growth factor and alpha-fetoprotein levels in patients with hepatocellular carcinoma. *Cancer Res.*, 47:896-901.

49. Zhang, X. K., Huang, D. P., Qiu, D. K., and Chiu, J. F. 1990. The expression of c-myc and c-N-ras in human cirrhotic livers, hepatocellular carcinomas and liver tissue surrounding the tumors. *Oncogene*, 5:909-914.

50. Zhang, X., Xu, H. J., Murakami, Y., Sachse, R., Yashima, K., Hirohashi, S, Hu, S. X., Benedict. W. F., and Sekiya, T. 1994. Deletions of chromosome 13q, mutations in Retinoblastoma 1, and retinoblastoma protein state in human hepatocellular carcinoma. *Cancer Res.*, 54:4177-4182.

Example 2

Oncogenic Role of the Frizzled-7/β-catenin Pathway in Hepatocellular Carcinoma

Introduction

Hepatocellular carcinoma (HCC) is one of the most frequent fatal malignancies worldwide.[1] It occurs at a high rate in Asia and Africa[2] and has been gradually increasing in Western countries as well.[3,4] Although major environmental risks have been identified such as chronic hepatitis B and C virus infection, exposure to aflatoxin B1, alcohol consumption and anabolic steroids, the molecular mechanisms of hepatocarcinogenesis remain largely unknown.[5,6] Activation of cellular oncogenes (c-myc)[7], growth factors (insulin-like growth factor II and transforming growth factor type α)[8,9,10] in association with mutations of tumor suppressor genes (P53, RB, and IGFIIR)[8,11,12] have been described in human and animal models of HCC. In addition, loss of heterozygosity (LOH) at chromosomes 1p, 4q, 6q, 8p, 9p, 16p, 16q, and 17p has also been identified at high frequency in HCC and suggest that several genes are involved in the multistep process of hepatocarcinogenesis.[5,13]

More recently, the observation of aberrant activation of the Wnt/β-catenin pathway as manifested by cellular and nuclear accumulation of this protein due to mutations of the β-catenin gene has contributed to a better understanding of pathogenesis (14, 15). However, additional studies estimate that 46% of hepatic adenomas and between 35 to 80% of HCC have aberrant β-catenin cellular accumulation, not associated with mutations affecting the β-catenin gene. In addition, Axin1 and APC gene mutations are rare in HCC and thus, the mechanisms of wild-type β-catenin accumulation in the majority of HCC tumors have yet to be determined. [16, 17, 18, 19] It is possible that other upstream components of this signaling pathway stabilize wild-type β-catenin in the cytoplasm to allow nuclear translocation and up-regulation of genes associated with the malignant phenotype.[21]

The Frizzled receptors of the Wnt/β-catenin signal transduction cascade have been recently identified. They are composed of seven-transmembrane spanning domains and act as receptors for Wnt proteins.[22] The canonical Wnt/Frizzled signaling network influences diverse biological processes ranging from cell fate determination to cell motility and proliferation. [21, 23] The Wnt/Frizzled signal is also transduced by the non-canonical small G-protein RhoA/c-Jun NH2-terminal kinase (JNK), or the Ca2+-calmodulin-dependent protein kinase II (CaKII) and protein kinase C(PKC) (24). Overexpression of Wnt ligands and/or Frizzled receptors have been found in tumors derived from esophagus, colon, and skin.[25, 26, 27] The human Frizzled type 7 receptor (FZD7) has been cloned and identified.[25] Additional experiments revealed that FZD7 overexpression was able to stabilize wild-type β-catenin and induce its translocation into the nucleus; the functional consequence of this event was an increase in cell motility and migration. In contrast, down-regulation of the Wnt/FZD7 signal leads to inactivation of the β-catenin cascade and results in reduced cellular motility and invasiveness. [21, 25] Recently, the FZD7 gene was found to be overexpressed in most human HCC tumors related to chronic hepatitis B infection and in all human hepatoma cell lines tested. Indeed, enhanced expression of FZD7 was associated with downstream activation of the canonical Wnt/β-catenin pathway in human HCC tumors and cell lines.[21]

In this context, transgenic mouse models provide unique opportunities to assess in vivo mechanisms involved in hepatocyte transformation.[20, 28] In order to determine if activation of the Wnt/β-catenin signal transduction cascade occurs at the Frizzled receptor level and is an early and common event during mammalian hepatocarcinogenesis, we established an experimental paradigm that employed a series of single, and double transgenic strains to explore expression of the Frizzled (FZD) gene family members in association with downstream activation of various components of this pathway. These transgenic lines overexpress either alone or in combination: 1) a transforming protein [SV40 large T-antigen (Tag)],[29] 2) an oncogene [(c-myc)],[30] 3) a viral transactivating protein [(HBx)],[31] and 4) the insulin receptor substrate-1 (IRS-1) to provide a constitutive hepatocyte proliferative stimulus.[32] All four transgenic lines developed HCC at different rates. We observed FZD7 gene up-regulation in hepatic dysplasia during the evolution of HCC tumors in association with functional activation of the canonical Wnt/Frizzled/β-catenin cascade. These observations suggest that early activation of this pathway is common during the process of mammalian hepatocyte transformation.

Transgenic Mice

Generation of F7 SV40-Tag single transgenic, and X/c-myc double transgenic mice with their corresponding non-transgenic littermates sharing the same genetic background—i.e., C57B1/6 x DBA/2 for SV40-Tag and C57B1/6 for X/c-myc—has been previously described.[29,31] The 93-7 WHV/c-myc and IRS-1 single transgenic mice [30, 32] were mated to generate first generation (F1) IRS-1/c-myc double-transgenics, c-myc single-transgenics, and non-transgenic littermates, where all share the C57B1/6 and FBV genetic backgrounds from WHV/c-myc (C57B1/6) and IRS-1 (FBV) parental lines, respectively. The transgenes were identified by PCR analysis of DNA extracted from tail snipings using different sets of primers that cover a fragment of: 1) the human IRS-1 gene,[32] 2) the woodchuck c-myc oncogene,[33] or 3) the hepatitis B virus X gene.[34] For SV40-Tag mice, the Tag transgene was carried on the Y chromosome allowing 100% penetrance in males. Animal housing and care were in accordance with NIH guidelines.

Histology

Hepatocellular carcinomas and the corresponding surrounding peritumorous liver
parenchyma, as well as tumor-free livers, were obtained from adult females and males at different ages (1 to 9 months). Five em-thick paraffin-embedded sections of liver were fixed in paraformaldehyde and stained with hematoxylin and eosin. Histopathological diagnosis was based upon criteria as previously described.[35]

RT-PCR Assays

The amount of FZD mRNA was quantified in unknown samples by measuring the Ct value followed by normalization to 18S ribosomal RNA (18S rRNA) after comparison to a standard curve for both FZD and 18S rRNA. The ratio of FZD/18S rRNA was subsequently normalized to a calibrator (mean value obtained from normal liver derived from littermates of the same genetic background) and expressed as relative abundance of FZD mRNA. Standards were prepared with 10-fold dilutions of the corresponding PCR products cloned into the pCR®2.1 Vector (Invitrogen, Life Technology). The specificity of the FZD or 18S rRNA inserts was provided by sequence analysis. Serial dilution of FZD and 18S rRNA containing plasmids were aliquoted and stored at −20° C. until use.

Primers were selected using the Primer3 website (www-genome.wi.mit.edu/cgibin/primer/primer3_www.cgi). Primers for FZD and 18S rRNA respectively were as follows: FZD1 (F: 5'-CAG AAC ACG TCC GAC AAA GG-3'(SEQ ID NO:33), R: 5'-TCC TTC TCC CCC AGA AAGTG-3' (SEQ ID NO:34)), FZD2 (F: 5'-GAG CAC CCT TTC CAC TGT CC-3' (SEQ ID NO:35), R: 5'-ACG GGC AAA ACG AGT CTC C-3' (SEQ ID NO:36)), FZD3 (F: 5'-ATC CCC GAC TTG TGG ATT TG-3' (SEQ ID NO:37), R: 5'-ATG GTG GCG AAC AAT CTC G-3' (SEQ ID NO:38)), FZD4 (F: 5'-GCA TGG AAG GAC CAG GTG AT-3' (SEQ ID NO:39), R: 5'-CTC CTT AGC TGA GCG GCT GT-3' (SEQ ID NO:40)), FZD5 (F: 5'-GGA TTA TAA CCG AAG CGA AAC C-3' (SEQ ID NO:41), R: 5'-TGC GCA CCT TGT TGT AGA GTG-3' (SEQ ID NO:42)), FZD6 (F: 5'-TTG GAT TTT GGT GTC CAA AGC-3' (SEQ ID NO:43), R: 5'-GGA GGG GCA CAC TGT TCA AT-3' (SEQ ID NO:44)), FZD7 (F: 5'-TAC CTG CCA GAC CCA CCT TT-3' (SEQ ID NO:45), R: 5'-GCG AAC CGT CTC TCC TCT TC-3' (SEQ ID NO:46)), FZD8 (F: 5'-GCT CTA CAA CCG CGT CAA GA-3' (SEQ ID NO:47), R: 5'-GCG CTC ATC CTG GCT AAA GA-3' (SEQ ID NO:48)), FZD9 (F: 5'-GTA TGG AGG CAC CCG AGA AC-3' (SEQ ID NO:50), R: 5'-CAC GAG CGA CTC TTC TCC AC-3' (SEQ ID NO:51)),18S rRNA (F: 5'-GGA CAC GGA CAG GAT TGA CA-3' (SEQ ID NO:52), R: 5'-ACC CAC GGA ATC GAG AAA GA-3' (SEQ ID NO:53)). BLASTN searches against dbEST and nr (the nonredundant set of GenBank database sequences) were conducted to confirm the gene specificity of the nucleotide sequences chosen for the primers as well as to establish the lack of DNA polymorphism. Primers were purchased from Invitrogen™, Life Technologies.

Total RNA was extracted from liver specimens by using TRIzol®. Reagent (Invitrogen Life Technology). The quality of RNA samples was determined by electrophoresis through agarose gels and staining with ethidium bromide; the 18S and 28S ribosomal RNA bands were visualized under UV light. Total RNA was treated with DNase-I, RNase-free (Roche Diagnostics Corporation, Indianapolis, USA) to remove contaminating genomic DNA. Reverse transcription of 250 ng total RNA was performed in a final volume of 20 µl containing 1×RT-Buffer (50 mM Tris-HCl, 8 mM MgCl2, 30 mM KCl, 1 mM dithiothreitol, pH 8.5), 250 µM each deoxynucleotide triphosphate, 40 units of RNase inhibitor, 3.2 µg random hexamers, 20 units of reverse transcriptase AMV all from Roche Diagnostics Corporation (Indianapolis, USA). The samples were incubated at 25° C. for 10 minutes and 42° C. for 1 hour. Reverse transcriptase was inactivated by heating at 99° C. for 5 minutes, and cooling at 4° C. for 5 minutes.

All PCR reactions were performed using an iCycler iQ™. Multi-Color Real Time PCR Detection System (Bio-Rad, Hercules, USA). For each run, a master mix was prepared on ice with 1×SYBR™ Green PCR Master Mix (Applied Biosystems, USA), 150 to 500 nM each primer, and cDNA from unknown samples (1 ng equivalent total RNA). The thermal cycling conditions comprised an initial step at 95° C. for 10 minutes, followed by 40 cycles at 95° C. for 15 seconds and 62° C. for 1 minute. Experiments were performed in duplicate. Each PCR run included FZD and 18S standard curves, a non-template control, and the unknown cDNAs analyzed for FZD and 18S RRNA copy numbers.

Protein Extraction and Western Blot Analysis

Frozen mouse liver samples were homogenized and sonicated in lysis buffer [30 mM Tris (pH 7.5), 150 mM NaCl, 1% NP-40, 0.5% Na deoxycholate, 0.1% SDS, 10% glycerol, and 2 mM EDTA] containing the Complete Protease Inhibitor (Roche Molecular Biochemicals). After clarifying the extracts, protein concentrations were determined with the BCA Protein Assay Kit (Pierce) using BSA as standard. Cytosolic subcellular fractionations were performed as previously described.[36] Aliquots of 25 to 50 µg protein were resolved on SDS/PAGE and transferred onto PVDF membranes (NEN™ Life ScienceProducts, Boston, Mass.) by electroblotting. The membranes were blocked with 5% nonfat dry milk in Tris-buffered saline containing 0.1% Tween 20 and then probed with a goat anti-mouse FZD7 polyclonal antibody diluted at 1:1,000 (RD Systems, Inc., Catalog number AF 198), a mouse anti-β-catenin monoclonal antibody diluted at 1:500 (Transduction Laboratories), an anti-phospho Thr41, Ser45 β-catenin antibody diluted at 1:500 (Transduction Laboratories), or an anti-β-actin antibody (1:1,000), rabbit polyclonal antibodies for GSK30, phospho-GSK3 β(Ser9) (Cell Signaling Tec., Beverly, Mass.). The primary antibody was followed by incubation with a secondary antibody conjugated with horseradish peroxidase diluted 1:10,000 and then revealed with the chemiluminescence imaging Western Lightning (PerkinElmer™ Life Sciences, Boston, Mass.). The blots were standardized for equal protein binding by Ponceau S red staining or β-actin labeling. The immunoreactive bands were analyzed using NIH imaging software and all values were normalized to the loading controls.

A rabbit polyclonal antibody was prepared against a human derived FZD7 peptide (QNTSDGSGGPGGGPTAYPTAPYLPD (SEQ ID NO:32), amino acids 163-187, NCBI Protein database accession no. BAA_34668) located in the extracellular domain of the receptor and sharing a high homology (identity=92%, NCBI Pairwise BLAST) with the corresponding mouse peptide (QNTSDGSGGAGGSPTAYPTAPYLPD (SEQ ID NO:54), amino acids 163-187, NCBI Protein database accession no. NP_03203). This peptide did not share significant homology with other members of the Frizzled family or other known proteins (NCBI Nucleotide Blast). Specificity of the rabbit anti-FZD7 polyclonal antibody was determined by ELISA assay following absorption of preimmune and post-immune rabbit sera incubated with the specific peptide, or with another peptide serving as a negative control but also located in the extracellular domain of human FZD7 receptor (LGER-DCGAPCEPGRANGLMYFKEEE (SEQ ID NO:55), amino acids 225-249, NCBI Protein database accession no. BAA_34668). Finally, the specificity of the antigen antibody interaction was further established by absorption of FZD7 immunoreactively as determined by Western blot analysis on tumor tissue with specific and not with non-relevant peptides as well as lack of FZD7 protein detection with addition of secondary antibody alone (data not shown).

Analysis of β-catenin Gene

The PCR amplifications were performed on a PTC-100™ Programmable Thermal

Controller (MJ Research, Inc.) using genomic DNA extracted and purified by standard techniques from frozen samples. Genomic DNA was amplified by a step-down PCR protocol using 100 ng of template DNA as described previously,[37] with a pair of primers, BCAT-EX1F, 5'-GCG TGG ACA ATG GCT ACT CAA G-3' (SEQ ID NO:56) (sense) and BCAT-EX3R, 5'-CTG GTC CTC ATC GTT TAG C-3' (SEQ ID NO:57) (antisense), which produced an amplicon enconmpassing the putative GSK3 β phosphorylation sites in β-catenin exon-2 (corresponding to human exon-3). PCR products were resolved in 1% agarose gel and visualized with ethidium bromide. No shorter PCR products corresponding to a deleted β-catenin gene were observed. Normal size PCR products were excised, and purified using the QIAEX II gel extraction kit (Qiagen, Inc.), and sequenced in both strands using the primers BCAT-EX2F, 5'-TGA TGG AGT TGG ACA TGG CCA TG-3' (SEQ ID NO:58) (sense) and BCAT-EX2R, 5'-CCC ATT CAT AAA GGA CTT GGG AGG-3' (SEQ ID NO:59) (antisense).

Statistical Analysis

The t-Student test and the non-parametric Mann-Whittney test were used for data with StatView Software Version 5.0 (SAS Institute Inc.). Tests were considered significant when their p values were <0.05.

Transgenic Models of HCC

Several transgenic murine models of hepatocarcinogenesis were employed since they develop preneoplastic hepatic lesions at different rates as well as by different molecular mechanisms during the evolution of tumors. A transforming protein (SV40 large Tantigen) that abrogates p53 function[29, 38] was used, as was an oncogene (c-myc) that provided both a proliferative and transforming stimulus,[30] a hepatitis B viral protein (HBx) with transcriptional transactivating properties that regulates cellular growth genes,[31] and a constitutive hepatic proliferative stimulus provided by activation of the insulin/IGF-1 signal transduction pathway via IRS-1. In this model, hepatocyte proliferation is mediated by stimulation through the mitogen activated protein kinase (MAPK) cascade.[32]

Figure 9:
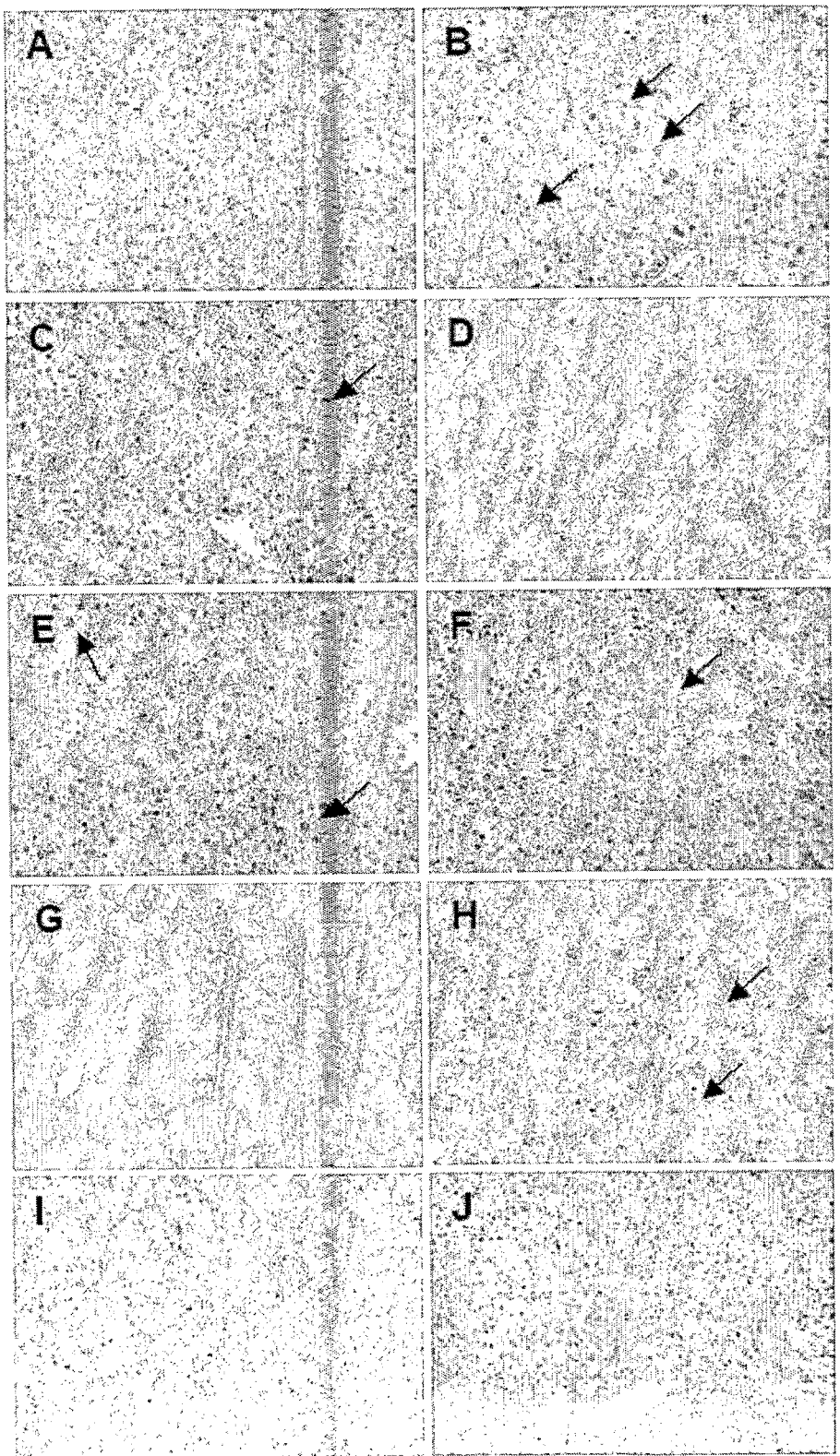
FIGS. 9A-9J are pictures illustrating the histopathology of IRS-1/c-myc, X/c-myc, and SV40-Tag transgenic mouse livers. Figs. H&E, original magnification ×100.
Figure 10:
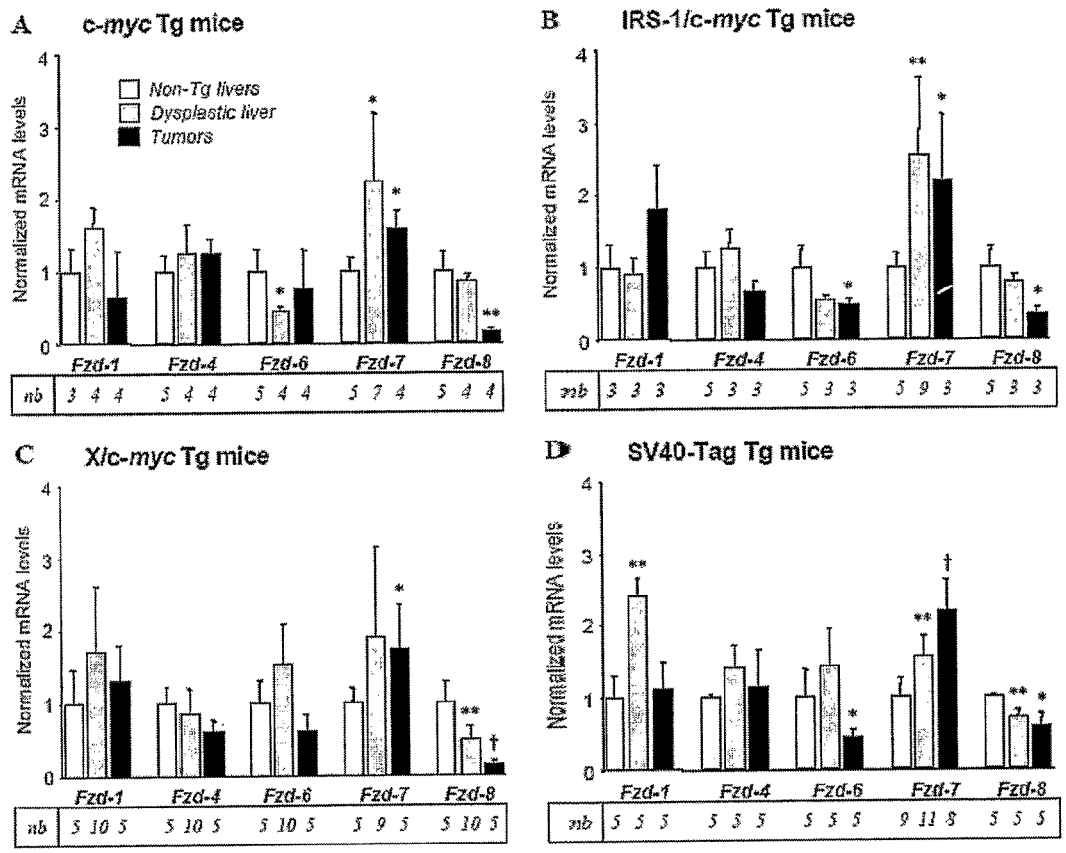
FIGS. 10A-10D are graphs illustrating steady state FZD1, FZD4, FZD6, FZD7, and FZD8 mRNA expression levels as measured by RT-PCR in transgenic mice.

In preliminary studies, it was found that both single c-myc and double IRS-1/c-myc transgenics developed precancerous hepatocyte dysplasia at about 8 weeks of age and exhibit well differentiated HCC tumors of the trabecular histologic type at about 36 weeks (FIG. 9D) as previously described.[30] As the HBx protein can accelerate c-myc induced tumors,[31] it was found that the double X/c-myc transgenics developed HCC earlier than single c-myc or IRS-1/c-myc double transgenic animals (median, 29 weeks) (FIG. 9G) as previously reported.[34] The most aggressive tumor model was the F7 strain of SV40-Tag single transgenic mice. These animals exhibited hepatocyte hyperplasia and dysplasia as early as 5 weeks followed by rapid onset of small cell type HCC at about 20 weeks (FIG. 9J).[29]

Expression of Frizzled Receptors During Evolution

The murine FZD gene family is composed of 9 known homologues, FZD1-9.[39] Pilot experiments were performed on 10 animals with high degree dysplasia adjacent to HCC. The mRNA levels of all Frizzled receptor genes were evaluated by RT-PCR. There was no expression of FZD2, FZD3, FZD5, and FZD9 in normal liver, dysplasia or HCC (data not shown). The remaining FZD1, FZD4, FZD6, FZD7, and FZD8 receptor genes displayed a significant and specific amplification signal as revealed by the melt curve, migration on agarose gels, and direct sequencing. Standard curves for FZD and 18S genes showed a linear relationship between the Ct and the log of the copy number ($R2 \geq 0.99$). The efficiency of the reactions was calculated as previously described[40] and ranged from 90 to 100% (data not shown). In order to compare different FZD mRNA levels, each value measured for FZD (recorded as FZD copy number per 109 18S rRNA copies) expression was normalized to the mean value obtained from the corresponding non-transgenic liver control group sharing the same genetic background.

FZD-1, -4, -6, -7, and -8 mRNA steady state levels were measured in HCC tumors and comparisons were made to: 1) precancerous regions characterized by widespread dysplastic hepatocytes and 2) non-transgenic normal liver. Precancerous liver was derived from the peritumorous region or from age-matched transgenic animals that had not yet developed HCC but contained multiple foci of dysplasia by histologic examination. It was observed that the FZD7 gene was the only member of the FZD family to be up-regulated at the mRNA level in both precancerous liver (n=36, P<0.001) and HCC (n=20, P<0.0001) as compared to nontransgenic liver control (n=19). FZD7 mRNA levels were overexpressed in 19/36 (53%) of precancerous liver and 14/20 (70%) of HCC as determined by the cut off value equal to the mean value of non-transgenic livers ±3SD (P=0.01). In contrast, FZD8 was substantially down regulated when comparing non-transgenic liver controls (n=15) to dysplastic liver (n=22, P<0.001) (23%, 5/22 precancerous livers) and subsequently to HCCs (n=17, P<0.0001) (60%, 10/17 HCCs). To specifically address the question that FZD gene expression pattern may be restricted to unique HCC models, we compared findings among the four different transgenic models (c-myc, SV40, IRS-1/c-myc, and X/c-myc). As shown in FIGS. 10A-10D, up-regulation of FZD7 in dysplasia and HCC and down-regulation of FZD8 gene expression principally in HCC were events common to all the animal models even when the tumors were presumably generated by different molecular mechanisms.

Relationship between FZD7 Expression and Evolution of HCC

Figure 11:
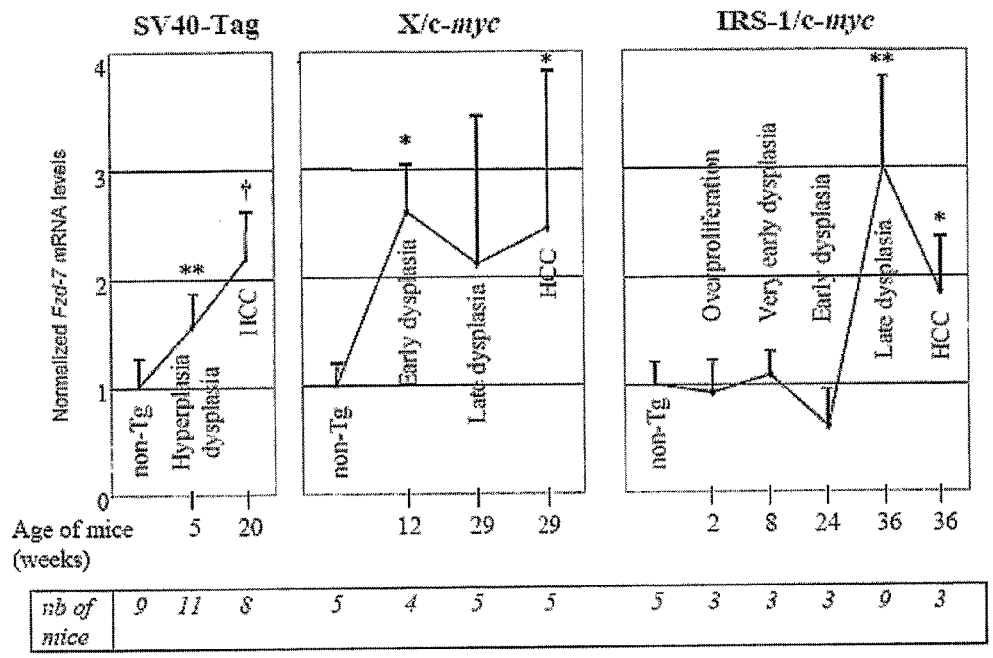
FIG. 11 is a series of line graphs illustrating the kinetics of FZD7 mRNA expression during the multistep hepatocarcinogenesis in SV40-Tag, X/c-myc, and IRS-1/c-myc transgenic strains. Each value was normalized to the mean value found in the liver of the corresponding non-transgenic littermates; nb=number of animals; t-Student test, (*)p<0.05, (**) p<0.01, (†) p<0.001.

To clarify the role of FZD7 gene during the natural course of tumor development, expression levels in IRS-1/c-myc, X/c-myc, and SV40-Tag models were compared in the context of dysplasia advancing to HCC. As shown in FIG. 11, SV40-Tag single transgenic mice develop dysplasia at 5 weeks and HCC at about 20 weeks in the setting of increasing FZD7 levels. In contrast, IRS-1/c-myc double and c-myc single transgenics develop well-differentiated trabecular HCC at about 36 weeks of age in association with hepatic dysplasia; FZD7 mRNA levels were also found to be up-regulated in 36 week-old dysplastic and tumorous liver areas. Finally, an intermediate model of dysplasia and HCC, as exemplified by the X/c-myc double transgenic model that develops well-differentiated trabecular HCC at 29 weeks was studied. Elevated FZD7 gene expression was observed both in 12-week-old dysplastic liver and HCC.

Expression of FZD7 Protein

Figure 12:
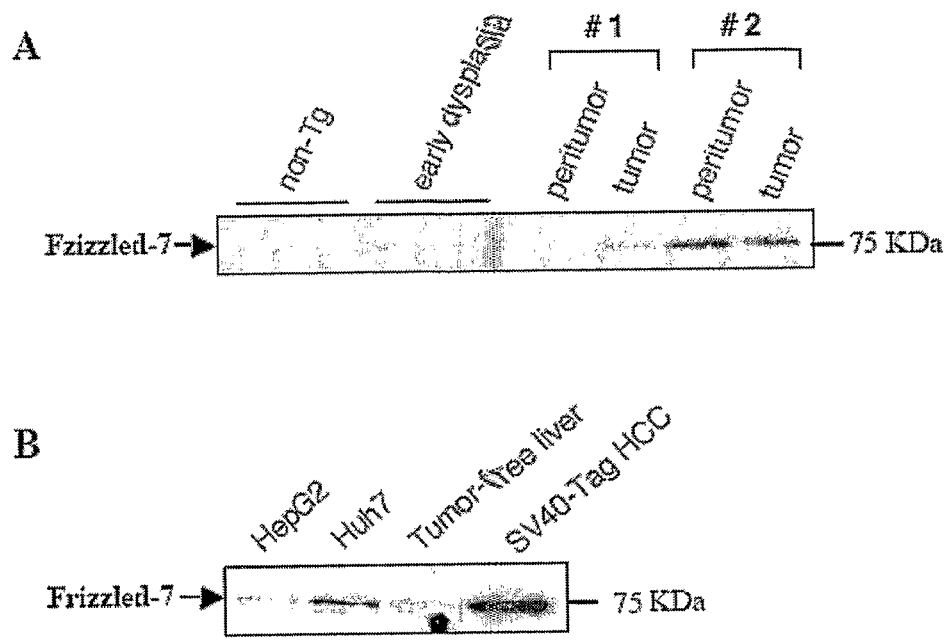
FIGS. 12A-12B are Western blots illustrating expression level of FZD7 receptor protein.

Correlations were made between FZD7 mRNA and protein levels in dysplastic liver as well as HCC. Western blot analysis was performed with goat anti-mouse polyclonal antibody specific to FZD7 as shown in FIG. 12A. Representative results revealed up-regulation of the protein in early dysplasia and HCC similar to the FZD7 mRNA results by RT-PCR. To further clarify the specificity of the protein band corresponding to FZD7 receptor observed on Western blot analysis with the goat polyclonal antibody (FIG. 12A), another rabbit polyclonal anti-peptide antibody was generated that reacts with both human and mouse FZD7 receptors. Specificity of the rabbit polyclonal antibody for FZD7 was confirmed by ELISA assay as described above. Furthermore, Western blot analysis using pre-immune and post-immune rabbit sera pre-incubated in the presence or absence of specific or non-relevant peptide confirmed the authenticity of the 75 KDa band found previously with both FZD7 polyclonal antibodies (data not shown). As shown in FIG. 12B, HCC cell lines Huh7 and HepG2 were used, expressing FDZ7 mRNA at high and low levels respectively by RT-PCR as positive controls.[21] Finally, the FZD7 protein was clearly increased in HCC as generated by expression of the SV40-Tag transgene compared to tumor-free liver and correlated with the elevated FZD 7 mRNA levels (FIG. 11).

Relationship between Frizzled-7 Expression and β-Catenin in Tumors

Figure 13:
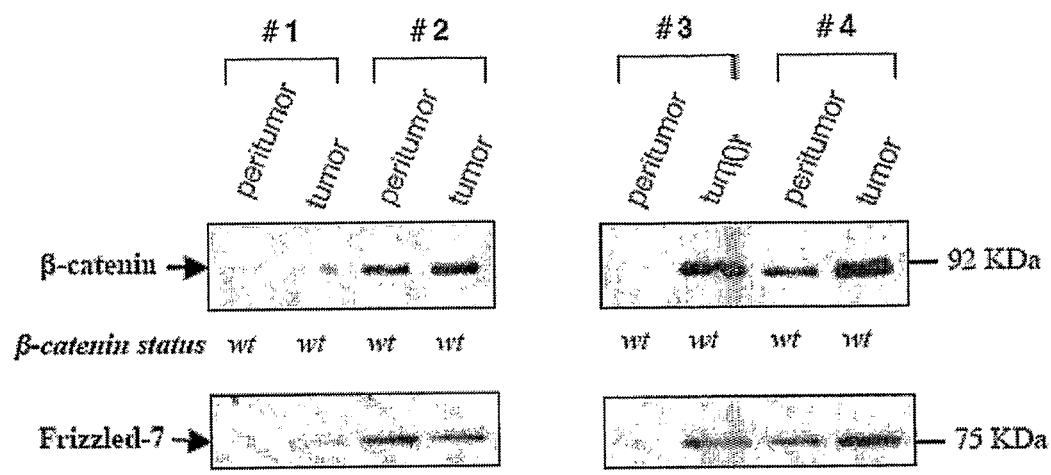
FIG. 13 is a set of Western blots that provide a comparison between FZD7 receptor and β-catenin protein levels in protein extracts derived from four X/c-myc double transgenic animals with HCC tumors. The status of β-catenin gene was assessed by sequencing exon-2 of a PCR amplification product as described in below; wt=wild-type.

The presence of β-catenin mutations during hepatocarcinogenesis in the mouse vary from 5 to 55% in HCC tumors and/or adenomas. β-catenin mutations have not yet been described in dysplastic liver,[14, 15, 41] which implies that β-catenin mutations are a late genetic event. One aim of this study was to clarify the potential impact of FZD7 up-regulation on wild-type β-catenin accumulation in tumors, as well as the adjacent peritumorous dysplastic liver. The SV40-Tag transgenic model does not display β-catenin mutations but was found not suitable for this study since the peritumorous areas were often invaded by small microscopic HCC nodules.[42] Therefore, FZD7 expression was compared to the β-catenin status in several tumors and dysplastic areas derived from the X/c-myc double transgenic strain. Histological examination had confirmed that the peritumorous regions were composed of dysplastic hepatocytes and were clearly separate from HCC tumors. The PCR analysis of genomic DNA and sequencing 4 of such tumors revealed no deletions or point mutations in the β-catenin exon 2 gene which includes the consensus motif for GSK3 β phosphorylation. Western blot analysis of protein extract derived from each tumor and corresponding peritumorous region revealed that FZD7 was overexpressed in both dysplastic and HCC areas in association with wild-type β-catenin cellular accumulation (FIG. 13). These findings suggest that the canonical Wnt/β-catenin pathway may be activated by overexpression of FZD7 receptors similar to observations made with human HCC tumors and cell lines.[21]

Relationship of Phospho-GSK3β to β-catenin Accumulation in Dysplasia and HCC

Figure 14:
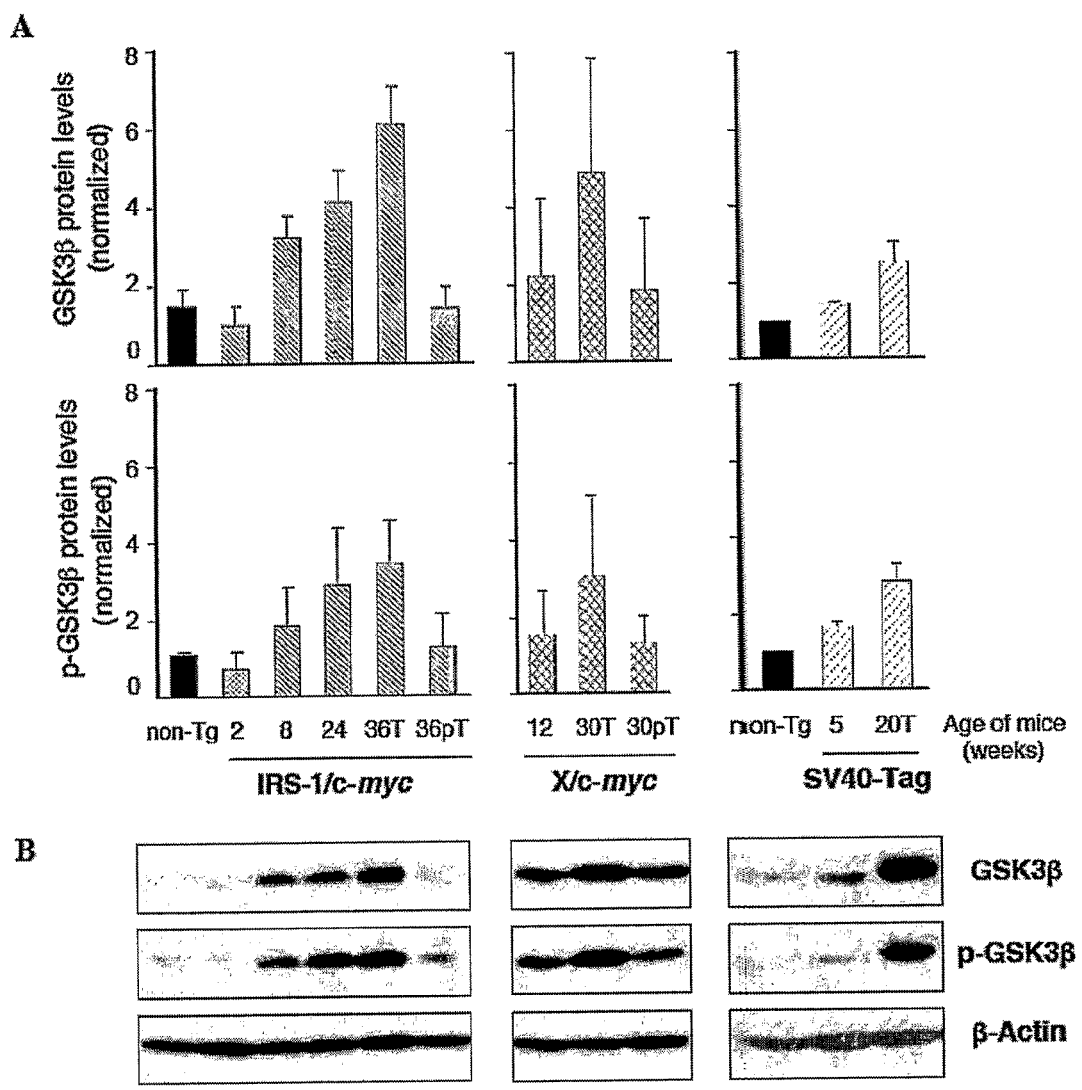
FIGS. 14A-14B are bar graphs and Western blots illustrating the level of GSK3β and phospho-GSK3 β during hepatocarcinogenesis.
Figure 15:
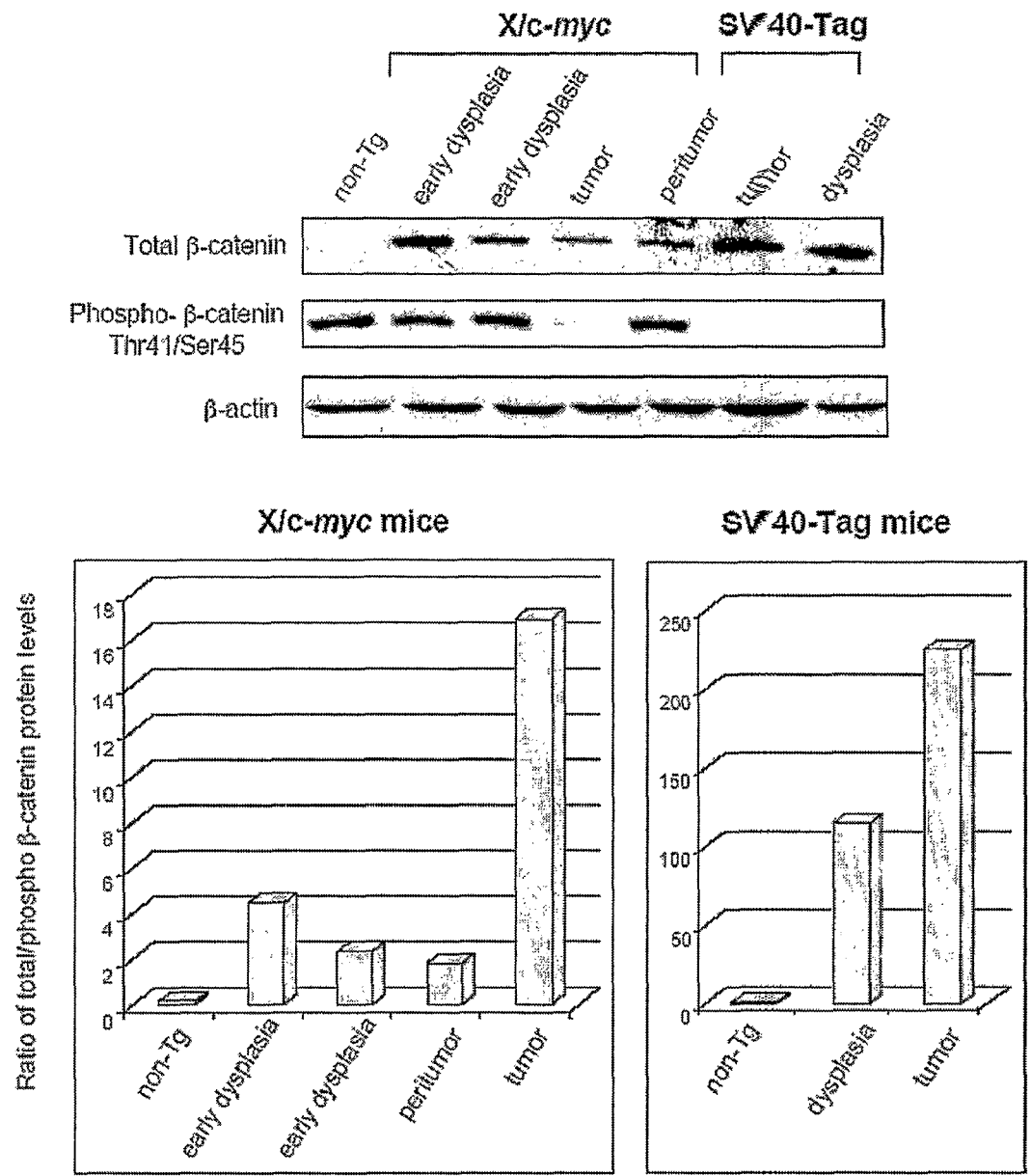
FIG. 15 is a set of Western blots and a bar graph that provide an exemplary ratio between the level of total β-catenin and phospho β-catenin (Thr41/Ser45). The cytosolic fraction of a protein extract derived from X/c-myc double transgenics and SV40-Tag single transgenics was used for immunoblotting. The β-catenin gene status was wild-type as revealed by sequencing of exon-2. Note the increased ratio of total β-catenin/phospho β-catenin with evolution of HCC tumor in the two transgenic livers.

Stabilization and accumulation of β-catenin in the cytosol is regulated by GSK3 β activity. In addition, elevated phospho-GSK3 β and β-catenin levels have been observed in HCC tissues.[43] To evaluate the potential effect of GSK3 β on the cellular accumulation of β-catenin, we measured GSK3 β and phospho-GSK3β by Western blot analysis. As shown in FIGS. 14A-14B, GSK3 β and phospho-GSK3β levels were increased in late dysplasia (24 weeks) and HCC tumor (36 weeks) of IRS-1/c-myc as well as in X/c-myc mice (30 weeks) and SV40-Tag mice (20 weeks). Enhanced phosphorylation of GSK3β has been associated with an increase in the ratio of total β-catenin/phospho-β-catenin and allows for stabilization and accumulation of β-catenin in the cytosol.[43] Therefore, such measurements were performed in cytosolic extracts derived from X/c-myc double transgenic and SV40-Tag single transgenic animals; the level of total and Phospho-β-catenin was measured by Western blot analysis. As shown in FIG. 15, the phospho-β-catenin level was decreased in tumors (X/c-myc, SV40-Tag) and dysplasia (SV40-Tag) as expected. If the canonical pathway was activated, then the ratio of total β-catenin to phospho β-catenin (Thr41/Ser45) should be much higher in tumor compared to non-Tg liver which was indeed the case. This observation is consistent with the hypothesis that activation of the canonical Wnt/β-catenin cascade occurs via overexpression of the FZD7 receptor murine models of in HCC.

Discussion

The expression patterns of the FZD gene family members have not been determined in HCC tumors derived from human, rat, or mouse liver tissues particularly in the context of functional activation of downstream components of Wnt/β-catenin signal transduction cascade. In this study, quantitative RT-PCR assays were developed and employed to investigate hepatic expression of all nine FZD genes identified thus far during the multistep process of murine hepatocarcinogenesis. The data provided herein describe a specific up-regulation of a frizzled receptor gene in precancerous tissue and HCC tumors in four different animal models. Furthermore, there is an apparent association with cellular accumulation of wild-type β-catenin in tumors overexpressing FZD7 in the absence of β-catenin exon-2 mutations. There is enhanced serine 9 phosphorylation of GSK3β and reduced Thr41/Ser56 phosphorylation of β-catenin leading or contributing to cellular accumulation of the protein.

These findings with four different transgenic models of HCC are similar to observations made with human HCC related to chronic hepatitis B infection.[21] In that study, β-catenin accumulation was observed in over 90% of HCC tumors containing the wild type β-catenin gene in the content of high-level FZD7 expression. The FZD7 receptor was also highly overexpressed in six HCC cell lines and functional analysis revealed that FZD7 mRNA levels correlated with robust Tcf/LEF transcriptional activity, and enhanced tumor cell motility and invasive properties. This biologic activity was blocked by a dominant negative mutant construct of FZD7 that decreased wild-type β-catenin accumulation in tumor cells. Taken together, the data suggest the canonical FZD7/β-catenin pathway is more commonly involved in the molecular pathogenesis of mammalian hepatocarcinogenesis than previously recognized since FZD7 overexpression occurs early in the dysplastic liver and stabilizes wild type β-catenin levels within hepatocytes.

Previous studies have emphasized that at least two major genetic pathways may be involved during the development of HCC in rodent models as well as in human disease. One pathway is characterized by an intact Wnt signaling cascade in the setting of a mutator phenotype and chromosomal instability. The second is characterized by disruption of the Wnt signaling cascade, but the process is not limited to activating β-catenin mutations since there is nuclear accumulation of the protein in the setting of a wild-type gene; this pathway is associated with a low rate of loss of heterozygosity (LOH).[13, 15, 20, 44, 45] Thus, β-catenin activation may be a very important event in both human and rodent hepatocarcinogenesis.[14, 15, 20, 21, 41] However, the canonical Wnt/β-catenin pathway has been found activated by β-catenin gene mutations in only 15-36% of human and murine HCC respectively; even more rare are Axin and APC mutations.[45, 46, 47] Therefore, it is possible that upstream FZD receptors and their respective but yet unknown Wnt ligands are potential candidates for activation of this cascade in HCC. Indeed, several FZD receptor genes have been found overexpressed in human tumors of different origin such as the esophagus (FZD7), stomach (FZD7), and colon (FZD1 and FZD2).[25, 26, 48]

The human FZD7 gene has been cloned and overexpression may lead to stabilization and nuclear translocation of wild-type β-catenin.[21, 25] In the present study, four different murine transgenic models of hepatocarcinogenesis were used (c-myc, IRS-1/c-myc, X/c-myc, and SV40-Tag) and it was found that FZD7 mRNA steady state levels are commonly up-regulated in approximately 70% of these tumors irrespective of the expressed transgene and in the context of a wild-type β-catenin gene. These findings are in general agreement with a 84% and 34% frequency of aberrant accumulation of wild type β-catenin protein in tumors derived from c-myc/E2F-1 and c-myc transgenic mice, respectively.[20] Finally, none of the age matched single transgenic IRS-1 or HBx mice developed liver lesions or have increased FZD7 expression (data not shown). The molecular mechanisms that promote upregulation of the FZD7 gene are unknown. There are various possibilities that include: 1) paracrine or autocrine induction by Wnt ligands, 2) gene amplification, and 3) demethylation of the FZD7 gene promotes sequences.

The stability of β-catenin in tumor cells is strongly enhanced by mutations or deletions affecting the GSK3β phosphorylation site and the ubiquitination consensus sequences (49). Stabilized forms of β-catenin accumulate in the cytoplasm, translocate to the nucleus and bind LEF/Tcf factors, thereby stimulating transcription of a number of cellular targets genes.[50] In contrast to previous studies showing a significant correlation between the presence of stabilizing mutations of the gene and nuclear accumulation of the protein in human liver tumors,[14,37] several studies have failed to detect nuclear accumulation of mutated β-catenin protein in murine HCC.[51, 52] Furthermore, recent findings have suggested that modest cytosolic accumulation of β-catenin can induce neoplastic transformation of normal epithelial cells,[53,54] and may transduce Wnt signals by exporting Tcf from the nucleus or by activating it in the cytoplasm.[55]

β-catenin accumulation in tumor derived protein extracts was also investigated, and both cytoplasmic and nuclear accumulation in murine as well as in human tumors[21] that contain the wild type β-catenin gene was found. Of interest here is the finding in vivo that FZD7 gene up-regulation is associated enhanced accumulation of wild-type β-catenin protein in dysplastic hepatic foci prior to the development of HCC. In this context, there is also enhanced expression and phosphorylation of GSK3β and reduced Ser/Thr phosphorylation of β-catenin which presumably leads to cellular accumulation. These observations support previous findings in human tumors that demonstrates overexpression of FZD7 stabilizes the APC/β-catenin complex and promote wild-type β-catenin translocation into the nucleus.[25]

In view of a general consensus that tumor development proceeds through a succession of genetic changes that confers growth advantage,[56] it seems likely that activation of the Wnt/FZD7/β-catenin cascade is directly involved in the progression from dysplasia to frank tumor formation and thus represents an early event in the generation of a malignant phenotype by promoting the biologic activity of cell migration and invasion.[21] There was a striking down-regulation of FZD8 in 23% of precancerous liver with dysplasia and 60% of HCC tumors. Indeed, FZD8 down-regulation is a frequent phenomenon in HCC compared to the corresponding precancerous liver (6-fold mean decrease). Little is known about FZD8 function during hepatic oncogenesis. However, it is of interest that FZD8 can activate c-Jun N-terminal kinases (JNK) and trigger apoptotic cell death in a β-catenin independent manner during gastrulation of *Xenopus* embryos.[57]

Approximately 25% of murine tumors with a wild-type gene have little if any abhorrent accumulation of β-catenin. This finding raises the possibility there may be involvement of Wnt/Frizzled/β-catenin independent pathways as recently suggested by human studies.[45] In conclusion, this study suggests that the FZD7/β-catenin signaling pathway plays a key role in the multistep process of murine hepatocarcinogenesis. FZD7 up-regulation is associated with increased levels and phosphorylation GSK3β and promotes β-catenin stability and subsequent accumulation in the cytosol in both tumors and adjacent dysplastic tissues from four different HCC transgenic models. Because of similar findings in human tumors,[21] these transgenic mice are realistic animal models and provide novel molecular targets to access various therapeutic approaches in this devastating disease.

REFERENCES

1. Murray, C. J. L., and Lopez. A. D. 1997. Mortality by cause for eight regions of the world: global burden of disease study. *Lancet* 349:1269-1276.
2. Caselmann, W. H. and Alt, M. 1996. Hepatitis C virus infection as a major risk factor for hepatocellular carcinoma. *J. Hapatol.* 24:61-66.
3. Anthony, P. P. 2001. Hepatocellular carcinoma: an overview. *Histopathology* 39: 109-118.
4. El-Serag. H. B., Mason. A. C. 1999. Rising incidence of hepatocellular carcinoma in the United States. *N. Engl. J. Med.* 340(10):745-50.
5. Nagai, H., Pineau. P., Tiollais, P., Buendia, M. A. and Dejean. A. 1997. A comprehensive allelotyping of human hepatocellular carcinoma. *Oncogene* 14:2927-2933.
6. Idilman, R., De Maria, N., Colantoni, A., and Van Thiel, D. 1998. Pathogenesis of hepatitis B and C-induced hepatocellular carcinoma. *J. Viral. Hepat.* 5: 285-299.
7. Zhang, X. K., Huang, D. P., Qin, D. K., and Chiu, J. F. 1990. The expression of c-myc and c-N-ras in human cirrhotic livers, hepatocellular carcinomas and liver tissue surrounding the tumors. *Oncogene* 5:909-914.
8. de Souza, A. T., Halkins, G. R., Washington, M. K., Orton, T. C., and Jirtle, R. L. 1995. M6P/IGF2R gene is mutated in human hepatocellular carcinomas with loss of heterozygosity. *Nat. Genet.* 11: 447-449.
9. Cariani, E., Lasserre, C., Seurin, D., Hamelin, B., Kemeny, F., Franco, D., Czech, M. P., Ullrich, A., and Brechot, C., 1988. Differential expression of insulin-like growth factor II mRNA in human primary liver cancers, benign liver tumors, and liver cirrhosis. *Cancer Res.* 48: 6844-6849.
10. Yeh, Y. C., Tsai, J-F., Chuang, L. Y., Yeh, H. W., Tsai. J. H., Florine, D. L., and Tam, J. P. 1987. Elevation of transforming growth factor alpha and its relationship to the epidermal growth factor and alpha-fetoprotein levels in patients with hepatocellular carcinoma. *Cancer Res.* 47: 896-901.
11. Hsu, I. C., Metcalf. R. A., Sun, T., Welsh, J. A., Wang, N. J., and Harris, C. C. 1991. Mutational hotspot in the p53 gene in human hepatocellular carcinomas. *Nature* 350:427-428.
12. Zhang, X., Xu, H. J., Murakami, Y., Sachse, R., Yashima, K., Hirohashi, S., Hu, S. X., Benedict. W. F., and Sekiya, T. 1994. Deletions of chromosome 13q, mutations in Retinoblastoma 15 and retinoblastoma protein state in human hepatocellular carcinoma. *Cancer Res.* 54: 4177-4182.
13. Zimonjic, D. B., Keck, C. L., Thorgeirsson, S. S., and Popescu, N. C. 1999. Novel recurrent genetic imbalances in human hepatocellular carcinoma cell lines identified by comparative genomic hybridization. *Hepatology* 29: 1208-1214.
14. de la Coste, A., Romagnolo, B., Billuart, P., Renard, C. A., Buendia, M. A., Soubrane, O., Fabre, M., Chelly, J., Beldjord C., Kaln, A., and Perret, C. 1998. Somatic mutations of the β-catenin gene are frequent in mouse and human hepatocellular carcinoma. *Proc. Nat. Acad. Sci. USA* 95:8847-8851.
15. Calvisi, D. F., Factor, V. M., Loi, R., and Thorgeirsson, S. S. 2001. Activation of β-catenin during hepatocarcinogenesis in transgenic mouse models. *Cancer Res.* 61: 2085-2091.
16. Torbenson, M., Lee, J. H., Choti, M., Gag, W., Abraham, S. C., Montgomery, E., Boitnott, J., Wu, T. T. 2002. Hepatic adenomas: analysis of sex steroid receptor status and the Wnt signaling pathway. *Mod. Pathol.* 15(3): 189-96.
17. Hsu, H. C., Jeng, Y. M., Mao, T. L., Chu J. S., Lai., P. L., and Peng, S. Y. 2000. β-catenin mutations are associated with a subset of low-stage hepatocellular carcinoma negative for hepatitis B virus and with favorable prognosis. *Am. J. Pathol.* 157:763-770.
18. Devereux, T. R., Stem, M. C., Flake, G. P., Yu, M. C., Zhang. Z. Q., London. S. J., and Taylor, J. A. 2001. CTNNB1 mutations and beta-catenin protein accumulation in human hepatocellular carcinomas associated with high exposure to aflatoxin B1. *Mol. Carcinog.* 31:68-73.
19. Wong, C. M., Fan, S. T. and Ng, I. O. 2001. β-catenin mutation and over-expression in hepatocellular carcinoma: clinicopathologic and prognostic significance. *Cancer* 92:136-145.
20. Calvisi, D. F., Factor, V. M., Ladu, S., Conner, E. A., Thorgeirson, S. S. 2004. Disruption of β-catenin pathway or genomic instability define two distinct categories of liver cancer in transgenic mice. *Gastroenterology* 1126:1374-1386.
21. Merle. P., de la Monte, S. M., Kim, M., Herrmann, M., Tanaka, S., von dem Bussche, A., Kew. M., Trepo, C., Wands, J. R. 2004. Functional consequences of frizzled-7 receptor overexpression in human hepatocellular carcinoma. *Gastroenterology* In press.
22. Blanot, P., Brink, M., Samos, C. H., Hsieh, J. C., Wang, Y., Macke, J. P., Andrew, D., Nathans, J., and Nusse, R. 1996. A new member of the Frizzled family from *Drosophila* functions as a Wingless receptor. *Nature* 3; 8:225-230.
23. Jones, S. E., and Jomary, C. 2002. Secreted Frizzled-related proteins: searching for relationships and patterns. *BioEssays* 24:811-820.
24. Kuhl, M., Sheldahl, L. C., Park, M. Miller, J. R., and Moon, R. T. 2000. The Wnt/$Ca^{2+}$ pathway. A new vertebrate Wnt signaling pathway takes shape. *Trends Genet.* 16:279-283.
25. Tanaka, S., Akiyoshi, T., Mori, M., Wands, J. R., and Sugimachi, K. 1998. A novel frizzled gene identified in human esophageal carcinoma mediates APC/β-catenin signals. *Proc. Natl. Acad. Sci. USA* 95:10164-10169.
26. Holcombe, R. F., Marsh, J. L., Waterman, M. L., Lin, F., Milovanovic, T. and Truong, T. 2002. Expression of Wnt ligands and Frizzled receptors in colonic mucosa aid in colon carcinoma. *Mol. Pathol.* 55:220-226.
27. Weeraratna, A. T., Jiang, Y., Hostetter, G., Rosenblatt, K., Duray. P., Bittner, M., and Trent. J. M. 2002. Wnt5a signaling directly affects cell motility and invasion of metastatic melanoma. *Cancer Cell* 3: 279-288.
28. Fausto, N. 1999. Mouse liver tumorigenesis: models, mechanisms, and relevance to human disease. *Seminars in Liver Disease* 19: 243-252.
29. Dubois, N., Bemioun M., Allemand, I., Molina, T., Grimber, G., Daudet-Monsac, M., Abelanet, R., and Briand, P. 1991. Time-course development of differentiated hepatocarcinoma and lung metastasis in transgenic mice. *J. Hepatol.* 13: 227-239.
30. Etiemble, J., Decyott, C., Renard, C. A., Fourel, G., Shamoon, B., Vitvitski-Trepo, L., Hsu, T. Y., Tiollais, P., Babinet, C., and Buendia, M. A. 1994. Liver-specific expression and high oncogenic efficiency of a c-myc transgene activated by woodchuck hepatitis virus insertion. *Oncogene* 9:727-737.
31. Terradillos, O., Billet, O., Renard, C. A., Levy, R., Molina. T., Briand, P., and Buendia, M. A. 1997. The hepatitis B virus X gene potentiates c-myc-induced liver oncogenesis in transgenic mice. *Oncogene* 14:395-404.
32. Mohr, L., Tanaka, S., and Wands, J. R. 1998. Ethanol inhibits hepatocyte proliferation in insulin receptor substrate-1 transgenic mice. *Gastroenterology* 115:1558-1565.
33. Merle, P. Chevallier, M., Levy, R. Maisonnas, M., Terradillos. O., Si Ahmed, S. N., Trepo, C., Buendia, M. A., and Vitvitski, L. 2001. Preliminary results of interferon-alpha therapy on woodchuck hepatitis virus-induced hepatocarcinogenesis: possible benefit in female transgenic mice. *J. Hepatol.* 34:562-569.
34. Merle, P., Barraud, L., Lefincois, L., Chevallier, M., Maisonnas, M., Bordes, I., Savre-Train, I., Trepo, C., and Vitvitski, L. 2003. Interferon-alpha therapy dose- and time-dependently delays *Hepadnavirus*-related hepatocarcinogenesis in X/myc transgenic mice. *Oncogene* 22:2762-2771.
35. Frith, C. H., Ward, J. M., and Turusov, V. S. 1994. Tumors of the liver. In *Pathology of Tumors in Laboratory Animals*. V. Turusov and U. Mohr, editors. IARC. Lyon, France. Vol. 2:223-270.
36. Maloney, J. A., Tsygankova, O., Szot, A., Yang, L., Li, Q., Williamson, J. R. 1998. Differential translication of protein kinase C isozymes by phorbol esters, EGF, and ANG II in rat liver WB cells. *Am. J. Physiol.* 274:C974-982.
37. Tran Van Nhieu, J., Renard, C. A., Wei, Y., Cherqui, D., Zafrani, E. S., and Buendia, M. A. 1999. Nuclear accumulation of mutated β-catenin in hepatocellular carcinoma is associated with increased cell proliferation. *Am. J. Pathol.* 155:703-710.
38. Moore, M., Teresky, A. K., Levine, A. J., and Seiberg, M. 1992. p53 mutations are not selected for in simian virus 40 T-antigen-induced tumors from transgenic mice. *J. Virol.* 66:641-649.
39. Giles, R. H., van Es, J. H., and Clever, H. 2003. Caught up in a Wnt storm: Wnt signaling in cancer. *Biochim. Biophys. Acta* 1653:1-24.
40. Bieche, I., Laurendeau, I., Tozlu, S., Olivi. M., Vidaud, D., Lidereau. R., and Vidaud, M. 1999. Quantitation of MYC gene expression in sporadic breast tumors with a real-time reverse transcription-PCR assay. *Cancer Res.* 59:2759-2765.
41. Anna, C. H., Iida, M., Sills, R. C., and Devereux, T. R. 2003. Expression of potential beta-catenin targets, cyclin D1, c-Jun, c-Myc, E-cadherin, and EGFR in chemically induced hepatocellular neoplasms from B6C3F1 mice. *Toxicol. Appl. Pharmacol.* 190:135-145.
42. Umeda, T., Yamamoto, T., Kajino, K., and Hino, O. 2000. β-catenin mutations are absent in hepatocellular carcinomas of SVJ40 T-antigen transgenic mice. *Int. J. Oncol.* 16:1133-1136.
43. Ban, K. C., Singh, H., Krishnan, R, Seow, H. F. 2003. GSK-3β phosphorylation and alteration of β-catenin in hepatocellular carcinoma. *Cancer letters* 199:201-208.
44. Legoix, P., Bluteau, O., Bayer, J., Perret, C., Balabaud, C., Belghiti, J., Franco, D., Thomas, G., Laurent-Puig, P., and Zucman-Rossi, J. 1999. Beta-catenin mutations in hepatocellular carcinoma correlate with a low rate of loss of heterozygosity. *Oncogene* 18:4044-4046.
45. Laurent-Puig, P., Legoix P, Bluteau O, Belghiti J, Franco D, Binot F, Mones G, Thomas G, Bioulac-Sage P, and Zucman-Rossi J. 2001. Genetic alterations associated with hepatocellular carcinomas define distinct pathways of hepatocarcinogenesis. *Gastroenterology* 120:1763-1773.
46. Huang, H., Fuji, H., Sankila, A., Mahler-Araujo, B. M., Matsuda. M., Cathomas, G., and Ohgaki, H. 1999. Beta-catenin mutations are frequent in human hepatocellular carcinomas associated with hepatitis C virus infection. *Am. J. Pathol.* 155:1795-1801.
47. Satoh, S., Daigo, Y., Furukawa, Y., Kato. T., Miwa, N., Nishiwaki, T. Kawasoe, T., Ishiguro, H., Fujita, M., Tokino, T., et al. 2000. AXIN1 mutations in hepatocellular carcinomas, and growth suppression in cancer cells by virus-mediated transfer of AXIN1. *Nat. Genet.* 24:245-250.
48. Kirikosbi, H., Sekihara, H., and Katoh, M. 2001. Up-regulation of Frizzled-7 (FZD7) in human gastric cancer. *Int. J. Oncol.* 19:111-115.
49. Morin, P. J., Sparks, A. B., Korinek, V., Barker, N., Clevers, H., Vogelstein, B., and Kinzler, K. W. 1997, Activation of beta-catenin-Tcf signaling in colon cancer by mutations in beta-catenin or APC. *Science* 275:1787-1790.
50. Morin. P. J. Beta-catenin signaling and cancer. 1999. *Bioessays* 21:1021-1030.
51. Devereux. T. R., Anna, C. H., Foley, J. F. White, C. M., Sills, R. C., and Barrett, J. C. 1999. Mutation of beta-catenin is an early event in chemically induced mouse hepatocellular carcinogenesis. *Oncogene* 18:4726-4733.
52. Renard, C. A., Fourel, G., Bralet, M. P., Degott, C., de La Coste, A., Penet, C., Tiollais, P., and Buendia, M. A. 2000. Hepatocellular carcinoma in WHV/N-myc2 transgenic mice: oncogenic mutations of beta-catenin and synergistic effect of p53 mill alleles. *Oncogene* 19:2678-2686.
53. Kolligs, F. T., Hu, G., Dang, C. V., and Fearon, E. R. 1999. Neoplastic transformation of RK3E by mutant beta-catenin requires deregulation of Tcf/Lef transcription but not activation of c-myc expression. *Mol. Cell. Biol.* 19:5696-5706.
54. Orford, K., Orford, C. C., and Byers, S. W. 1999. Exogenous expression of beta-catenin regulates contact inhibition, anchorage-independent growth, anoikis, and radiation-induced cell cycle arrest. *J. Cell Biol.* 146:855-868.
55. Chan, S. K., and Stuhl. G. 2002. Evidence that Armadillo transduces wingless by mediating nuclear export or cytosolic activation of Pangolin. *Cell* 111:265-280.
56. Hanahan D., and Weinberg, R. A. 2000. The hallmarks of cancer. *Cell* 100:57-70.
57. Lisovsky, M., Itoh, K., and Sokol, S. Y. 2002. Frizzled receptors activate a novel JNK-dependent pathway that may lead to apoptosis. *Curr. Biol.* 12:53-58.

A number of embodiments of the invention have been described. Nevertheless, it will be understood that various modifications may be made without departing from the spirit and scope of the invention. Accordingly, other embodiments are within the scope of the following claims.

What is claimed is:

1. A method of determining whether a liver cell is, or is at risk for becoming, a cancer cell, the method comprising:
   (a) providing a test liver cell;
   (b) determining whether the cell's level of FZD7 expression is higher than that of a control cell; and
   (c) classifying the test cell as a cancer cell or at risk for becoming a cancer cell, if the test cell's level of FZD7 expression is higher than that of the control cell.

2. A method of determining whether a test tissue sample comes from a patient that is suffering from or at risk for liver cancer, the method comprising:
   (a) providing a liver test tissue sample obtained from the patient; and
   (b) determining whether the level of FZD7 expression in the test tissue sample is higher than that in a comparable tissue sample obtained from a healthy individual, wherein a higher level of expression in the test tissue sample is an indication that the patient is suffering from or is at risk for cancer.

3. The method of claim 1, wherein determining the level of FZD7 expression includes determining the amount of FZD7 mRNA in the test cell or test tissue sample.

4. The method of claim 3, wherein the amount of FZD7 mRNA is determined using a Northern blot assay or an RT-PCR assay.

5. The method of claim 1, wherein determining the level of FZD7 expression includes determining the amount of FZD7 protein in the test cell or test tissue sample.

6. The method of claim 5, wherein the amount of FZD7 protein is determined using an antibody.

7. The method of claim 6, wherein the antibody binds to SEQ ID NOS: 32 or 55.

8. The method of claim 1, further comprising determining whether the test cell's or test tissue's level of FZD8 expression is lower than that of a control cell or control tissue, wherein a lower level of expression of FZD8 indicates that (i) the test cell is, or is at risk for becoming, a cancer cell or (ii) the patient is suffering from or is at risk for cancer.

9. The method of claim 2, wherein the tissue sample provided in (a) is tumorous tissue or peritumorous tissue.

10. The method of claim 2, further comprising:
(c) deteimining whether the level of FZD8 expression in the test tissue sample is lower than that in a tissue sample obtained from a healthy individual, wherein a lower level of expression of FZD8 is an indication that the patient is suffering from or at risk for cancer.

11. The method of claim 2, wherein determining the level of FZD7expression includes determining the amount of FZD7 mRNA in the test cell or test tissue sample.

12. The method of claim 2, wherein determining the level of FZD7expression includes determining the amount of FZD7 protein in the test cell or test tissue sample.

* * * * *

UNITED STATES PATENT AND TRADEMARK OFFICE
CERTIFICATE OF CORRECTION

PATENT NO. : 7,867,705 B2  Page 1 of 1
APPLICATION NO. : 11/575627
DATED : January 11, 2011
INVENTOR(S) : Jack R. Wands et al.

It is certified that error appears in the above-identified patent and that said Letters Patent is hereby corrected as shown below:

Title Page; item (73);
Page 1, column 1, line 1, (Name of Assignee):
    delete "a" and replace with -- A --.

Column 1, line 10:
    delete "Incorporated" and replace with -- incorporated --.

Claim 10, column 103, line 10:
    delete "deteimining" and replace with -- determining --.

Claim 11, column 104, line 5:
    delete "FZD7expression" and replace with -- FZD7 expression --.

Claim 12, column 104, line 8:
    delete "FZD7expression" and replace with -- FZD7 expression --.

Signed and Sealed this
Twenty-second Day of March, 2011

David J. Kappos
*Director of the United States Patent and Trademark Office*